(12) United States Patent
Neubig et al.

(10) Patent No.: US 8,865,750 B2
(45) Date of Patent: Oct. 21, 2014

(54) SMALL MOLECULE INHIBITORS OF RGS PROTEINS

(75) Inventors: Richard Neubig, Ann Arbor, MI (US); Levi Blazer, Ann Arbor, MI (US); Stephen Husbands, Somerset (GB); Scott Larsen, South Lyon, MI (US); John Traynor, Ann Arbor, MI (US)

(73) Assignees: The Regents of The University of Michigan, Ann Arbor, MI (US); The University of Bath, Bath (GB)

( * ) Notice: Subject to any disclaimer, the term of this patent is extended or adjusted under 35 U.S.C. 154(b) by 0 days.

(21) Appl. No.: 13/458,233

(22) Filed: Apr. 27, 2012

(65) Prior Publication Data

US 2012/0277273 A1    Nov. 1, 2012

Related U.S. Application Data

(60) Provisional application No. 61/479,992, filed on Apr. 28, 2011.

(51) Int. Cl.
| | | |
|---|---|---|
| *A01N 43/82* | (2006.01) | |
| *A61K 31/41* | (2006.01) | |
| *C07D 417/00* | (2006.01) | |
| *C07D 513/00* | (2006.01) | |
| *A61K 31/433* | (2006.01) | |
| *C07D 417/06* | (2006.01) | |
| *C07D 285/08* | (2006.01) | |

(52) U.S. Cl.
CPC ............ *C07D 417/06* (2013.01); *A61K 31/433* (2013.01); *C07D 285/08* (2013.01)
USPC .......................................... 514/361; 548/130

(58) Field of Classification Search
USPC .......................................... 514/361; 548/130
See application file for complete search history.

(56) References Cited

U.S. PATENT DOCUMENTS

| | | | |
|---|---|---|---|
| 6,872,737 B2 * | 3/2005 | Gil et al. ........................ | 514/361 |
| 2003/0195238 A1 | 10/2003 | Gil et al. | |

FOREIGN PATENT DOCUMENTS

| | | |
|---|---|---|
| EP | 1586319 A1 | 10/2005 |
| WO | 2001/08685 A1 | 11/2001 |

OTHER PUBLICATIONS

Aguilar-Morante et al., "Inhibition of glioblastoma growth by the thiadiazolidinone compound TDZD-8." PLoS One. Nov. 8, 2010;5(11):e13879.
Blazer et al, "A nanomolar-potency small molecule inhibitor of regulator of G-protein signaling proteins." Biochemistry. Apr. 19, 2011;50(15):3181-92.
Castro et al., "Non-ATP competitive glycogen synthase kinase 3beta (GSK-3beta) inhibitors: study of structural requirements for thiadiazolidinone derivatives." Bioorg Med Chem. Jan. 1, 2008;16(1):495-510.
Cifelli et al., "RGS4 regulates parasympathetic signaling and heart rate control in the sinoatrial node." Circ Res. Aug. 29, 2008;103(5):527-35.
Clark et al., "Active Galpha(q) subunits and M3 acetylcholine receptors promote distinct modes of association of RGS2 with the plasma membrane." FEBS Lett. Feb. 20, 2007; 581(4):764-70.
Fu et al., "RGS-insensitive G-protein mutations to study the role of endogenous RGS proteins." Methods Enzymol. 2004; 389:229-43.
Goldenstein, "Regulator of G protein signaling protein suppression of Galphao protein-mediated alpha2A adrenergic receptor inhibition of mouse hippocampal CA3 epileptiform activity." Mol Pharmacol. May 2009;75 (5):1222-30.
Guzman et al., "Rapid and selective death of leukemia stem and progenitor cells induced by the compound 4-benzyl, 2-methyl, 1,2,4-thiadiazolidine, 3,5 dione (TDZD-8)." Blood. Dec. 15, 2007;110(13):4436-44.
Huang et al., "Pleiotropic phenotype of a genomic knock-in of an RGS-insensitive G184S Gnai2 allele." Mol Cell Biol. Sep. 2006; 26(18):6870-9.
Huang et al., "Resistance to Diet-induced obesity and Improved Insulin Sensitivity in Mice with a Regulator of G Protein Signaling-Insensitive G184S Gnai2 Allele." Diabetes 2008, 57:77-85.
Lan et al., "A point mutation in Galphao and Galphai1 blocks interaction with regulator of G protein signaling proteins." J Biol Chem. May 22, 1998;273(21):12794-7.
Levi Blazer, "Development of Small Molecule RGS Inhibitors as a Mechanism to Modulate G-protein Signaling." Thesis Defense, University of Michigan Medical School. Sep. 2010.
Martinez et al., "First non-ATP competitive glycogen synthase kinase 3 beta (GSK-3beta) inhibitors: thiadiazolidinones (TDZD) as potential drugs for the treatment of Alzheimer's disease." J Med Chem. Mar. 14, 2002;45 (6):1292-9.
Nasim et al., "N-Chlorosuccinimide is a convenient oxidant for the synthesis of 2,4-disubstituted 1,2,4-thiadiazolidine-3,5-diones" Tetrahedron Letters Jan. 21, 2009, 50(3): 257-259.
Remmers et al., "Interdomain interactions regulate GDP release from heterotrimeric G proteins." Biochemistry. Oct. 19, 1999;38(42):13795-800.
Roman et al., "Identification of small-molecule inhibitors of RGS4 using a high-throughput flow cytometry protein interaction assay." Mol Pharmacol. Jan. 2007;71(1):169-75.
Roman et al., "Polyplexed flow cytometry protein interaction assay: a novel high-throughput screening paradigm for RGS protein inhibitors." J Biomol Screen. Jul. 2009;14(6):610-9.

(Continued)

*Primary Examiner* — Kendra D Carter
(74) *Attorney, Agent, or Firm* — Tanya A. Arenson; Casimir Jones, S.C.

(57) ABSTRACT

The invention relates to compositions having RGS (regulator of G-protein Signaling) inhibiting activity, and methods of use thereof. In some embodiments, RGS-inhibiting compositions find use in research on or treatment of disease states (e.g., diabetes, epilepsy, neuropathic pain, depression and other diseases).

16 Claims, 24 Drawing Sheets

(56) References Cited

OTHER PUBLICATIONS

Roof et al., "Mechanism of action and structural requirements of constrained peptide inhibitors of RGS proteins." Chem Biol Drug Des. Apr. 2006;67(4):266-74.

Rosa et al., "Antidepressant-like effect of the novel thiadiazolidinone NP031115 in mice." Prog Neuropsychopharmacol Biol Psychiatry. Aug. 1, 2008;32(6):1549-56.

Sachs et al., "Gastric acid secretion: activation and inhibition." Yale J Biol Med. May-Aug. 1994; 67(3-4):81-95.

Selenica et al., "Efficacy of small-molecule glycogen synthase kinase-3 inhibitors in the postnatal rat model of tau hyperphosphorylation." Br J Pharmacol. Nov. 2007; 152(6):959-79.

Talbot et al., "RGS inhibition at G(alpha)i2 selectively potentiates 5-HT1A-mediated antidepressant effects." Proc Natl Acad Sci U S A. Jun. 15, 2010;107(24)11086-91.

Wang et al., "Differential modulation of mu- and delta-opioid receptor agonists by endogenous RGS4 protein in SH-SY5Y cells." J Biol Chem. Jul. 3, 2009;284(27)18357-67.

\* cited by examiner

CCG-203760

CCG-203762

CCG-203769

SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1
gcaggagcca tccctgacta gctttgacca ag     32

<210> SEQ ID NO 2
<211> LENGTH: 32
<212> TYPE: DNA
<213> ORGANISM: Artificial Sequence

```
<220> FEATURE:
<223> OTHER INFORMATION: Synthetic

<400> SEQUENCE: 2
cgtcctcggt agggactgat cgaaactggt tc                              32

<210> SEQ ID NO 3
<211> LENGTH: 35
<212> TYPE: DNA
<213> ORGANISM: Artificial Sequence
<220> FEATURE:
<223> OTHER INFORMATION: Synthetic

<400> SEQUENCE: 3
tggaattctg gttggccagt gaggagttca agaag                           35

<210> SEQ ID NO 4
<211> LENGTH: 35
<212> TYPE: DNA
<213> ORGANISM: Artificial Sequence
<220> FEATURE:
<223> OTHER INFORMATION: Synthetic

<400> SEQUENCE: 4
accttaagac caaccggtca ctcctcaagt tcttc                           35
```

SMALL MOLECULE INHIBITORS OF RGS PROTEINS

This application claims priority to provisional application 61/479,992, filed Apr. 28, 2011, which is herein incorporated by reference in its entirety.

STATEMENT REGARDING FEDERALLY SPONSORED RESEARCH OR DEVELOPMENT

This invention was made with government support under contract number DA023252 awarded by the National Institute on Drug Abuse, U.S. National Institutes of Health. The government has certain rights in the invention.

FIELD OF THE INVENTION

The invention relates to compositions having RGS (regulator of G-protein Signaling) inhibiting activity, and methods of use thereof. In some embodiments, RGS-inhibiting compositions find use in research on or treatment of disease states (e.g., diabetes, epilepsy, neuropathic pain, depression and other diseases).

BACKGROUND OF THE INVENTION

G protein coupled receptors (GPCRs) are key drug targets in a wide variety of therapeutic areas. Signaling by GPCRs is modulated by the Regulator of G protein Signaling (RGS) protein family. RGS4 modulates insulin release from the pancreas and seizure activity in a variety of epilepsy models and RGS4 is upregulated in neuropathic pain models.

Consequently, inhibition of RGS4 finds use in treating diabetes, epilepsy, depression, neuropathic pain, and other diseases.

SUMMARY OF THE INVENTION

The invention relates to compositions having RGS (regulator of G-protein Signaling) inhibiting activity, and methods of use thereof. In some embodiments, RGS inhibitors specifically target one or more RGS proteins (e.g., RGS4). In some embodiments, RGS-inhibiting compositions find use in research on or treatment of disease states (e.g., diabetes, epilepsy, neuropathic pain, depression and other diseases).

In some preferred embodiments, the invention relates to 4-[(4-fluorophenyl)methyl]-2-(4-methylphenyl)-1,2,4-thiadiazolidine-3,5-dione (compound CCG-50014), analogs and derivatives thereof.

In preferred embodiments, compositions of the present invention inhibit activity of an RGS protein (e.g., a protein with an RGS box) (e.g., RGS4). Such RGS inhibition may be reversible or irreversible.

Compositions of the present invention find use in treatment or research of diseases and conditions (e.g., diabetes, depression, neuropathic pain, epilepsy). In particularly preferred embodiments, compositions of the present invention find use in research or treatment of diseases or conditions in which RGS activity influences progression, risk, or development of disease or condition. In some embodiments, compositions of the present invention find use for in vitro inhibition of RGS. In some embodiments, compositions of the present invention find use for in vivo inhibition of RGS. In some embodiments, compositions of the present invention are provided as a component of a kit. In some embodiments, the kit comprises additional research tools and reagents, without limitation to the nature of the tools and reagents. Examples of tools and reagents include, but are not limited to, buffers, tubes, detection agents (e.g., fluorescent probes, reagents to detect colorimetric assay products, isotopes, etc.), extraction solutions, homogenization solutions, detergents, proteases, and the like.

For example, in some embodiments, the present invention provides a composition comprising a compound having the structure:

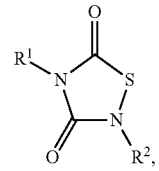

Wherein $R^1$ and $R^2$ may be the same or different, and are, for example, C2-C4 alkyl-$OR^3$, C1-C3 alkyl-heteroaryl-$R^3$, C4-C10 cycloalkyl, optionally substituted with O, C2-C6 alkynyl, optionally substituted (e.g., with O), C1-C8 alkyl, or C0-C3 alkyl-aryl; $R^3$ is C1-C6 alkyl, C0-C4 alkyl-aryl, C0-C4 alkyl-heteroaryl, or C2-C4 alkyl-$OR^4$, and $R^4$ is C1-C4 alkyl; or analogs, derivatives, mimetics, etc. thereof. In some embodiments, the heteroaryl is 1,2,3-triazole. In some embodiments, $R^3$ is $CH_3$, $CH_2CH_3$, or $CH_2Ph$. In some embodiments, $R^1$ and $R^2$ may be the same or different, and are selected, for example, C2-C4 alkyl-$OR^3$, C1-C3 alkyl-heteroaryl-$R^3$, C4-C10 cycloalkyl, wherein at least one $CH_2$ is replaced by O, C4-C10 cycloalkyl, wherein at least one H is replaced by a halogen (e.g., f), C2-C6 alkynyl, optionally substituted; $R^3$ is C1-C6 alkyl, C0-C4 alkyl-aryl, C0-C4 alkyl-heteroaryl, and C2-C4 alkyl-$OR^4$; and $R^4$ is C1-C4 alkyl. In some embodiments, R1 is C1-C3 alkyl-O—C1-C4 alkyl and R2 is a C1-C4 straight or branched alkyl.

In some embodiments, the compound is, for example,

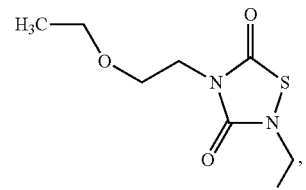

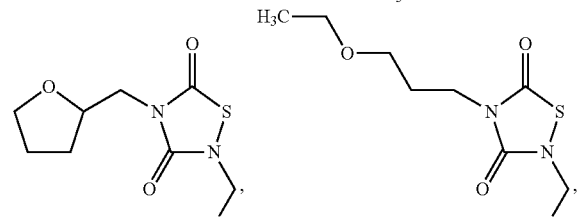

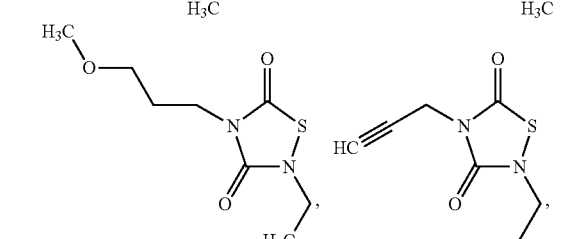

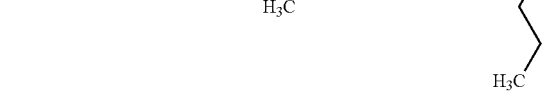

-continued

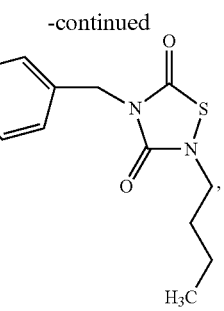

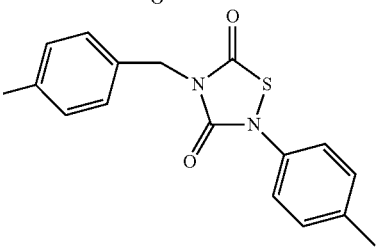, or

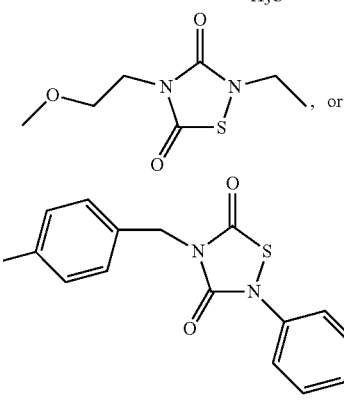

In some embodiments, the composition is a pharmaceutical composition. In some embodiments, the composition further comprises a pharmaceutically acceptable carrier.

In some embodiments, the present invention provides the use of the aforementioned compounds as a medicament. In certain embodiments, the present invention provides the use of any of the aforementioned compounds in the inhibition of a RGS domain protein. In still other embodiments, the present invention provides the use of any of the aforementioned compounds in the treatment of a disorder related to RGS protein activity (e.g., side effects of opioid medications, depression (e.g., by increasing sensitivity to selective-serotonin reuptake inhibitors (SSRIs) or without co-administration of an SSRI), Alzheimer's disease, Parkinson's disease, neuropathic pain, or insulin resistance).

Further embodiments of the present invention provide methods of inhibiting a regulator of G-protein Signaling (RGS) domain protein, comprising contacting said protein with an aforementioned compound. In some embodiments, the RGS protein is in a cell. In some embodiments, the cell is in an animal. In some embodiments, the animal exhibits symptoms of a disorder caused by aberrant RGS protein activity (e.g., including but not limited to, side effects of opioid medications, depression (e.g., by increasing sensitivity to selective-serotonin reuptake inhibitors (SSRIs) or without co-administration of an SSRI), Alzheimer's disease, Parkinson's disease, neuropathic pain, or insulin resistance) and the inhibiting reduces the symptoms.

Additional embodiments of the present invention provide a method of treating a disorder related to RGS protein activity, comprising a administering a compound that inhibits a regulator of G-protein Signaling (RGS) domain protein (e.g., the compounds described herein) to a subject exhibiting symptoms of a disorder caused by aberrant RGS protein activity (e.g., including but not limited to, side effects of opioid medications, depression (e.g., alone or in combination with an SSRI by increasing sensitivity to selective-serotonin reuptake inhibitors (SSRIs)), Alzheimer's disease, neuropathic pain, Parkinson's disease, or insulin resistance. In some embodiments, the administering reduces symptoms of the disorder.

Additional embodiments will be apparent to persons skilled in the relevant art based on the teachings contained herein.

DEFINITIONS

Figure 1:
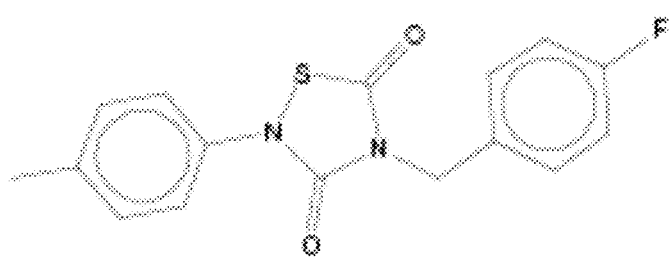
FIG. 1 shows the chemical structure of CCG-50014 (4-[(4-fluorophenyl)methyl]-2-(4-methylphenyl)-1,2,4-thiadiazolidine-3,5-dione).

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject at risk for disease" refers to a subject with one or more risk factors for developing a specific disease, e.g., diabetes, epilepsy. Risk factors include, but are not limited to, gender, age, genetic predisposition, environmental exposure to disease-precipitating factors, and previous incidents of disease, and lifestyle.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., diabetes, epilepsy). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present invention.

As used herein, the terms "RGS" or "regulators of G protein signaling" refer to proteins that contain an RGS box (e.g., RGS domain). Examples of human proteins containing RGS boxes include, but are not limited to, RGS1, RGS2, RGS3, RGS4, RGS5, RGS6, RGS7, RGS8, RGS9, RGS10, RGS11, RGS12, RGS13, RGS14, RGS16, RGS17, RGS18, RGS19, RGS20, and RGS21.

As used herein, the term "effective amount" refers to the amount of a compound (e.g., a RGS-inhibiting compound having a structure presented above or elsewhere described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., a RGS-inhibiting compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions characterized by viral infection (e.g., providing dosing, route of administration, decision trees for treating physicians for correlating patient-specific characteristics with therapeutic courses of action). The RGS-inhibiting compounds of the present invention (e.g. as shown in structures above and elsewhere presented herein) can be packaged into a kit, which may include instructions for administering the compounds to a subject.

As used herein, the term "chemical moiety" refers to any chemical compound containing at least one carbon atom. Examples of chemical moieties include, but are not limited to, aromatic chemical moieties, chemical moieties comprising sulfur, chemical moieties comprising nitrogen, hydrophilic chemical moieties, and hydrophobic chemical moieties.

As used herein, the term "heteroaryl" refers to an aromatic ring with at least one carbon replaced by O, S or N.

As used herein, the term "aliphatic" represents the groups including, but not limited to, alkyl, alkenyl, alkynyl, alicyclic.

As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, chemical moieties comprising N, S, O, $-NH_2$, $-NHCOCH_3$, $-OH$, lower alkoxy ($C_1$-$C_4$), and halo ($-F$, $-Cl$, $-Br$, or $-I$).

As used herein, the term "substituted aliphatic" refers to an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" and "heteroaryl" refer to an aromatic ring or fused aromatic ring system consisting of no more than three fused rings at least one of which is aromatic, and where at least one of the hydrogen atoms on a ring carbon has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to a cycloalkane possessing less than 8 carbons or a fused ring system consisting of no more than three fused cycloaliphatic rings. Examples of such include, but are not limited to, decalin and the like.

As used herein, the term "substituted cycloaliphatic" refers to a cycloalkane possessing less than 10 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicycloheptanes, octanes, and nonanes (e.g., nonrbornyl) and the like.

As used herein, the term "heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such include, but are not limited to, morpholino and the like.

As used herein, the term "substituted heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "alkyl" refers to a saturated chain or ring of single-bonded carbon and hydrogen atoms. The term "alky" includes "cycloalkyl (e.g., closed ring structures) and substituted or heteroalkyl (e.g., where one or more carbons are replaced by O, N, or S).

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "bicyclic" refers to a structure comprising two or more fused rings. The rings may be all alkyl, all aryl, or a combination of alkyl and aryl. Bicyclic rings may be substituted or unsubstituted.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

The term "derivative" of a compound, as used herein, refers to a chemically modified compound wherein the chemical modification takes place at any location of the compound (e.g., at a functional group).

As used herein, the term "toxic" refers to any detrimental or harmful effects on a cell or tissue as compared to the same cell or tissue prior to the administration of the toxicant.

As used herein, the terms "purified" or "to purify" refer to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., a compound of the present invention) to affect (e.g., inhibit the activity of) an RGS protein.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., inhibit an activity of an RGS protein). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that inhibit RGS proteins.

DETAILED DESCRIPTION OF THE INVENTION

The invention relates to compositions having RGS (regulator of G-protein Signaling) inhibiting activity, and methods of use thereof. In some embodiments, RGS-inhibiting compositions find use in research on or treatment of disease states (e.g., diabetes, epilepsy, neuropathic pain, depression and other diseases).

In experiments conducted during the course of developing some embodiments of the present invention, the biochemical mechanism of action of an RGS inhibitor that can potentiate G protein signaling in a number of living cell systems was analyzed. In some embodiments, compounds described herein are modifiers (e.g., irreversible modifiers) of cysteine residues. Prior to the present invention, the development of cysteine-reactive small molecule inhibitors into useful, target-specific research probes and therapeutic agents was challenging. Overly reactive compounds are often capable of non-specifically reacting with most solvent accessible thiols, leading to deleterious off-target effects in a physiological setting. Strikingly, covalent interactions of certain compounds (e.g. sulfonamide metabolites) with plasma proteins can lead to potentially life-threatening immune responses. The reducing intracellular environment of the cell is also biased against cysteine reactive compounds. The major intracellular reductant is glutathione—a cysteine-containing tripeptide present in the cell at a concentration of ~2 mM. Thiol-reactive compounds also are likely to have poor pharmacokinetic profiles due to the number of metabolic enzymes that act upon cysteine residues. These issues constitute major challenges to the development of the compound class described herein.

Figure 19:
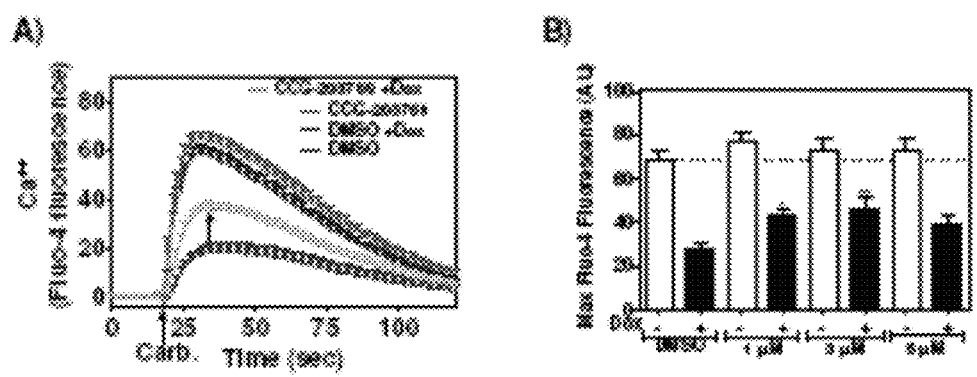
FIG. 19** shows CCG-203769 partially reverses the RGS4-mediated suppression of carbachol responsiveness in HEK293 cells expressing the M3 muscarinic receptor. A) Representative traces of cells responding to 3 nM carbachol. Doxycycline (+Dox) treated cells express RGS4 and show a significant suppression of $Ca_{2+}$ mobilization. Pretreatment of these cells for 15 minutes with 1 µM CCG-302769 (CCG-203769+Dox) partially rescued the $Ca^{2+}$ response. Data are presented as the mean±SEM of 12 wells per condition from a single experiment. B) Concentration dependence of the effect observed in A. Data are presented as the mean±SEM from three independent experiments. * $P<0.05$; ** $P<0.01$.

There are, however, a few successful therapeutics that function by covalently binding to cysteine. For example, the acid-reflux drug omeprazole operates in the stomach by covalently modifying a proton exchanger (Sachs, G., et al., Yale J Biol Med, 1994. 67(3-4): p. 81-95). In this case, the compound does not reach the systemic circulation to any great extent, so side effects are minimized. There is also a class of cysteine-reactive irreversible tyrosine kinase inhibitors, typified by CI-1033, that are currently in clinical trials. Cysteine reactive compounds thus have a place in modern pharmacology. To be truly useful however, these compounds require significantly more development than their non-reactive counterparts. During the course of developing some embodiments of the present invention, a compound discussed herein, CCG-50014, was discovered in a high throughput biochemical screen designed to identify inhibitors of 5 different RGS proteins (Roman et al., J Biomol Screen, 2009). CCG-50014 was identified as the most potent inhibitor from this screen with an $IC_{50}$ value <300 nM. While the present invention is not limited to any particular mechanism, and an understanding of the mechanism is not necessary to practice the present invention, the biochemical mechanism of action of this compound is contemplated. Novel analogs of CCG-50014 that have cellular activity are described herein. Embodiments of the present invention are not limited to CCG-50014 or analogs thereof. In some embodiments the present invention comprises compound CCG-203769, described herein (e.g., FIG. 19, Example 2), analogs and derivatives thereof, and/or their methods of use (e.g., for treatment of disease (e.g., diabetes, epilepsy)) or research on RGS (e.g., RS4) and pathways or events influenced by RGS (e.g., RGS4) activity.

The development of RGS inhibitors has till now been dominated by compounds that lacked efficacy in a cellular environment. The reasons for this lack of cellular activity stem from: permeability issues (e.g. peptides and possibly the CCG-638x family), weak in vitro activity (e.g. CCG-638x family and CCG-4986), and inactivation in the presence of reductants (e.g. CCG-4986 and the CCG-50014 family). Data presented herein demonstrate a family of RGS inhibitors that functions in a cellular environment. Early biochemical studies of this compound class discouraged further explanation by suggesting that it would lack cellular activity. As noted in Example 1, this family of compounds is inactivated by reductants, including physiologically relevant concentrations of the intracellular reductant glutathione. Furthermore, the cysteine-dependent reactivity of the compounds raised concerns about target specificity and potential off-target effects. It was with these issues in mind that cellular studies were attempted with CCG-50014 and some selected analogs.

A method was developed to directly measure the $G\alpha_O$/RGS4 PPI in living cells. This approach allowed determination if compounds can inhibit this PPI in living cells as they do in vitro (FIG. 17A). In this system, the RGS is expressed as a diffuse cytosolic protein until co-expression with $G\alpha_O$, which drives membrane association of RGS4. This co-localization is not induced by the co-expression of a mutant $G\alpha_O$ (G184S) that is insensitive to RGS GAP activity. The lack of interaction between the G184S $G\alpha_o$ mutant and RGS4 confirms the findings in cell and whole animal knock-in models (Fu, Y., et al., Methods Enzymol, 2004. 389: p. 229-43; Huang, X., et al., Mol Cell Biol, 2006. 26(18): p. 6870-9; Lan, K. L., et al., J Biol Chem, 1998. 273(21): p. 12794-7; Goldenstein, B. L., et al., Mol Pharmacol, 2009. 75(5): p. 1222-30; Goldenstein, B. L., et al., Mol Pharmacol, 2009; Huang, X., et al., Diabetes, 2008. 57(1): p. 77-85; Talbot, J. N., et al., Proc Natl Acad Sci USA. 107(24): p. 11086-91). CCG-50014 and CCG162 203769 are both able to inhibit the membrane localization of RGS4 in this assay, showing that these compounds can inhibit the $G\alpha_o$/RGS4 interaction in living cells. These data lend considerable credence to the notion that the functional effects observed in the subsequent studies stem from an inhibition of one (or more) RGS proteins.

To further confirm that the compounds could function in a cellular setting, a series of cellular studies were performed to test the ability of these compounds to block the negative regulation of GPCR signaling by RGS proteins. CCG-50014 could potentiate the signaling through the δ-opioid receptor selectively over the μ-opioid receptor in SH-SY5Y cells. The signaling pathways used in this study are all endogenously expressed in SH-SY5Y cells and this result correlates well with data showing RGS4 selectively inhibits the δ-opioid receptor [10]. These data are important because they show a small molecule RGS inhibitor having a functional effect on an endogenous signaling pathway.

While it is important to show that the compound can function on endogenous signaling pathways, it was desirable to also probe the actions of this compound in a more controlled manner. Several compounds were tested using cells stably expressing the muscarinic M3 receptor with RGS4 expression under doxycycline control. By measuring the $G_q$-dependent calcium mobilization induced by the M3 receptor, I CCG-230769 was shown to partially inhibit the effects of RGS4. CCG-50014, however, it induced a calcium transient on its own (FIG. 16A). These studies were important for two reasons: 1) it showed that the compound inhibits RGS4 under more controlled conditions than the SH-SY5Y experiments; and 2) these experiments revealed a previously unknown off-target effect elicited by some members of the CCG-50014 family.

A series of experiments was undertaken to probe the chemical space around the CCG-50014 scaffold. By analyzing ~80 analogs of CCG-50014 for a variety of parameters including potency, RGS selectivity, and solubility, a number of structure-activity relationships were identified around this scaffold. Potency against RGS proteins can be improved by shortening the side chains (R1/R2 in Table 3) to small alkyl chains. This also corresponded to an increase in RGS4 selectivity, although some analogs with phenyl rings at the R1/R2 position that have a small substituent in the para position on the R2 phenyl ring (e.g. CCG-203702) also display prominent selectivity for RGS4 over RGS8. Modification of the thiadiazolidine ring to a less reactive center drastically reduces activity. This SAR analysis also provided a means to identify compounds that did not produce the $Ca_{2+}$ mobilization off-target effect noted for CCG-50014. I identified three compounds (FIG. 16B) that potently inhibit RGS4 yet lack the ability to induce a $Ca^{2+}$ mobilization. Study of the SAR landscape surrounding CCG-50014 has yielded several compounds with improved properties and in vitro activity. These compounds, including CCG-203769, are currently being used in isolated organ and whole animal studies to determine their physiological effects on RGS activity and GPCR signaling.

There are at least two advantages that the CCG-50014 class of molecules has over previous generations of RGS inhibitors. The first—and presumably most important—is potency. CCG-50014 is nearly 3 orders of magnitude more potent at inhibiting RGS4 than any of the other small molecule RGS inhibitors examined. Therefore, even if a substantial fraction of the compound is rapidly metabolized or reacts with glutathione (or other non-target thiols), an active concentration of compound is likely to be present. Another set of advantages this compound has over prior generations of RGS inhibitors (especially CCG-63802) is improved cellular permeability and aqueous solubility. While solubility varies across this family of compounds, several have aqueous solubility >5 mM yet still retain cellular activity. These factors allow pharmacologically relevant concentrations of compound in the assay systems without interfering artifacts such as compound precipitation.

The CCG-50014 class of compounds contains the most potent RGS inhibitors identified herein and are small molecules that can inhibit the cellular activity of an RGS protein.

I. Compositions

Embodiments of the present invention provide compositions and methods for inhibiting RGS proteins. In some embodiments, inhibitors are selective for specific RGS proteins (e.g., RGS4). In some embodiments, the compounds have the structure

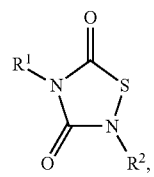

Wherein $R^1$ and $R^2$ may be the same or different, and are, for example, C2-C4 alkyl-$OR^3$, C1-C3 alkyl-heteroaryl-$R^3$, C4-C10 cycloalkyl, optionally substituted with O, C4-C10 cycloalkyl, wherein at least one H is replaced by a halogen (e.g., F), C2-C6 alkynyl, optionally substituted, C1-C8 alkyl, and Co-C3 alkyl-aryl. In some embodiments, $R^3$ is, for example, a C1-C6 alkyl, a C0-C4 alkyl-aryl, a C0-C4 alkyl-heteroaryl, or a C2-C4 alkyl-$OR^4$. In some embodiments, $R^4$ is C1-C4 alkyl. In some embodiments, the heteroaryl is 1,2,3-triazole. In some embodiments, $R^3$ is $CH_3$, $CH_2CH_3$ or $CH_2Ph$.

In some embodiments, the compound is, for example, selected from those described in Tables 2, 5 and 6 below. In some embodiments, the compound is

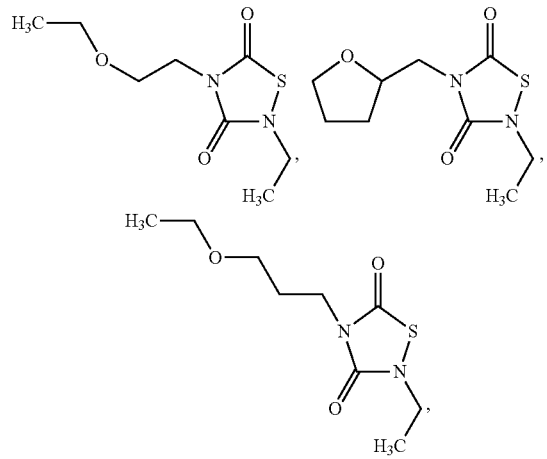

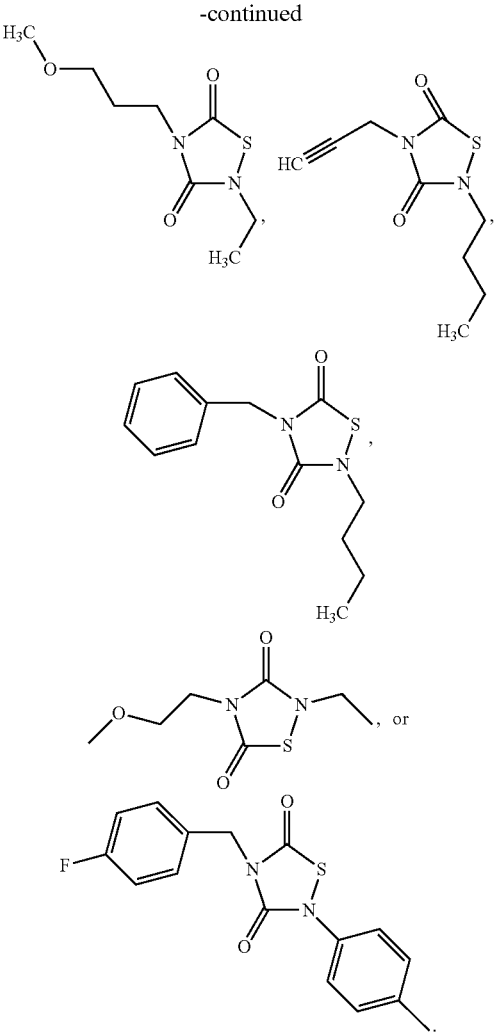

In some embodiments, the compound is a mimetic, stereoisomer, salt or derivative of a compound described herein.

The present invention also provides methods of modifying and derivatizing the compositions of the present invention to increase desirable properties (e.g., binding affinity, activity, and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In some embodiments, rational design methods are used to predict and model in silico ligand-receptor interactions prior to confirming results by routine experimentation.

The compounds of embodiments of the invention (or derivatives, mimetics, variants, etc. thereof) can be prepared from readily available starting materials using known methods. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Third Edition, Wiley, New York, 1999, and references cited therein.

If the compounds of embodiments of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

II. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to inhibit RGS proteins and treat associated disorders. The methods and techniques for preparing medicaments of a compound are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent (e.g., RGS inhibitor), as defined above, together with a solid support or alternatively, together with one or more pharmaceutically acceptable carriers and optionally other therapeutic agents. Each carrier should be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In some embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in an known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer a therapeutic agent (e.g., RGS inhibitor) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified herein as effective for their intended purpose can be administered to subjects or individuals susceptible to or at risk of disorders caused by aberrant RGS signaling. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or vaccines may each be administered using different modes or different formulations.

The agent or agents to be co-administered depends on the type of condition being treated. For example, when the condition being treated is a disorder caused by aberrant RGS signaling, the additional agent can be an agent useful in the treatment of such disorders. The additional agents to be co-administered can be any of the well-known agents in the art, including, but not limited to, those that are currently in clinical use. The determination of appropriate type and dosage of radiation treatment is also within the skill in the art or can be determined with relative ease.

III. Therapeutic Applications

In some embodiments, the present invention provides compositions and methods for treating or preventing disorders caused by aberrant RGS signaling (e.g., by inhibiting RGS signaling). RGS proteins are involved in a variety of signaling pathways. The RGS inhibitors of embodiments of the present invention find use in the treatment of a wide variety of disorders. Examples include, but are not limited to, a variety of neurological conditions such as depression (e.g., via enhancement of serotonin signaling; Talbot et al., Proc. Natl. Acad. Sci. U.S.A. 2010, 107, 11086-11091; herein incorporated by reference in its entirety), early stage Alzheimer's or Parkinson's diseases (e.g., via enhancement of cholinergic or dopaminergic signaling, respectively), as an adjunct with a GPCR agonist by increasing the potency or selectivity of the drug by accentuating signal transduction through the receptor (e.g., as an useful adjunctive therapy with L dopa or synthetic dopamine agonists in Parkinson's disease), and selective attenuation of opioid signaling in neurons in the pain to selectively increase the analgesic properties of opioids while reducing side effects (e.g., constipation, abuse liability). Thus, in some embodiments, RGS inhibitors serve as GPCR agonist potentiators and to enhance agonist specificity in a cell-type or pathway-specific manner. In some embodiments, RGS inhibitors function to potentiate insulin release (e.g., to treat insulin resistance).

In some embodiments, the compounds described herein (e.g., those described in Tables 2, 5 and 6) and section I above are utilized. In other embodiments, derivatives, mimetics, variants, etc. of the described compounds are utilized.

IV. Drug Screens

In some embodiments of the present invention, the compounds of the present invention, and other potentially useful compounds, are screened for their biological activity (e.g., ability to treat or prevent disorders caused by aberrant RGS signaling). In some embodiments of the present invention, the compounds of the present invention, and other potentially useful compounds, are screened for their ability to inhibit RGS signaling using one of the in vitro or in vivo assays described herein.

In some embodiments, candidate compounds identified using the reporter gene assay are further screened using cellular toxicity assays (e.g., in vitro or in vivo) or in vivo (e.g., in an animal model). In some embodiments, compounds are screened for their ability to cross the BBB (e.g., using assays known in the art).

EXAMPLES

The following examples are provided in order to demonstrate and further illustrate certain preferred embodiments and aspects of the present invention and are not to be construed as limiting the scope thereof.

Example 1

Biochemical Evaluation of Class of Small Molecule RGS inhibitors with Cellular Activity Methods:
Reagents:
Chemicals were purchased from Sigma-Aldrich (St. Louis, Mo.) or Fisher Scientific (Hampton, N.H.) and were reagent grade or better. [$^{32}$P]GTP (10 mCi/mL) and [35S]GTPγS (12.5 mCi/mL) was obtained from Perkin Elmer Life and Analytical Sciences, (Boston, Mass.) and was isotopically diluted before use. Amylose resin was purchased from New England Biolabs (Ipswich, Mass.). Ni-NTA resin was purchased from Qiagen (Valencia, Calif.). Avidin-coated microspheres were purchased from Luminex (Austin, Tex.). CCG-50014 (4-[(4-fluorophenyl)methyl]-2-(4-methylphenyl)-1,2,4-thiadiazolidine-3,5-dione) and analogs were purchased from Fisher Scientific (Waltham, Mass.) from the Maybridge compound collection or were synthesized.

Protein Expression and Purification:
With the exception of RGS8 mutants, all RGS and G proteins were prepared as previously described (Roman, D., et al., Mol Pharmacol). For the RGS8 cysteine serine mutants, site directed mutagenesis was performed using the following primers for 107C (C160S) (Sense: 5'-GCAGGAGCCATC-CCTGACTAGCTTTGACCAAG-3' (SEQ ID NO:1); Antisense: 5'-CGTCCTCGGTAGGGACTGATCGAAACTG-GTTC-3'; (SEQ ID NO:2)), and 160C (C107S) (Sense: 5'-TGGAATTCTGGTTGGCCAGTGAGGAGT-TCAAGAAG-3' (SEQ ID NO:3); Antisense: 5'-ACCTTAA-GACCAACCGGTCACTCCTCAAGTTCTTC-3'; (SEQ ID NO:4)). Mutagenesis was performed using the QuickChange Multi-site Directed Mutagenesis kit (Agilent, La Jolla Calif.). G protein activity was determined by [$_{35}$S]GTPγS binding (Sternweis, P. C. and J. D. Robishaw, Isolation of two proteins with high affinity for guanine nucleotides from membranes of bovine brain. J Biol Chem, 1984. 259(22): p. 13806-13). In all cases, proteins were purified to >90% homogeneity before use.

Chemical Labeling of Purified Gα$_o$ and RGS Proteins:
RGS proteins were biotinylated and Gα$_0$ was labeled with AlexaFluor-532 as previously described (Blazer, L. L., et al., Curr Protoc Cytom. Chapter 13: p. Unit 13 11 1-15).

FCPIA Dose Response and Reversibility Experiments:
FCPIA was performed as previously described using chemically biotinylated RGS proteins and AlexaFluor-532 labeled Gα$_0$. (Roman et al., J Biomol Screen, 2009; Blazer, L. L., et al., Mol Pharmacol).

Single Turnover GTPase Measurements:
Compounds were tested for the ability to inhibit the RGS4 and RGS8-stimulated increase in GTP hydrolysis by Gα$_0$ as described previously (Roman, D. L., et al., Mol Pharmacol, 2007. 71(1): p. 169-75; Roof, R. A., et al., Chem Biol Drug Des, 2006. 67(4): p. 266-74).

Thermal Stability Measurements:
The thermal denaturation of RGS8 and Gα$_o$ was measured using a ThermoFluor Instrument (Johnson & Johnson, Langhorne, Pa.). Protein (5 µM RGS8 or Gα$_o$) was incubated with CCG-50014 or vehicle control for 15 minutes at room temperature in 50 mM HEPES pH 8.2, 500 mM NaCl, 5% glycerol in a volume of 15 µL in a black 384-well PCR microtiter plate (ThermoFisher Cat # TF-0384/K). To this mixture was added 1-anilinonapthalene-8-sulfonic acid to a final concentration of 200 µM. The samples were overlaid with 5 µL of silicone oil and subjected to a temperature ramp using the following parameters: ramp temperature range: 30-90° C.; temperature increment: 1° C.; image collection temperature: 25° C.; temperature holds: 30 seconds for ramp temperature, 15 seconds for image collection temperature. The samples were cooled to 25° C. between temperature increments for image capture to maximize signal:noise. Melting temperatures ($T_m$) were calculated from the data using the sigmoidal fitting procedure in the ThermoFluor++software package (version 1.3.7).

Analyses of the Protein Adduct of RGS by ESI-LC/MS:
The molecular mass of the RGS protein was analyzed by ESI-LC/MS using a LCQ ion-trap mass spectrometer (ThermoScientific, Waltham, Mass.). RGS8 wild-type or mutant proteins were diluted to 2 µM in 50 mM potassium phosphate buffer, pH 7.4 and CCG-50014 or an equivalent volume of DMSO was added to the sample. Following treatment with CCG-50014, an aliquot (~50 µL) of the protein solution was applied to a reverse-phase Zorbax 300-SB C3 column (2.150 mm, 5 µm) (Agilent Technologies, CA). The RGS protein was subjected to high performance liquid chromatography with a binary solvent system consisting of 0.1% TFA in water (Solvent A) and 0.1% TFA in acetonitrile (Solvent B) using the following gradient: 30% B for 5 min., linearly increased to 90% B in 20 min., and held at 90% B for 30 min. The flow rate was 0.25 mL/min. The mass spectrometer was tuned with horse heart cytochrome C and the instrumental settings for the mass spectrometer were: spray voltage, 3.5 kV; capillary temperature, 220° C.; sheath gas flow, 80 (arbitrary units); auxiliary gas flow, 20 (arbitrary units). The molecular masses of the unmodified and inhibitor modified RGS proteins were determined by deconvolution of the apoprotein charge envelopes using the Bio-works software (Thermo Scientific, Waltham, Mass.).

Papain Activity Assay:
Papain (Sigma-Aldrich, St. Louis, Mo.) activity was monitored by the increase in fluorescence caused by the liberation of fluorescein from autoquenched fluorescein-conjugated casein (AnaSpec, San Jose, Calif.). Papain (0.625 U) was diluted into 20 mM sodium acetate pH 6.5, 2 mM EDTA. The enzyme was treated with iodoacetamide, N-ethyl maleimide, CCG-50014, or vehicle control for 30 minutes at room temperature. To this, FITC-casein was added to a final concentration of 250 nM. The reaction was allowed to proceed at room temperature in the dark. At time various points along the reaction, the fluorescence intensity (ex. 485 nm, em. 520 nm) was measured using a Victor II plate reader (Perkin Elmer, Boston, Mass.). As a control, CCG-50014 was tested at pH 6.5 and it retains full inhibitory activity against the RGS4-$G\alpha_o$ PPI in FCPIA.

Docking of CCG-50014 to RGS8:

The energy-based docking software Autodock (ver. 4.0) was used to explore the potential binding sites of CCG-50014 on RGS8. The coordinates of RGS8 were obtained from the Protein Data Bank (PDB ID 21HD). Water and other hetero atoms were removed from the structure prior to docking. The coordinates of the CCG-50014 ligand were built using the ChemBioOffice 2008 software suite (CambridgeSoft, Cambridge, Mass.) and the geometry of CCG-50014 was optimized using the semi-empirical quantum PM3 method included in the ChemBioOffice 2008 software suite. For unbiased docking, the grid box of the RGS was set at 60×60×60 $Å_3$ to encompass the entire RGS protein. The flexible CCG-50014 ligand was docked to the rigid RGS using a Lamarckian Genetic Algorithm (LGA) with the following parameters: mutation rate, 0.02; cross-over rate, 0.8; maximal number of generations, $2.7 \times 10^4$.

Results:
FCPIA Characterization of RGS Inhibitory Activity:

CCG-50014 (FIG. 1) was originally identified as a potential inhibitor of RGS8 and RGS16 in a polyplex high throughput screen to identify inhibitors of the RGS-Gα interaction [4]. This activity was confirmed by analyzing the effect of CCG-50014 on several different RGS proteins with freshly reordered compound using multiplexed FCPIA. CCG-50014 fully inhibited several different RGS proteins including RGS4, 8, 16, and 19, but did not have activity on RGS7 or a mutated form of RGS4 that lacks cysteine residues (FIG. 2A, Table 1). The 30 nM $IC_{50}$ value observed for the inhibition of RGS4 makes CCG-50014 the most potent small molecule RGS inhibitor discovered in experiments conducted during the course of developing some embodiments of the present invention.

TABLE 1

CCG-50014 shows >100 fold specificity for
RGS4 over other RGS proteins in the FCPIA assay.

| RGS | $IC_{50}(\mu M) \pm SEM$ | Hill Slope |
| --- | --- | --- |
| RGS4 wild Type | 0.030 ± 0.006 | −1.53 |
| RGS4 Cys-null Mutant | N/A | N/A |
| RGS8 | 11 ± 2 | −0.57 |
| RGS16 | 3.5 ± 2.4 | −1.33 |
| RGS19 | 0.12 ± 0.02 | −0.61 |
| RGS7 | N/A | N/A |

Data are presented as: mean $IC_{50}$ values ± SEM from at least three independent experiments (for RGS4 and RGS8, n > 28).
N/A: No inhibition below the aqueous solubility limit of the compound.

Figure 2:
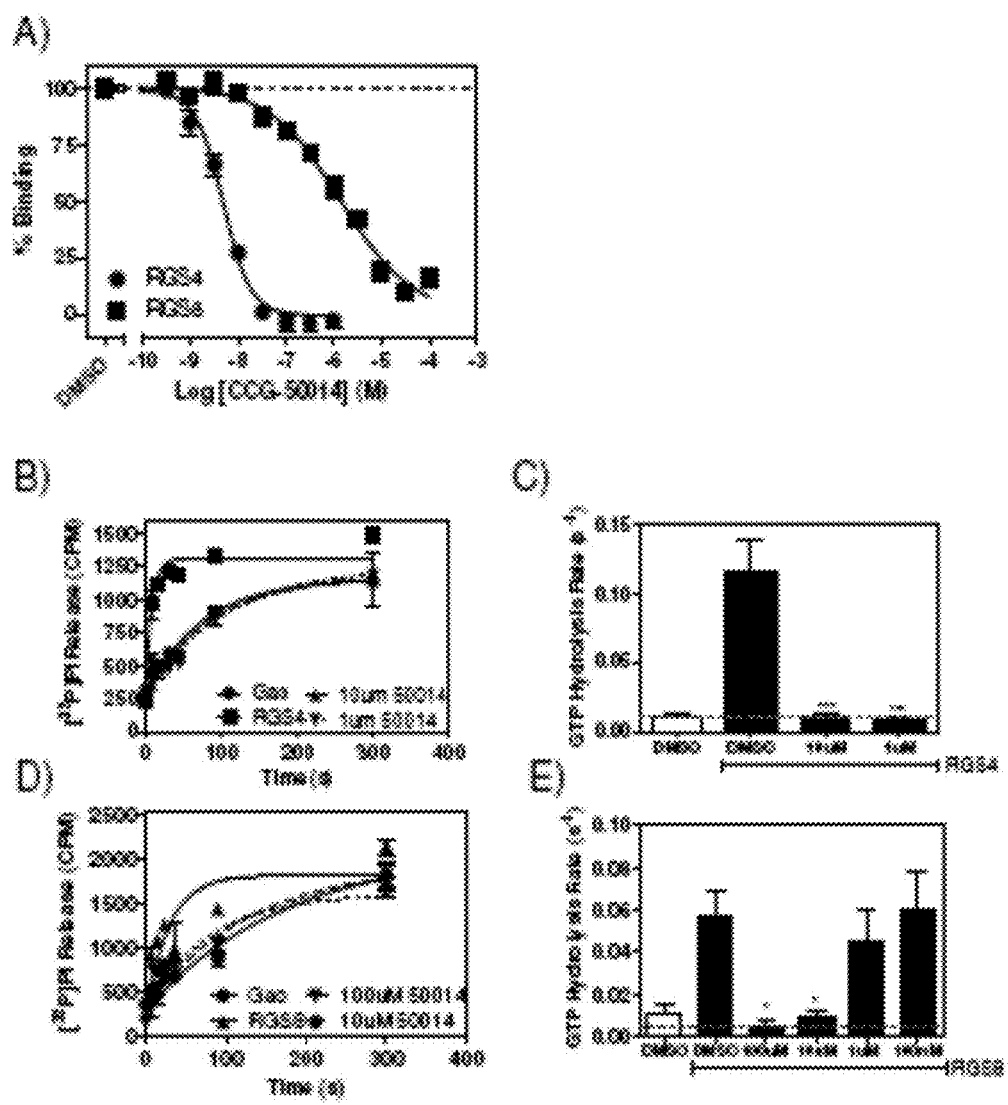
FIG. 2 shows CCG-50014 inhibited RGS4 and RGS8 binding and function. A) CCG-50014 dose-dependently inhibited the binding between aluminum fluoride-activated $G\alpha_o$ and RGS4 or RGS8. Data shown are an average of three independent experiments. The experiment was independently repeated 28 times, producing average $IC_{50}$ values of 30 nM against RGS4 and 1.1 μM against RGS8. B,C) CCG-50014 also inhibits the GAP activity of RGS4 and D,E) RGS8. Using a single-turnover GAP assay, CCG-50014 dose-dependently inhibited the GAP activity of both RGS4 and RGS8. * $P<0.05$, *** $P<0.0001$. All experiments were independently repeated a minimum of three times.
Figure 3:
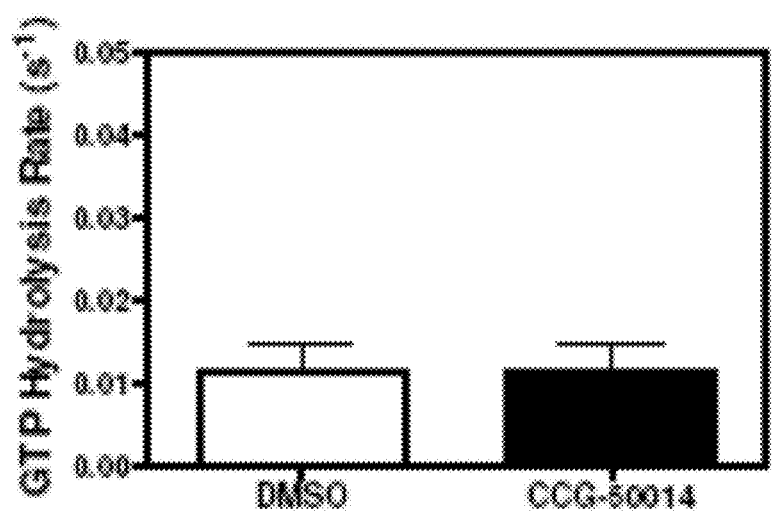
FIG. 3 shows CCG-50014 does not affect the intrinsic rate of GTP hydrolysis by $G\alpha_o$. The rate of GTP hydrolysis as measured using the single turnover GTPase assay was not significantly different in the absence or presence of 100 μM CCG-50014. Data are presented as the average of four independently replicated experiments.

CCG-50014 Inhibits the Catalytic GTPase Accelerating Activity of RGS8 and RGS4:

In a single turnover GAP assay, CCG-50014 inhibited the GAP activity of RGS8 and RGS4 on $G\alpha_o$ (FIG. 2B). Under these assay conditions, RGS8 and RGS4 accelerate the rate of GTP hydrolysis by approximately 5 and 10 fold, respectively. CCG-50014 inhibited that activity of both RGS proteins. At a saturating concentration (100 μM), CCG-50014 did not alter the intrinsic rate of GTP hydrolysis by $G\alpha_o$. While the present invention is not limited to any particular mechanism, and an understanding of the mechanism is not necessary to practice the present invention, it is contemplated that the compound does not act by altering the enzymatic activity of the G protein, at least under single-turnover conditions (FIG. 3).

Figure 4:
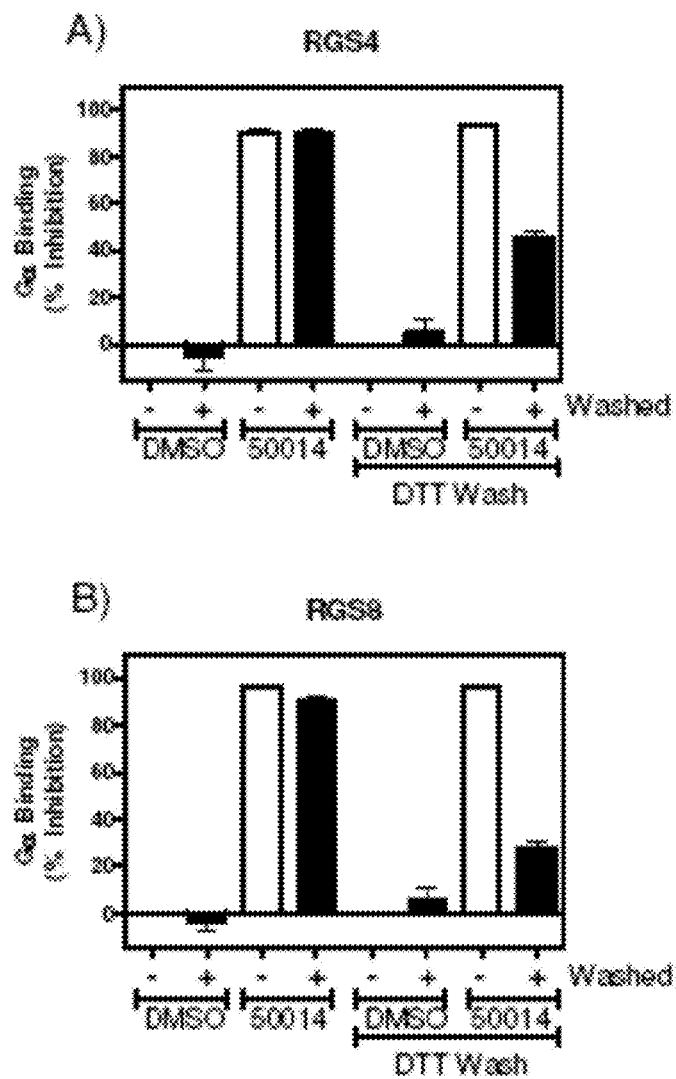
FIG. 4 shows that CCG-50014 is an inhibitor of RGS4 and RGS8 and its effects are partially reversed the thiol reductant DTT. A) RGS4 and B) RGS8 were treated for 15 minutes with 100 μM CCG-50014 prior to vigorous washing to remove any unbound compound. To determine if the compound was reacting in a thiol-sensitive manner, washing was performed in the absence or presence of 1 mM DTT. Data are presented as the mean±SEM from at least three independent experiments.

CCG-50014 Irreversibly Inhibits RGS Proteins:

FCPIA-based reversibility experiments were performed to probe the mechanism of action of the compound (FIG. 4). RGS-coated polystyrene beads were incubated with a saturating concentration (100 μM) of CCG-50014 for 15 minutes before being thoroughly washed by repeated centrifugation and resuspension (theoretical dilution of ~78,000 fold). These beads were then analyzed for $G\alpha_o$ binding by FCPIA. Washing of the beads did not restore $G\alpha_o$ binding activity by the RGS proteins, suggesting that the compound was irreversibly bound to the protein. This inhibition was partially reversed by washing the beads with buffer containing 1 mM dithiothreitol (DTT), suggesting the mechanism of reactivity could be through sulfhydryl modification, a mechanism in common with the previously described RGS inhibitor, CCG-4986 (Roman et al., supra).

Figure 5:
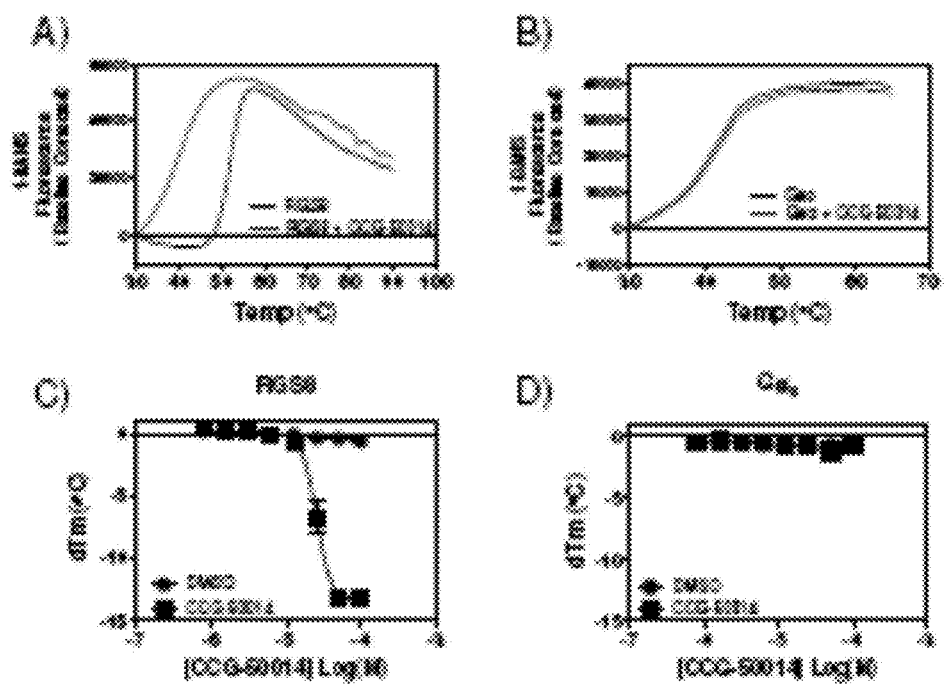
FIG. 5 shows CCG-50014 thermally destabilizes RGS8 in a dose-dependent manner, but has no effect on the thermal stability of $G\alpha_o$. Representative melting traces of A) RGS8 and B) $G\alpha_o$ in the absence and presence of a saturating concentration of CCG-50014. Dose-response curves showing the thermal destabilization effects of CCG-50014 on C) RGS8 and D) $G\alpha_o$. Data are presented as the mean±SEM of three independent experiments.

CCG-50014 Binds to RGS Proteins but not to $G\alpha_o$:

The melting temperature of a protein is often influenced by the binding of small molecules (Lo, M. C., et al., Anal Biochem, 2004. 332(1): p. 153-9; Niesen et al., Nat Protoc, 2007. 2(9): p. 2212-21; Pantoliano, M. W., et al., J Biomol Screen, 2001. 6(6): p. 429-40). Using a ThermoFluor® instrument (Johnson & Johnson, Langhorne, Pa.), the thermal denaturation of RGS8 and $G\alpha_o$ were characterized in the presence and absence of CCG-50014 (FIG. 5). Using this technique, a large, dose-dependent destabilization of RGS8 was observed but no effect on $G\alpha_o$. This indicates that the compound is interacting exclusively with the RGS protein. This result was further confirmed by Liquid Chromatography-Mass Spectral (LCMS) analysis as described below.

Figure 6:
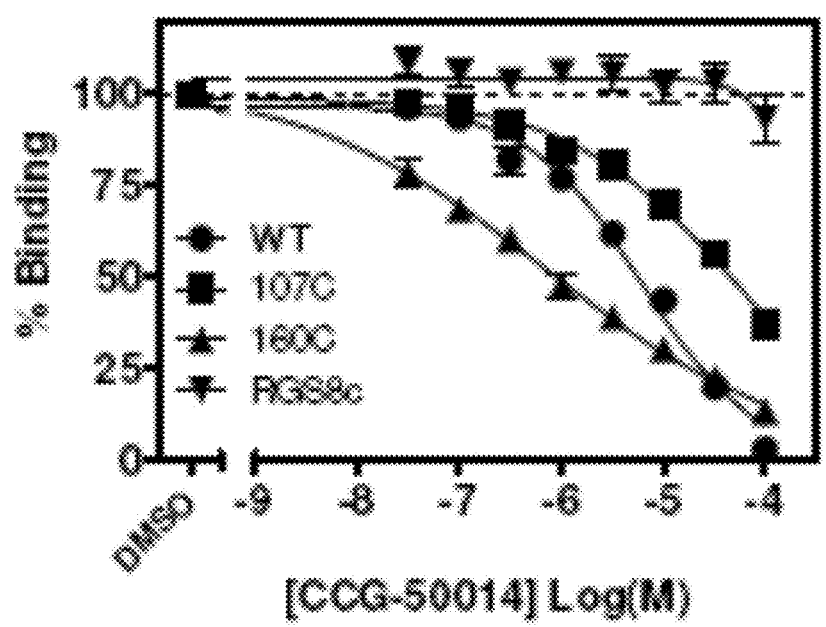
FIG. 6 shows that CCG-50014 requires at least one cysteine residue on RGS8 for full activity. Mutating both cysteines to serine (RGS8c) produced a protein that was completely insensitive to the effect of CCG-50014. The presence of either Cys 107 (107C) or Cys 160 (160C) provided sensitivity to CCG-50014. The inhibition parameters ($IC_{50}$ (μM), Hill Coefficient) for CCG-50014 on these proteins were as follows: wild-type RGS8 (wt): 6.1 μM, −0.79; 107C, 46.5 μM, −0.54; 160C, 0.71 μM, −0.36; Cysteine-null RGS8 (RGS8c): >100 μM. Data are presented as the mean±SEM of three independent experiments.

CCG-50014 Depends on Cysteine Residues to Inhibit the $AlF_4^-$-$G\alpha_o$/RGS Interaction:

To identify the potential cysteine targets of CCG-50014, the compound's effects on RGS8 were studied. This protein only contains two cysteines in the RGS homology domain, making it a simpler model system to study than other RGS proteins. Each cysteine from the RGS8 RGS homology (RH) domain was individually mutated to serine and the activity of the compound was analyzed via FCPIA (FIG. 6). These mutants were named according to the cysteine residue that they maintain (e.g. 107C contains Cys 107 and a serine at position 160). Neither cysteine was fully necessary for function of the compound, but mutating both cysteines reduced the potency of CCG-50014 by >100 fold. An interesting trend was noticed whereby the Hill coefficients for the inhibition of each individual mutant was significantly shallower than that of the wild-type protein, possibly suggesting some form of cooperativity between the two cysteine residues. However, this interpretation is dependent upon the assumptions of the Hill equation, including that the binding has reached equilibrium. In the case of an irreversible inhibitor, clearly this is not the case. Therefore, these data could also be explained by differences in the rate of compound reaction with these two mutants. While the present invention is not limited to any particular mechanism, and an understanding of the mechanism is not necessary to practice the present invention, it is contemplated that the insensitivity of the RGS8 cysteine null mutant corresponds well with the insensitivity of the RGS4 cysteine null mutant (Table 1), suggesting a similar mechanism of action across the two proteins.

Figure 7:
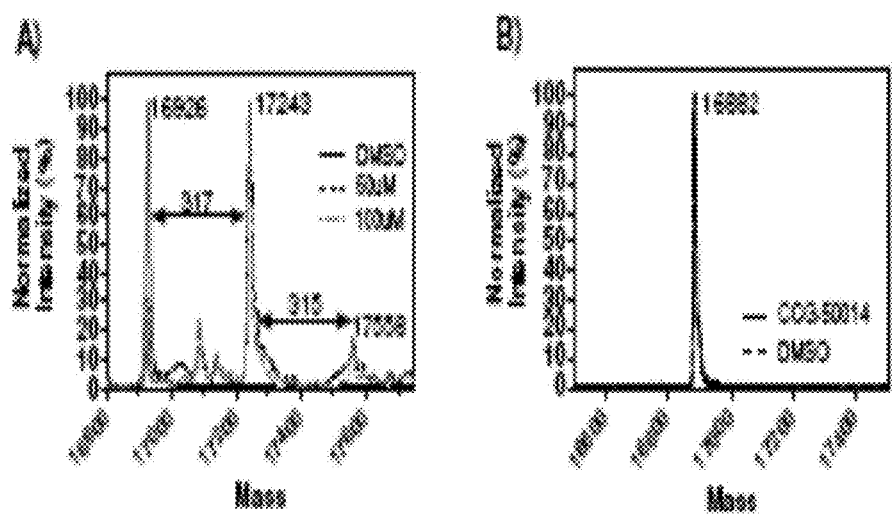
FIG. 7 shows CCG-50014 forms a covalent adduct on RGS8. A) Protein was treated with CCG-50014 before analysis via LC-MS. After treatment with compound a predominant peak appeared with a mass shift of 317 as compared to the vehicle-treated protein, correlating to the addition of a full compound adduct (CCG-50014 MW: 316.4). A second minor peak with an additional mass shift of 315 was observed, which correlates to the addition of two full MW adducts of CCG-50014. B) No adducts are observed on the cysteine-null (C to S) form of RGS8 (RGS8c).
Figure 8:
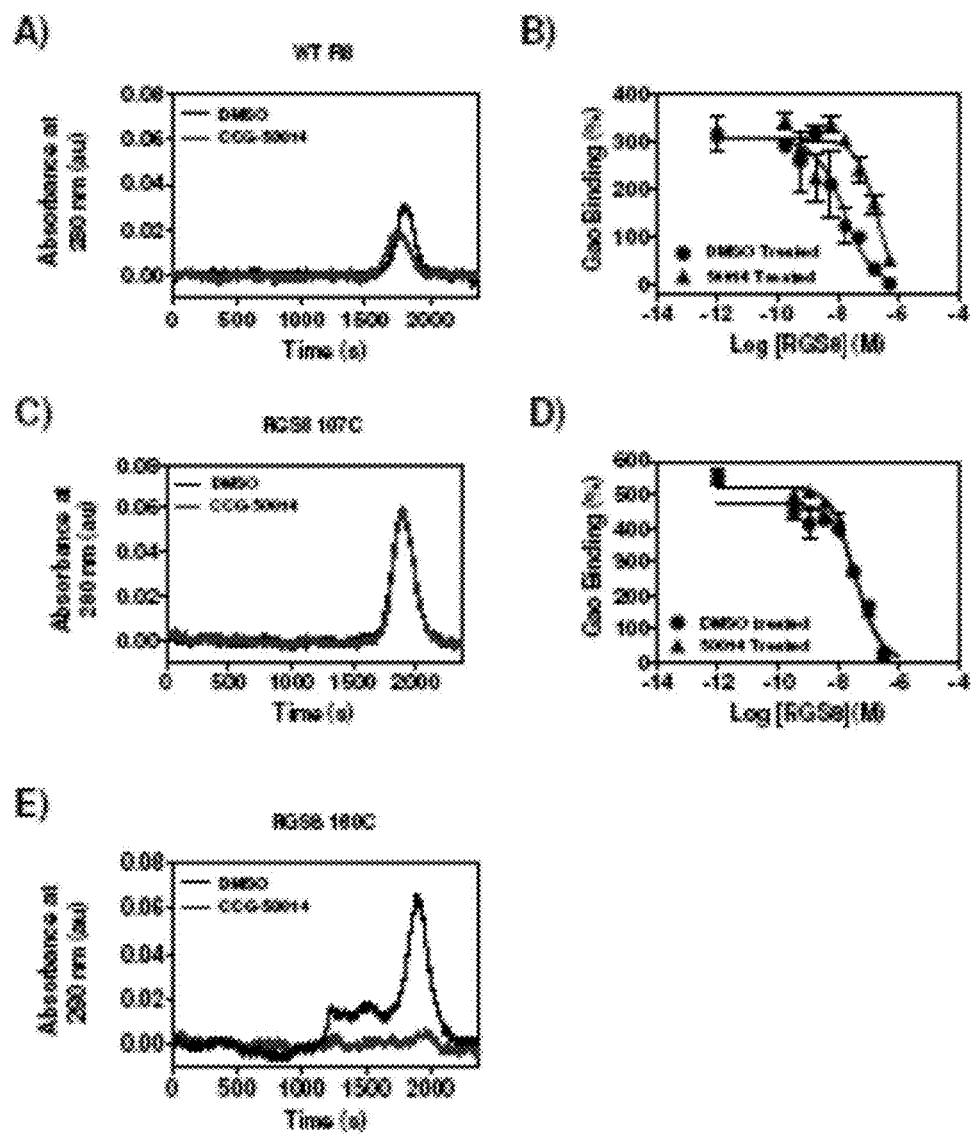
FIG. 8 shows that CCG-50014-induced protein aggregation is dependent on the presence of 160C. A,B) Wild type, C,D) 107C, or E) 160C RGS8 was treated with a 5-fold excess of CCG-50014 before removal of the compound via gel filtration. Shown are representative UV chromatogram traces and data from the corresponding competition experiments to test the activity of the recovered protein. The wild-type RGS8 chromatogram shows a slightly left shifted and suppressed peak after CCG-50014 treatment, which coincides with a 14-fold decrease in protein activity. The 107C mutant protein is completely insensitive to the effects of CCG-50014, while the 160C mutant protein completely (and visually) aggregates upon compound treatment and is removed by the prefiltration of the samples.

CCG-50014 is a Covalent Sulfhydryl Modifier of RGS8:

To test the hypothesis that CCG-50014 covalently modifies RGS proteins, high performance liquid chromatography-mass spectral analysis was conducted on RGS8 samples treated with CCG-50014 (FIG. 7). After compound treatment, there was a peak shift in RGS8 corresponding to a full mass adduct of CCG-50014. At high concentrations of CCG-50014 (100 μM) with wild-type RGS8, a second minor peak corresponding to two full adducts was also observed, suggesting that CCG-50014 at this concentration can react with both cysteine residues in the protein. To confirm that this action was via cysteine reactivity, the mutant RGS8 where the two cysteines in the RH domain were mutated to serine was also analyzed and no adduct was observed (FIG. 7B). RGS8 individual cysteine mutants (107C, 160C) were also tested for covalent adduct formation in MS. A single adduct was observed on 107C, while no adduct was observed on 160C under the conditions tested. The lack of an observable adduct on 160C was of particular interest since this mutant was also irreversibly modified by CCG-50014. Indeed, it was inhibited more potently than the 107C mutant. To further probe this observation, WT RGS8 and the two cysteine mutant proteins were treated with a saturating concentration (100 μM) of CCG-50014 before removal of the compound via gel filtration chromatography (FIG. 8). CCG-50014-treated wild-type RGS8 showed a minor mobility shift compared to vehicle-treated WT RGS8 and showed a 14-fold decrease in its ability to compete for $G\alpha_O$ binding to RGS8 beads. The CCG-50014- and vehicle-treated 107C mutant protein migrated through the column in an identical manner and no discernable difference in $G\alpha_O$ binding was observed. The 160C mutant, however, formed aggregates upon treatment with a saturating concentration of CCG-50014 and no monomeric, soluble protein was recovered from the experiment. This indicates that labeling at Cys 160 causes a dramatic decrease in protein stability. This aggregation accounts for the lack of an observable adduct in the mass spectral experiments, as these aggregates would not migrate on the HPLC as a standard protein peak for MS analysis.

Figure 9:
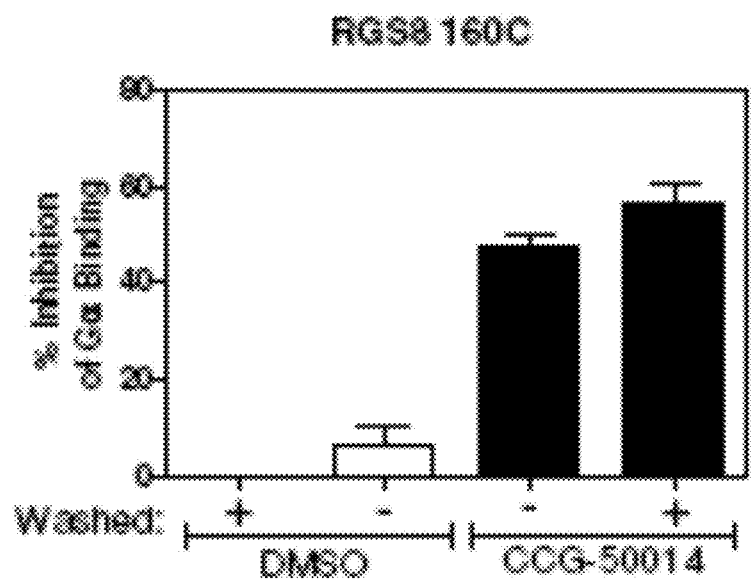
FIG. 9 shows that inhibition of RGS8 is predominantly mediated by Cys 160. Mutant proteins were exposed to 20 µM CCG-50014 and reversibility experiments were performed as in FIG. 4. Data are presented as the mean±SEM from three independent experiments. ***$P<0.0001$ using an unpaired t test.
Figure 9:
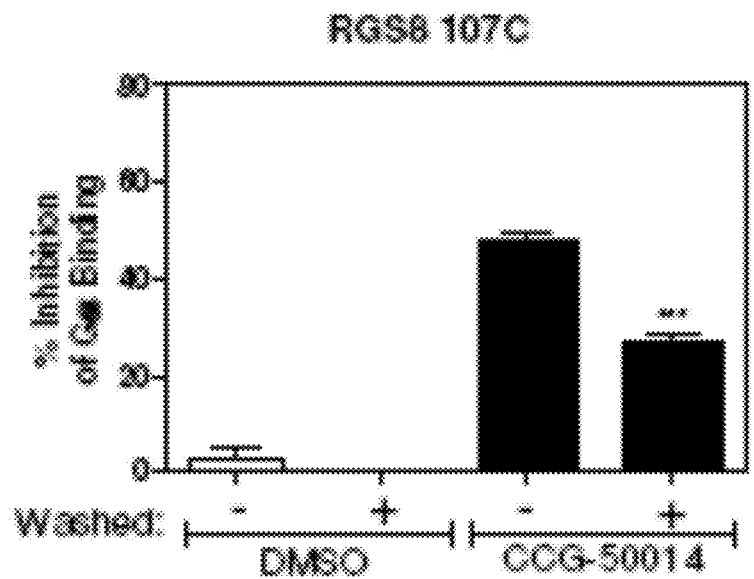

To further probe the mechanism of action of this compound, the development of irreversible inhibition of the RGS8 mutants was studied. Using a standard reversibility experiment (FIG. 9), the effect of CCG-50014 on 160C was completely irreversible, while the effect on 107C could be partially reversed by washing away the compound. These data, along with the gel filtration data show that labeling at Cys 160 causes dramatic destabilization of the protein while labeling at Cys 107 produces inhibition that can be reversed.

Figure 10:
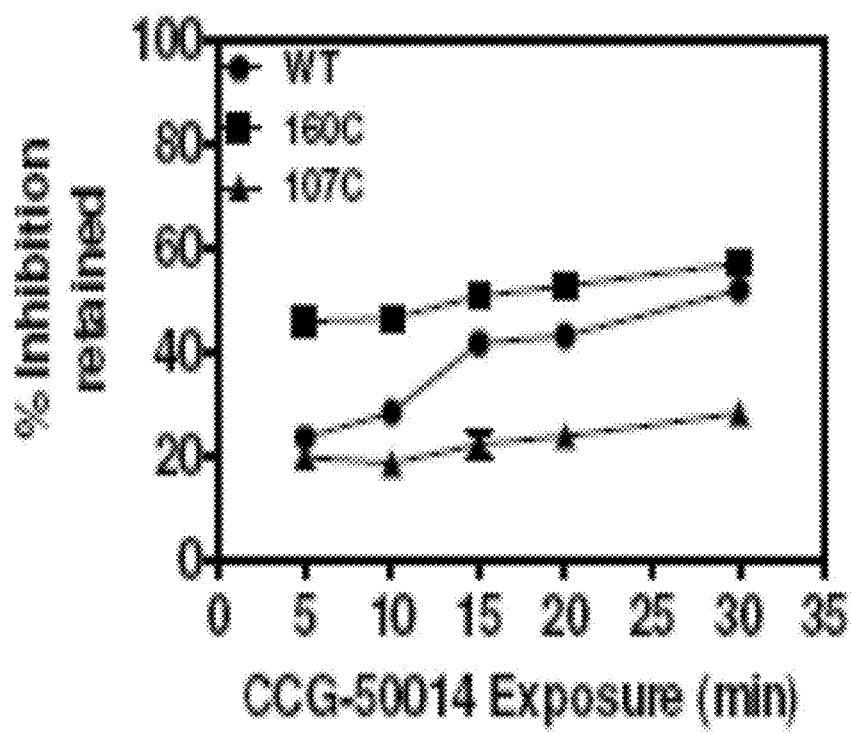
FIG. 10 shows development of inhibition after exposure to CCG-50014 differs between the individual cysteine mutants and provides a means to understand the compound's mechanism of action. Wild-type, 160C or 107C RGS8 was treated with 20 µM CCG-50014 for the desired amount of time before compound removal by extensive washing. The developed amount of inhibition was quantified by comparing the G-protein binding of CCG-50014 treated beads to DMSO treated beads. Data are presented as the mean±SEM from three independent experiments.

Because Cys 160 is buried in the core of RGS8 and Cys 107 is closer to the surface of the protein, it was hypothesized that the compound might interact more rapidly with Cys 107 than Cys 160. Due to the fact that there are differential effects by CCG-50014 (reversible inhibition vs protein aggregation) depending on which cysteine is labeled, this hypothesis was tested using FCPIA reversibility experiments. The experiment was designed to monitor the development of irreversible inhibition on wild-type RGS8 and the two RGS8 mutants by CCG-50014 as a function of time (FIG. 10). Wild-type, 107C, or 160C RGS8 were immobilized on beads and treated for varying periods of time with 20 μM CCG-50014 before extensive washing. The beads were then probed for $G\alpha_O$ binding using FCPIA and compared to RGS-coated beads that had been treated with DMSO alone. At this concentration of CCG-50014, the 107C RGS8 was ~20% irreversibly inhibited and 160C was ~50% irreversibly inhibited at all time points tested, showing that the compound rapidly exerted its effect on the RGS protein. The wild-type protein showed a delayed development of irreversible inhibition, whereby at early time points, the inhibition was ~20% and increased to, but did not exceed, ~50% over 30 minutes. This showed that there is a differential mechanism of action of the compound on the two individual mutants that is combined in the wild type protein. Furthermore, it shows that reaction with Cys 107 is kinetically preferred in the wild type protein.

A potential confounding factor in this analysis is that there is a significant difference in basal melting temperatures between 107C RGS8 (Tm 53.2±0.2) and 160C RGS8 (Tm 42.5±0.1), whereby 160C is dramatically less stable overall. It is possible that labeling of the 160C mutant may have a more exacerbated sensitivity to CCG-50014 than that of the 107C mutant, solely due to 128 the intrinsic instability of this protein. Labeling of the 160C mutant with smaller, less disruptive, analogs CCG-50014 may not always force protein unfolding in the wild-type protein.

Figure 11:
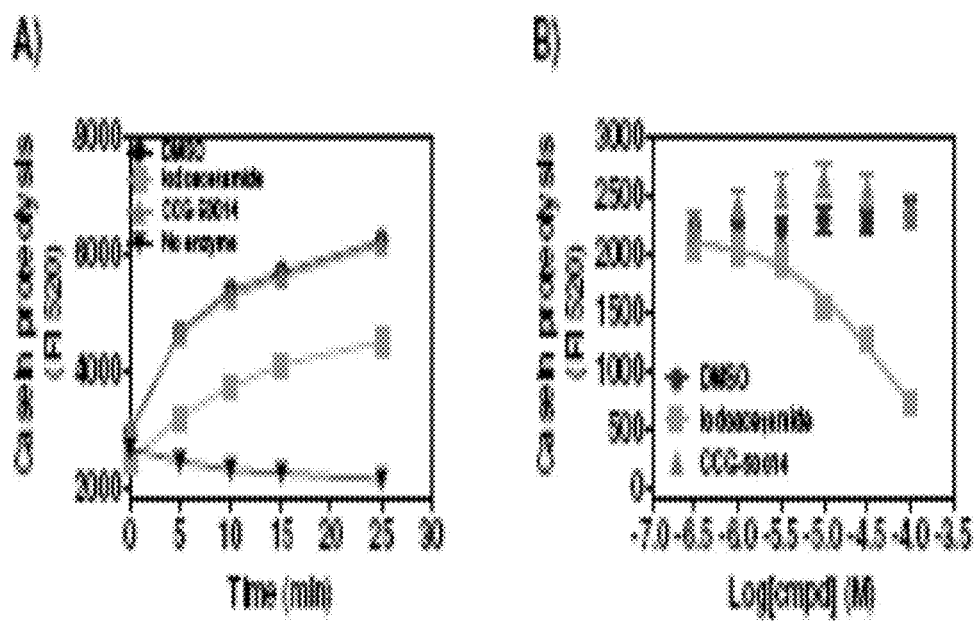
FIG. 11 shows CCG-50014 does not inhibit the general cysteine protease, papain. A) Papain (0.625 U) was mixed with self-quenching FITC-conjugated casein and the liberated fluorescence that results from casein-dependent proteolysis was observed as a function of time in the presence of different cysteine alkylators. Even 100 µM CCG-50014 is incapable of inhibiting casein proteolysis by papain. B) The effect of the cysteine alkylator iodoacetamide on inhibiting papain activity is dose-dependent. CCG-50014 was incapable of inhibiting papain activity. Data are presented as the mean±SEM from three independent experiments.

CCG-50014 is not a General Cysteine Alkylator:

Cysteine reactive compounds might be expected to have more off-target effects than non-reactive compounds. To determine if this compound could bind to and inhibit any reactive cysteine, the ability of CCG-50014 and a known general cysteine alkylator (iodoacetamide) to inhibit a standard cysteine protease was tested (FIG. 11). Iodoacetamide inhibited the proteolytic activity of papain in a dose-dependent manner. However, even at high concentrations (100 μM), CCG-50014 had no effect on papain. This shows that there is at least a basal level of selectivity of this class of compounds for cysteines in the RGS over other 129 reactive cysteines. It is also possible that the compound cannot enter the active site of papain and therefore it would be prudent to extend these studies to a panel of physiologically relevant thiol-dependent processes.

Figure 12:
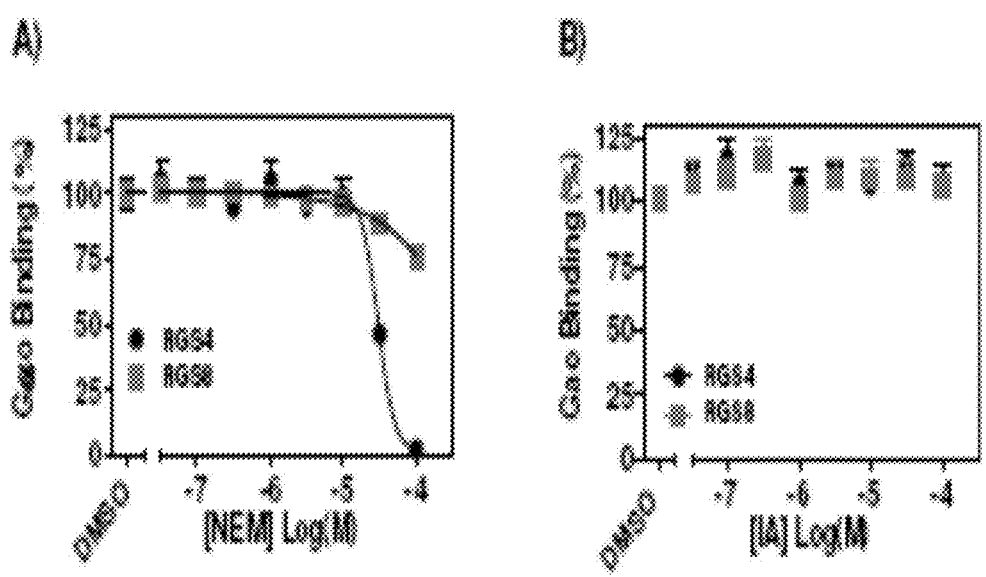
FIG. 12 shows CCG-50014 is a much more potent RGS inhibitor than two general cysteine alkylators N-ethyl maleimide (NEM) and iodoacetamide (IA). Dose response curves for A) NEM and B) IA. The only protein that displayed sensitivity to the alkylators tested was RGS4, which was inhibited by NEM with an $IC_{50}$ value >3.5 Log higher than that of CCG-50014. Data are presented as the mean±SEM from three independent experiments.

General Cysteine Alkylators do not Inhibit RGS Proteins:

The RGS selectivity of CCG-50014 could be explained by RGS proteins being particularly sensitive to thiol modification. To test for this, the RGS inhibitory activity of two general cysteine alkylators, N-ethyl maleimide and iodoacetamide, was analyzed (FIG. 12). Iodoacetamide had no effect on $G\alpha_O$ binding to any of the RGS proteins tested. At high concentrations (IC50: 30 μM), N-ethyl maleimide inhibited RGS4, however it had no effect on RGS8 or papain. These data show that CCG-50014 is more than 3.5 orders of magnitude more potent on RGS4 than either of the general cysteine alkylators tested. This shows that RGS proteins are not particularly sensitive to cysteine modification and the effect observed by CCG-50014 is more than just random thiol alkylation.

Figure 13:
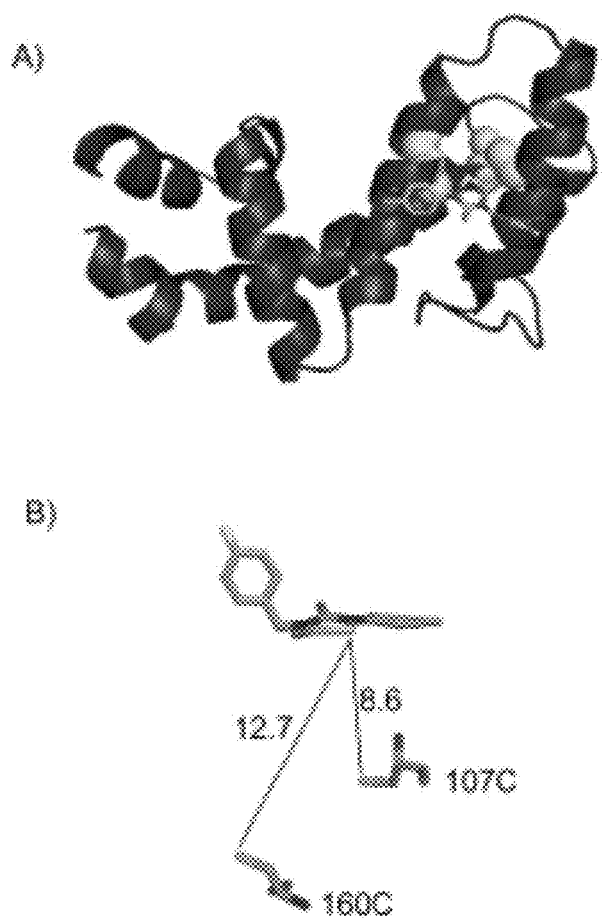
FIG. 13 shows the binding site of CCG-50014 on RGS8. A) This binding site was the most energetically favorable site for docking of CCG-50014 to RSG8, with an estimated Ki of 18 µM. This site is near the analogous "B" site on RGS4, which is important for RGS regulation by calmodulin and acidic phospholipids. B) Assuming a static protein, this binding site places the compound close to the two cysteine residues in RGS8, but not close enough for a covalent reaction to occur at any reasonable rate. A conformational change must occur in the RGS to allow compound intercalation into the helix bundle. Distances are shown in angstroms.
Figure 14:
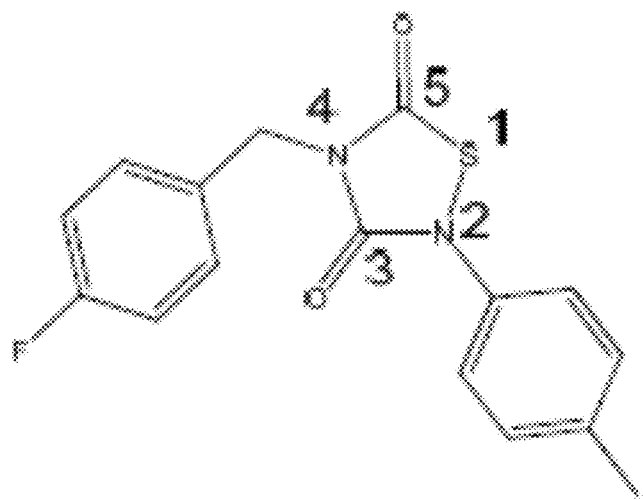
FIG. 14 shows The chemical structure of CCG-50014, (4-[(4-fluorophenyl)methyl]-2-(4-methylphenyl)-1,2,4-thiadiazolidine-3,5-dione)

Computational Modeling of the CCG-50014-RGS8 Interaction:

To identify potential binding sites for CCG-50014 on RGS8, an unbiased molecular docking simulation was performed. CCG-50014 docked preferentially to a site on the RGS that is located near the region of the surface of RGS8 that corresponds to the "B"-site of RGS4 (FIG. 13). The compound docked at this site with a calculated free energy of −6.4 kCal/mol, which translates to an estimated $K_i$ of 18 μM. This affinity is approximately in line with experimentally derived $K_i$ value of 0.3 μM (Table 1). This binding site places the compound a considerable distance from the two cysteine residues known to play a role in the compound's inhibitory activity (FIG. 13B). While the present invention is not limited to any particular mechanism, and an understanding of the mechanism is not necessary to practice the present invention, it is contemplated that it would require a substantial change in the conformation of the protein for the compound to dock at this site and react with a cysteine residue.

Limiting the Reactivity of CCG-50014 Diminishes Potency:

To probe the chemical space around CCG-50014, a series of 76 analogs of CCG-50014 were synthesized and analyzed to identify compounds with optimized physicochemical and pharmacological properties (see Example 2). The first and most prominent trend is that the center heterocycle (the thiadiazolidine dione) is required for function. It is likely to be the site of cysteine thiol reactivity. While the present invention is not limited to any particular mechanism, and an understanding of the mechanism is not necessary to practice the present invention, it is contemplated that the extremely potent $IC_{50}$ value on RGS4 meant that the compound interacted with the protein in a way that was governed by more than simple covalent reactivity. To determine if there was significant non-covalent affinity of this compound, non-reactive, or less reactive analogs of CCG-50014 were synthesized and tested for activity (Table 2). These compounds showed limited, if any, activity in the FCPIA assay, showing that the main mechanism of action of CCG-50014 is through covalent reactivity with one or more cysteine residues on the RGS. However, since this compound is dramatically more potent than two other general cysteine alkylators, a non-covalent docking mechanism at play that drives the affinity of CCG-50014 and analogs for the RGS.

TABLE 2

CCG-50014 analogs with limited reactivity. Data are presented as the mean of two independent FCPIA experiments.

| Compound ID | Structure | Putative Reactivity | RGS4 $IC_{50}$ (μM) | RGS8 $IC_{50}$ (μM) |
| --- | --- | --- | --- | --- |
| CCG-050014 | 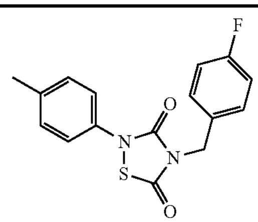 | Reactive | 0.030 | 1.1 |
| CCG-203778 | 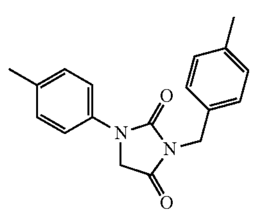 [SMILES: Cc1ccc(CN2C(=O)CN(c3ccc(C)cc3)C2=O)cc1] | Non reactive | >100 | >100 |
| CCG-203779 | 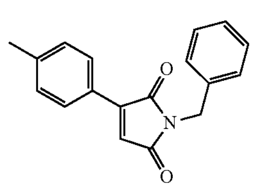 [SMILES: Cc1ccc(C2=CC(=O)N(Cc3ccccc3)C2=O)cc1] | Less reactive | 93 | >100 |
| CCG-203780 | 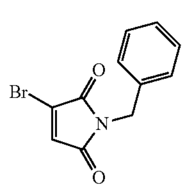 [SMILES: O=C1C=C(Br)C(=O)N1Cc1ccccc1] | Less Reactive | 32 | >100 |

Molecules disrupting the RGS/Gα interaction have significant physiological effects by increasing the magnitude and/or duration of Gα signaling responses. Inhibition of RGS protein activity genetically produces dramatic physiological phenotypes, showing that a small molecule RGS inhibitor might provide similar actions in vivo.

CCG-50014 is the most potent small molecule RGS inhibitor identified in this Example. It inhibits the in vitro interaction between RGS4 and $Gα_o$ with a low nanomolar $IC_{50}$ value. It is nearly 3 orders of magnitude selective for RGS4 over two closely related RGS proteins, RGS8 and RGS16 (FIG. 2, Table 1). CCG-50014 is a covalent modifier of cysteine residues (FIG. 4, FIG. 6, FIG. 7). Its activity in a series of cellular assays indicates feasibility of physiological modulation of RGS activity by small molecules.

CCG-50014 does not inhibit a mutant RGS4 where all cysteine residues in the RH domain were mutated to alanine (Table 1 and Roman et al., J Biomol Screen, 2009). Furthermore, the compound was inactive on RGS7, an RGS protein that naturally has no cysteine residues in its RH domain (Table 1). These two pieces of information indicate that the mechanism of action of CCG-50014 requires at least one cysteine residue—a hallmark of a sulfhydryl-reactive irreversible inhibitor. This hypothesis was confirmed by the FCPIA reversibility experiments (FIG. 4) and subsequent mass spectral analysis of CCG-50014 treated RGS8 (FIG. 7). Based on the chemical structure of the compound and the full molecular weight adduct observed in the LC-MS experiments, the mechanism of reaction of CCG-50014 with a cysteine residue on an RGS protein is by nucleophilic attack of the cysteine thiol onto the sulfur atom of the central heterocycle causing a ring opening event. Consistent with the DTT-induced reversibility of CCG-50014 inhibition (FIG. 4), this newly formed disulfide is sensitive to reductants.

CCG-50014 interacts with cysteine residues in RGS8 that are not near the Gα interaction interface (FIG. 13), indicating an allosteric mechanism of action. Unbiased computational modeling predicts that CCG-50014 could non-covalently bind to a site on RGS8 that is near to the acidic phospholipid binding site on RGS4. Binding in this site would place the reactive group of CCG-50014 within 8-13 Å of the two cysteines in the RGS8 RH domain. While at this distance it is unlikely that a covalent bond could be formed, it is considered that the compound may initially bind to this pocket and a subsequent conformational change in the protein provides access to the cysteine thiol. This conformational change is the fundamental mechanism by which the allosteric modulation of G protein binding activity is conferred.

The differential sensitivities of the cysteine mutants to CCG-50014 are also explained by this binding modality. The decreased activity and increased reversibility of CCG-50014 on 107C RGS8 (FIGS. 6, 8, 9) is in accord with the fact that Cys 107 is more solvent accessible and is closer to the hypothesized binding site of the compound. Compound reacting with Cys 160 causes drastic protein unfolding (FIG. 9), which also fits with this model.

While the present invention is not limited to any particular mechanism, and an understanding of the mechanism is not necessary to practice the present invention, it is contemplated that RGS inhibition by CCG-50014 occurs when the compound originally binds to a surface equivalent to the "B" site on RGS4 in a manner that does not produce an inhibitory effect. This interaction provides enough interaction energy to keep the compound in close proximity to the protein long enough for the RGS to enter a cysteine-exposed conformation. Assuming that the compound binding site is as modeled (FIG. 13), the first cysteine to become exposed to the compound is Cys 107. Upon reacting with this cysteine, CCG-50014 can trap the RGS in a conformation that is incapable of binding to Gα. Reversal of this reaction is possible, leading to reactivation of the RGS. If the compound interacts with the more deeply buried cysteine, Cys 160, it causes a dramatic disruption of the hydrophobic core of the protein, leading to protein denaturation. This is shown by the gel filtration data (FIG. 8). Cys 107 is labeled more rapidly than Cys 160 in the wild type protein (FIG. 10). These data are consistent with the hypothesis that the compound initially interacts with Cys 107 to form a weak, DTT- or time/dilution-reversible inhibition of RGS activity. Then, either the Cys 107-bound compound transfers to Cys 160 or a second CCG-50014 molecule binds to Cys 160 to produce the completely irreversible reaction observed the gel filtration experiments (FIG. 8). While the present invention is not limited to any particular mechanism, and an understanding of the mechanism is not necessary to practice the present invention, it is contemplated that the irreversible inhibition after labeling of Cys 160 is due to a massive destabilization of the hydrophobic core of the RH domain that would occur by the intercalation of CCG-50014.

Selectivity is a significant issue when studying reactive compounds. A series of experiments was conducted to determine if CCG-50014 is a just a general, non-specific cysteine alkylator, or if it has some intrinsic selectivity for RGS proteins. CCG-50014 does not inhibit the activity of the cysteine protease papain at concentrations over 3000 times higher than that required for RGS inhibition (FIG. 11). In contrast, the cysteine alkylator iodoacetamide dose-dependently inhibited the activity of this protease but had no effect on RGS4. Furthermore, the cellular activity observed (Example 2), also indicates that these compounds do not dramatically affect a large number of cellular processes.

CCG-50014 irreversibly inhibits RGS4 with nanomolar potency and the mechanism of this inhibition is predominantly through reacting with cysteine residues at an allosteric site on the RGS. This compound and related analogs are also examples of RGS inhibitors that are active in living cells.

Example 2

Cellular and Structure-Activity Studies of the CCG-50014 Compound Class

This Example describes experiments in which the effects of CCG-50014 and related analogs were analyzed for RGS4/Gα$_o$ activity in cellular assays. It is shown herein that CCG-50014 and related analogs are able to inhibit the RGS4/Gα$_o$ PPI in living cells and to potentiate signaling through the δ opioid receptor and the M3 muscarinic receptor.

Materials and Methods:
Reagents and Compounds:
Reagents were purchased from Sigma-Aldrich (St. Louis, Mo.) or Fisher Scientific (Hampton, N.H.) and were reagent grade or better. Avidin-coated microspheres were purchased from Luminex (Austin, Tex.). CCG-50014 (4-[(4-fluorophenyl)methyl]-2-(4-methylphenyl)-1,2,4-thiadiazolidine-3,5-dione) and analogs were purchased from Thermo-Fisher (Waltham, Mass.) from the Maybridge compound collection or were synthesized.

Protein Expression, Purification, and Labeling:
All RGS and G proteins were prepared as previously described (Roman, D., et al., Pharmacol). G protein activity was determined by [$^{35}$S]GTP γS binding [3]. In all cases, proteins were purified to >90% homogeneity before use. RGS proteins were biotinylated and Gα$_o$ was labeled with AlexaFluor-532 as previously described (Blazer, L. L., et al., Curr Protoc Cytom. Chapter 13: p. Unit 13 11 1-15).

FCPIA Dose Response Experiments:
FCPIA was performed as previously described using chemicallybiotinylated RGS proteins and AlexaFluor-532 labeled Gα$_o$. (Blazer, L. L., et al., Mol Pharmacol; Roman et al., J Biomol Screen, 2009).

Single Turnover GTPase Measurements:
Compounds were tested for the ability to inhibit the RGS4 and RGS8-stimulated increase in GTP hydrolysis by Gα$_o$ as previously described (Roman, D. L., et al., Mol Pharmacol, 2007. 71(1): p. 169-75; Roof, R. A., et al., Chem Biol Drug Des, 2006. 67(4): p. 266-74).

Solubility Experiments:
Compounds were diluted to 100 mM in DMSO and the further diluted to 500 µM in H$_2$O, vortexed and centrifuged for 10 minutes at 13,000×g at ambient temperature. Solubility was quantified by visual inspection of pellet formation on a scale from 0-5, with 0 being no pellet and 5 being a pellet of the same size as that of CCG-50014. Since the key metric was improved solubility, in the rare instance that a compound was deemed to be more insoluble than CCG-50014, it was given a value of 5.

WST-1 Cell Viability Studies:
HEK-293 cells were plated to a density of 30,000/well in 96-well plates and grown for 48 hours in Dulbecco's Modified Eagle Medium (DMEM) containing 10% fetal bovine serum and Penicillin (100 units/ml)-Streptomycin (100 µg/ml) under 5% CO$_2$ at 37° C. Compound treatment was performed overnight in DMEM containing 0.1% bovine serum albumin under 5% CO$_2$ at 37° C. After compound incubation ten microliters of the WST-1 reagent (Hoffmann-La Roche, Switzerland) was added to every well and the cells were incubated for 1 hour under 5% CO$_2$ at 37° C. Absorbance was measured at 450 nm using a Victor II plate reader (Perkin-Elmer, Picastaway, N.J.).

Cellular Localization Studies:
HEK-293T cells grown to 80-90% confluency in 6-well dishes in DMEM supplemented with 10% fetal bovine serum and Penicillin (100 units/ml)-Streptomycin (100 µg/ml) under 5% CO$_2$ at 37° C. RGS and Gα$_o$ expression was induced by transient co-transfection with either 250 ng of full-length human RGS4 with an N-terminal GFP tag (RGS4pEGFP-C1) or a C-terminal RGS4-GFP (RGS4pDEST47) and 250 ng of pcDNA3.1 or pcDNA with wildtype human Gα$_o$. Cells were split onto poly-D-lysine coated glass coverslips and cultured for 24-48 hours after transfection before live cell imaging. Images were acquired on an Olympus Fluoview 500 confocal microscope with a 60×1.40 numerical aperture (N.A) oil objective. Images were obtained by taking a series of stacks every 0.5 µm through the cell and combining the images into a composite stack. The light source for the fluorescent studies was a 488 nm laser with a 505-525 nm bandpass filter. Images were quantified using NIH ImageJ software version 1.43r.

Calcium Mobilization Experiments:
A stable cell line was developed based upon the HEK-293 Flp-In TREx cell line (Invitrogen, Carlsbad, Calif.) that stably express the muscarinic M3 receptor and have human RGS4 expression under doxycycline control. Cells were maintained in DMEM supplemented with 10% fetal bovine serum and Penicillin (100 units/ml)-Streptomycin (100 µg/ml) under 5% CO2 at 37° C. For experiments, cells were split into 96-well black, clear bottom, poly-D-lysine coated microtiter plates (Nunc, Cat. #152037) at a density of 20,000 cells/well in DMEM containing 10% fetal bovine serum and Penicillin (100 units/ml), Streptomycin (100 µg/ml). RGS4 expression was induced by supplementing the medium with 1 µg/mL doxycycline for 24-48 hours before experimentation. Cells were loaded with Fluo-4 No Wash dye in buffer for 30 minutes at 37° C. Compounds and/or carbachol were added to the wells and the fluorescence intensity was measured using a FlexStation (Molecular Devices, Sunnyvale, Calif.) plate reader. Data analysis was performed by calculating the area under the curve or maximal fluorescence intensity from a 120 second kinetic measurement.

cAMP Accumulation:

SH-SY5Y cells were grown in DMEM containing 10% fetal bovine serum and Penicillin (100 units/ml)-Streptomycin (100 μg/ml) under 5% $CO_2$ at 37° C. Cells were plated into 24-well plates to reach ~90% confluency on the day of assay and washed once with fresh serum-free medium, then the medium was replaced with 1 mM IBMX (3-isobutyl-1-methylxanthine) in serum-free medium for 15 min at 37° C., and changed to the medium containing 1 mM IBMX, 30 μM forskolin, and 100 nM of either morphine or SNC80 with or without compound CCG-50014 for 5 min at 37° C. Reactions were stopped by replacing the medium with ice-cold 3% perchloric acid and samples were kept at 4° C. for at least 30 min. An aliquot (0.4 ml) from each sample was removed, neutralized with 0.08 ml of 2.5 M $KHCO_3$, vortexed, and centrifuged at 15,000×g for 1 min to pellet the precipitates. Accumulated cAMP was measured by radioimmunoassay in a 10-15 μl aliquot of the supernatant from each sample following the manufacturer's instructions (cAMP radioimmunoassay kit from GE Healthcare, Piscataway, N.J.). Data are from four separate experiments, each carried out in duplicates and calculated as percent inhibition. The basal cAMP accumulation with forskolin alone with or without compound CCG-50014 did not differ.

Results:

Structure Activity Relationship Studies of the CCG-50014 Family of Compounds:

Biochemical Optimization:

To explore the chemical space around the thiadiazolidine scaffold a series of 76 analogs of CCG-50014 was analyzed using a variety of cellular and biochemical experiments (Table 3). As a primary screening methodology, a RGS4/RGS8 duplex FCPIA assay was performed to obtain biochemical $IC_{50}$ values for the inhibition of $G\alpha_o$ binding to both proteins. Secondary screening was performed to assess compound solubility and the ability to induce a calcium transient in HEK cells, an off-target effect that was originally observed with the lead compound CCG-50014. The primary goals of the SAR studies were to optimize compound solubility and potency and to minimize off target effects. A secondary goal of this study was to determine if it was possible to remove or minimize the reactivity of this scaffold and still retain RGS inhibitory activity.

The majority of the analogs of CCG-50014 that were tested contain the thiadiazolidinedione core structure with varied substituents at the 2 and 4 positions. Because CCG-50014 is only modestly soluble in aqueous solutions, it was desirable to identify active compounds with improved solubility for use in cellular and whole-animal studies. Compound solubility was assessed on a 0-5 scale with 5 being as insoluble as the lead compound, CCG-50014 (solubility ~100 μM in aqueous) and 0 being completely soluble at 500 μM in double-distilled $H_2O$. As expected, it was found that the key determinant of compound solubility was size, whereby large hydrophobic substituents lead to more insoluble compounds. A number of compounds were identified that were much more soluble than CCG-50014 that retained similar potency for RGS4 inhibition (e.g. CCG-203759, CCG-203769).

To identify a pharmacophore for the CCG-50014 class of compounds, all of the compounds were ranked in order of potency on RGS4 (Table 3). No clear trends emerged. Data were further probed for compounds that possessed increased selectivity for RGS4 over RGS8 (Table 4). This analysis showed that small alkyl groups at the R1/R2 positions provide the greatest RGS4/RGS8 selectivity. However, there are several compounds with phenyl-containing sidechains that show >1000 fold selectivity (e.g. CCG-203742). These compounds all contain a —$CH_3$-Ph-p-Me (or in one instance a —$CH_3$-Ph-p-OMe, CCG-203705) at the R2 position, a moiety that appears to confer selectivity regardless of group at the R1 position. This shows that this region of the molecule is important for discriminating between RGS proteins. The most significant result from the SAR analysis was the dependence of the thiadiazolidinedione for activity (see Example 1, Table 2), whereby compounds that did not contain this reactive center lost substantial (>1000 fold) potency against RGS4.

TABLE 3

Structure Activity Relationships of CCG-50014 family. All FCPIA $IC_{50}$ and calcium transient values presented are an average from two independent experiments. The calcium transient data are presented as the effect observed by 10 μM compound expressesed as a percentange of the effect observed by 10 μM CCG-50014.

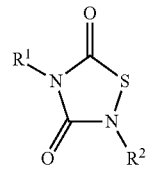

| CCG # | R1 | R2 | Solubility Scale (1-5) | Stock Form | Calcium transient (% 50014) | RGS4 $IC_{50}$ (μM) | RGS4 Hill Slope | RGS8 $IC_{50}$ (μM) | RGS8 Hill Slope | Fold Selectivity (R8/R4) |
|---|---|---|---|---|---|---|---|---|---|---|
| 203731 | $CH_3$—Ph-p-Cl | Ph-p-Me | 5 | Solid | −2.6 | 0.005 | −0.70 | 11.8 | −1.50 | 2360 |
| 203734 | $CH_3$—Ph | $CH_3$—Ph-p-Me | 5 | Solid | 591.3 | 0.007 | −0.84 | 20.4 | −0.66 | 2914 |
| 203732 | $CH_3$—Ph-p-Me | Ph | 3 | Solid | 12.2 | 0.009 | −1.50 | 8.3 | −0.87 | 922 |
| 203736 | $CH_3$—Ph-p-Me | Ph-p-Me | 4 | Solid | 4.9 | 0.009 | −1.35 | 11.6 | −1.45 | 1289 |
| 203735 | $CH_3$—Ph-p-F | Ph-p-OMe | 4 | Solid | 6.2 | 0.011 | −1.33 | 11.4 | −1.27 | 1036 |
| 203741 | $CH_3$—Ph-p, m-Cl | Ph-p-OMe | 3 | Solid | 202.4 | 0.013 | −0.86 | 5.9 | −0.64 | 454 |
| 203742 | $CH_3$—Ph-p-F | $CH_3$—Ph-p-Me | 5 | Solid | 108.5 | 0.013 | −1.19 | 39.8 | −0.22 | 3062 |
| 203724 | $CH_3$—Ph | Ph-p-Me | 5 | Solid | 176.8 | 0.014 | −3.63 | 7.5 | −0.94 | 536 |
| 203727 | $CH_3$—Ph-p-F | Ph-p-Cl | 5 | Solid | 158.5 | 0.014 | −1.66 | 7.6 | −1.06 | 543 |

TABLE 3-continued

Structure Activity Relationships of CCG-50014 family. All FCPIA $IC_{50}$ and calcium transient values presented are an average from two independent experiments. The calcium transient data are presented as the effect observed by 10 μM compound expressesed as a percentange of the effect observed by 10 μM CCG-50014.

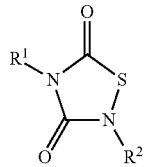

| CCG # | R1 | R2 | Solubility Scale (1-5) | Stock Form | Calcium transient (% 50014) | RGS4 $IC_{50}$ (μM) | RGS4 Hill Slope | RGS8 $IC_{50}$ (μM) | RGS8 Hill Slope | Fold Selectivity (R8/R4) |
|---|---|---|---|---|---|---|---|---|---|---|
| 203761 | iBu | Ph-p-Me | 4 | Solid | 98.9 | 0.014 | −1.47 | 7.7 | −0.92 | 550 |
| 203769 | Bu | Et | 0 | Oil | 2.7 | 0.014 | −0.71 | 83.5 | −0.56 | 5964 |
| 203781 | $CH_3$—Ph-m-Me | Ph | 3 | Solid | 242.8 | 0.015 | −1.65 | 8.4 | −1.17 | 560 |
| 203726 | $CH_3$—Ph-p-F | Ph | 2 | Solid | 20.9 | 0.016 | −1.42 | 6.2 | −0.82 | 388 |
| 203765 | $CH_3$—Ph-p-F | Bu | 3 | Solid | 183.8 | 0.016 | −0.81 | 31.6 | −0.59 | 1975 |
| 203733 | $CH_3$—Ph-p-Me | Ph-p-Cl | 5 | Solid | 20.0 | 0.017 | −1.59 | 12.8 | −1.17 | 753 |
| 203777 | $CH_3$—Ph-m-Cl | Ph-p-Me | 1 | Solid | 179.2 | 0.017 | −0.96 | 17.5 | −1.00 | 1029 |
| 203759 | Me | Ph-p-Me | 0 | Solid | 238.20 | 0.019 | −1.56 | 8.4 | −1.06 | 442 |
| 203767 | Bu | Ph-p-Me | 1 | Solid | 123.0 | 0.020 | −1.46 | 9.5 | −0.96 | 475 |
| 203757 | Bu | Me | 0 | Oil | 138.3 | 0.023 | −1.01 | 28.4 | −1.10 | 1235 |
| 203722 | $CH_3$—Ph | Ph | 1 | Solid | 3.8 | 0.024 | −1.89 | 5.6 | −0.80 | 233 |
| 203739 | $CH_3$—Ph-p, m-Cl | Ph | 3 | Solid | 47.6 | 0.024 | −0.96 | 7.5 | −0.80 | 313 |
| 203746 | $CH_3$—Ph | Ph-p-OMe | 3 | Solid | 74.6 | 0.024 | −1.45 | 12.3 | −1.00 | 513 |
| 203730 | $CH_3$—Ph-p-Cl | Ph-p-Cl | 5 | Solid | 141.3 | 0.026 | −1.48 | 12.7 | −1.36 | 488 |
| 203762 | iBu | Et | 0 | Oil | 38.3 | 0.026 | −0.87 | 70.6 | −0.78 | 2715 |
| 203760 | Me | tBu | 0 | Solid | 47.2 | 0.028 | −0.99 | 56.0 | −0.89 | 2000 |
| 203723 | $CH_3$—Ph | Ph-p-Cl | 3 | Solid | 119.8 | 0.029 | −1.99 | 5.2 | −0.80 | 179 |
| 203763 | iBu | tBu | 0 | Oil | 73.5 | 0.029 | −0.85 | 193.7 | −0.52 | 6679 |
| 203770 | Bu | Bu | 0 | Oil | 188.2 | 0.030 | −0.83 | 122.3 | −0.53 | 4077 |
| 203783 | $CH_3$—Ph-m-Cl | Ph | 5 | Solid | 57.7 | 0.031 | −1.41 | 9.4 | −1.47 | 303 |
| 203773 | $CH_3$—Ph | Ph-m-Cl | 4 | Solid | 198.9 | 0.033 | −1.25 | 10.9 | −0.87 | 330 |
| 203738 | $CH_3$—Ph-p-Me | $CH_3$—Ph-p-Me | 5 | Solid | 251.4 | 0.033 | −0.92 | 94.7 | −0.51 | 2870 |
| 203745 | $CH_3$—Ph-p-OMe | Ph | 4 | Solid | 18.6 | 0.034 | −1.78 | 7.2 | −0.77 | 212 |
| 203743 | $CH_3$—Ph-m, p-Cl | Ph-p-Me | 3 | Solid | 45.6 | 0.034 | −1.43 | 15.7 | −0.65 | 462 |
| 203755 | $CH_3$—Ph-p-OMe | Ph-p-OMe | 2 | Solid | 54.9 | 0.035 | −1.27 | 17.6 | −0.81 | 503 |
| 203728 | $CH_3$—Ph-p-F | Ph-m, p-Cl | 5 | Solid | 127.6 | 0.036 | −1.15 | 17.2 | −1.78 | 478 |
| 203785 | $CH_3$—Ph | Ph-m-Me | 2 | Solid | 144.6 | 0.038 | −1.13 | 21.3 | −0.73 | 561 |
| 203764 | iBu | Bu | 1 | Oil | 141.6 | 0.039 | −0.87 | 98.0 | −0.44 | 2513 |
| 203771 | $CH_3$—Ph | Ph-p-tBu | 4 | Solid | 123.1 | 0.044 | −1.79 | 17.4 | −0.78 | 395 |
| 203794 | $CH_3$—Ph-m-Me | Ph-m-Me | 3 | Solid | 63.3 | 0.046 | −1.79 | 10.4 | −0.82 | 226 |
| 203776 | $CH_3$—Ph-p-F | Ph-m-Cl | 4 | Solid | 222.9 | 0.052 | −1.08 | 12.8 | −1.07 | 246 |
| 203768 | Bu | tBu | 0 | Oil | 91.7 | 0.054 | −3.18 | 119.0 | −0.70 | 2204 |
| 203772 | $CH_3$—Ph | Ph-m-$MeF_3$ | 3 | Solid | 164.8 | 0.057 | −1.43 | 16.4 | −1.15 | 288 |
| 203786 | $CH_3$—Ph-m-Cl | Ph-m-Me | 3 | Solid | 141.6 | 0.064 | −1.52 | 10.1 | −0.95 | 158 |
| 203740 | $CH_3$—Ph-m, p-Cl | Ph-p-Cl | 3 | Solid | −0.1 | 0.068 | −1.31 | 16.7 | −0.76 | 246 |
| 203750 | $CH_3$—Ph-p-OMe | Ph-p-Cl | 3 | Solid | 84.6 | 0.069 | −3.26 | 9.9 | −0.73 | 143 |
| 203747 | $CH_3$—Ph-p-Cl | $CH_3$—Ph-p-Me | 5 | Solid | 11.4 | 0.073 | −1.23 | 336.6 | −0.60 | 4611 |
| 203775 | $CH_3$—Ph-p-F | Ph-m-$MeF_3$ | 2 | Solid | 170.1 | 0.079 | −0.88 | 16.2 | −1.14 | 205 |
| 203748 | $CH_3$—Ph-p-OMe | Ph-m, p-Cl | 2 | Solid | 63.4 | 0.087 | −1.04 | 36.0 | −1.50 | 414 |
| 203725 | $CH_3$—Ph | Ph-m, p-Cl | 2 | Solid | 64.2 | 0.089 | −2.06 | 13.2 | −1.62 | 148 |
| 203756 | $CH_3$—Ph-p-OMe | $CH_3$—Ph-p-Me | 4 | Solid | 169.0 | 0.103 | −2.42 | 92.9 | −0.64 | 902 |
| 203753 | $CH_3$—Ph-m, p-Cl | $CH_3$—Ph-p-Me | 2 | Solid | 51.7 | 0.113 | −1.33 | 109.1 | −0.71 | 965 |
| 203788 | Ph-m-Me | Ph-m-Me | 3 | Solid | 134.0 | 0.121 | −1.91 | 7.1 | −1.09 | 59 |
| 203797 | $CH_3$—Ph-p-F | Ph-p-$N(CH_3)_2$ | 5 | Oil | 111.2 | 0.146 | −1.65 | 10.3 | −1.28 | 71 |
| 203749 | $CH_3$—Ph-m, p-Cl | Ph-m, p-Cl | 5 | Solid | 49.6 | 0.155 | −0.87 | 125.0 | −0.85 | 806 |
| 203752 | $CH_3$—Ph-p-Cl | Ph-p-OMe | 4 | Solid | 104.1 | 0.166 | −1.73 | 40.2 | −0.91 | 242 |
| 203790 | $CH_3$—Ph-p-tBu | Ph-p-Me | 5 | Solid | 18.9 | 0.178 | −1.36 | >100 | N/A | N/A |
| 203784 | Ph-p-tBu | Ph-m-Cl | 2 | Solid | 31.8 | 0.224 | −2.03 | 32.2 | −0.58 | 144 |
| 203791 | $CH_3$—Ph-p-tBu | Ph | 5 | Solid | 14.4 | 0.245 | −1.72 | >100 | N/A | N/A |
| 203796 | $CH_3$—Ph-p-tBu | Ph-p-tBu | 5 | Solid | 14.8 | 0.351 | −1.70 | >100 | N/A | N/A |
| 203787 | $CH_3$—Ph-o-Me | Ph-m-Cl | 4 | Solid | 78.2 | 0.381 | −2.01 | 31.0 | −1.10 | 81 |
| 203792 | $CH_3$—Ph-m-Cl | Ph-m-Cl | 4 | Solid | 67.8 | 0.419 | −1.55 | 21.1 | −1.66 | 50 |
| 203793 | $CH_3$—Ph-m-Me | Ph-m-$MeF_3$ | 5 | Solid | 65.2 | N/A | NA | 15.9 | −1.03 | N/A |

TABLE 4

Selectivity of CCG-50014 analogs for RGS4 over RGS8.

| CCG Number | R1 | R2 | Fold Selectivity (RGS8 IC$_{50}$/ RGS4 IC$_{50}$) |
|---|---|---|---|
| 203763 | iBu | tBu | 6679 |
| 203769 | Bu | Et | 5964 |
| 203770 | Bu | Bu | 4077 |
| 203742 | CH$_3$—Ph-p-F | CH$_3$—Ph-p-Me | 3062 |
| 203734 | CH$_3$—Ph | CH$_3$—Ph-p-Me | 2914 |
| 203738 | CH$_3$—Ph-p-Me | CH$_3$—Ph-p-Me | 2870 |
| 203762 | iBu | Et | 2715 |
| 203764 | iBu | Bu | 2513 |
| 203731 | CH$_3$—Ph-p-Cl | Ph-p-Me | 2360 |
| 203760 | Me | tBu | 2000 |
| 203765 | CH$_3$—Ph-p-F | Bu | 1975 |
| 203736 | CH$_3$—Ph-p-Me | Ph-p-Me | 1289 |
| 203757 | Bu | Me | 1235 |
| 203735 | CH$_3$—Ph-p-F | Ph-p-OMe | 1036 |
| 203777 | CH$_3$—Ph-m-Cl | Ph-p-Me | 1029 |
| 203732 | CH$_3$—Ph-p-Me | Ph | 922 |
| 203733 | CH$_3$—Ph-p-Me | Ph-p-Cl | 753 |
| 203785 | CH$_3$—Ph | Ph-m-Me | 561 |
| 203781 | CH$_3$—Ph-m-Me | Ph | 560 |
| 203761 | iBu | Ph-p-Me | 550 |
| 203727 | CH$_3$—Ph-p-F | Ph-p-Cl | 543 |
| 203724 | CH$_3$—Ph | Ph-p-Me | 536 |
| 203746 | CH$_3$—Ph | Ph-p-OMe | 513 |
| 203755 | CH$_3$—Ph-p-OMe | Ph-p-OMe | 503 |
| 203730 | CH$_3$—Ph-p-Cl | Ph-p-Cl | 488 |
| 203728 | CH$_3$—Ph-p-F | Ph-m,p-Cl | 478 |
| 203767 | Bu | Ph-p-Me | 475 |
| 203743 | CH$_3$—Ph-m,p-Cl | Ph-p-Me | 462 |
| 203741 | CH$_3$—Ph-p,m-Cl | Ph-p-OMe | 454 |
| 203759 | Me | Ph-p-Me | 442 |
| 203771 | CH$_3$—Ph | Ph-p-tBu | 395 |
| 203726 | CH$_3$—Ph-p-F | Ph | 388 |
| 203773 | CH$_3$—Ph | Ph-m-Cl | 330 |
| 203739 | CH$_3$—Ph-p,m-Cl | Ph | 313 |
| 203783 | CH$_3$—Ph-m-Cl | Ph | 303 |
| 203722 | CH$_3$—Ph | Ph | 233 |
| 203794 | CH$_3$—Ph-m-Me | Ph-m-Me | 226 |
| 203745 | CH$_3$—Ph-p-OMe | Ph | 212 |
| 203723 | CH$_3$—Ph | Ph-p-Cl | 179 |

For clarity, only compounds with IC50 values on RGS4 <50 nM are included in this table. Selectivity was determined by comparing the IC50 values from duplex FCPIA assays. n ≥ 2.

Figure 15:
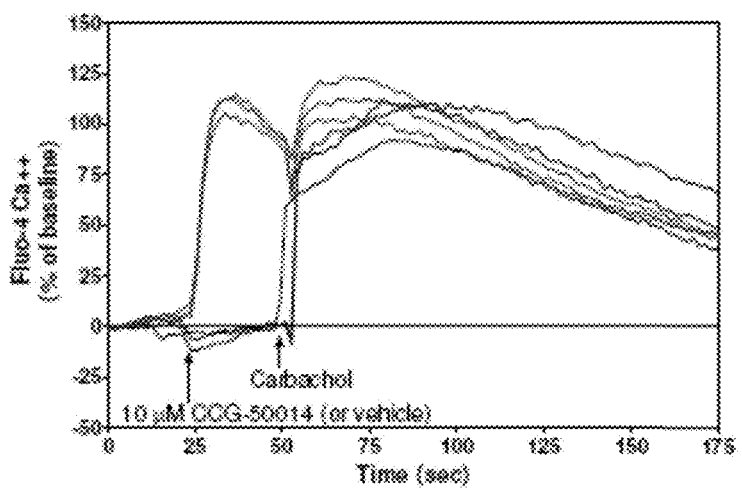
FIG. 15 shows that A) CCG-50014 induces a calcium transient in HEK293 cells. Fluo4-loaded cells were exposed to 10 µM CCG-50014 or DMSO control before an injection of 1 nM carbachol. CCG-50014 induced a calcium mobilization event on its own, demonstrating that this compound has an unidentified off-target effect. Representative data shown from three wells for each condition. B) Chemical structures of the 3 compounds that did not show calcium mobilization effects and were more potent and soluble than CCG-50014.
Figure 15:
Figure 15:
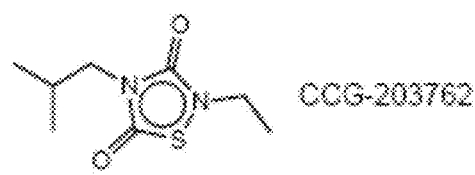
Figure 15:
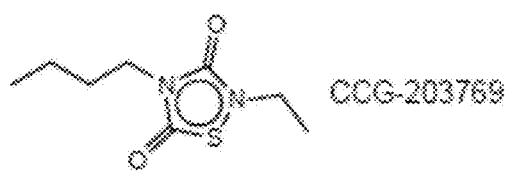

Identification of Compounds with Minimized Off-Target Effects:

CCG-50014 tests were initially attempted in a Ca$^{2+}$ mobilization assay using a cell line stably expressing the M3 muscarinic receptor and expressing RGS4 under control of a doxycycline promoter. A 30-minute pretreatment of these cells with CCG-50014 completely inhibited the Ca$^{2+}$ response to carbachol. To probe the mechanism of this effect, the compound preoccupation time was reduced to enable monitoring of intracellular calcium levels directly after compound addition (FIG. 15). CCG-50014 induced a marked calcium transient in these cells that after prolonged treatment would be expected to deplete calcium stores. Since proper calcium handling is crucial for cellular functioning, all of the available CCG-50014 analogs were tested for their ability to induce calcium mobilization at a concentration of 10 μM. As shown in Table 3 and FIG. 15B, there were a number of analogs that did not produce a significant calcium effect in this cell system, several of which still potently inhibit RGS4.

The SAR analysis identified three compounds that have no ability to induce calcium mobilization that also have improved solubility and potency as compared to CCG-50014. These three compounds are CCG-203760, CCG-203762, and CCG-203769. Of these compounds, CCG-203769 displays most of the desired properties of an RGS inhibitor. The compound is highly soluble (>5 mM, aqueous), potently inhibits RGS4 (IC50 14 nM), displays greater selectivity for RGS4 vs RGS8 than did other compounds, and did not induce a calcium transient in HEK-293 cells.

From these SAR studies, compounds were identified that are more potent and selective than the parent compound (e.g. CCG-203731, CCG-203769) and have identified potential regions of the molecule (R2) that are important in driving RGS selectivity. An alkyl chain or a phenyl ring with a small substituent at the para position provide compounds with selectivity for RGS4. Also, compounds were identified (e.g. CCG-203769) that have improved physicochemical properties, and minimal off-target calcium effects, thus facilitating future in vivo experiments which would have been hampered by solubility and off-target issues of CCG-50014.

Figure 16:
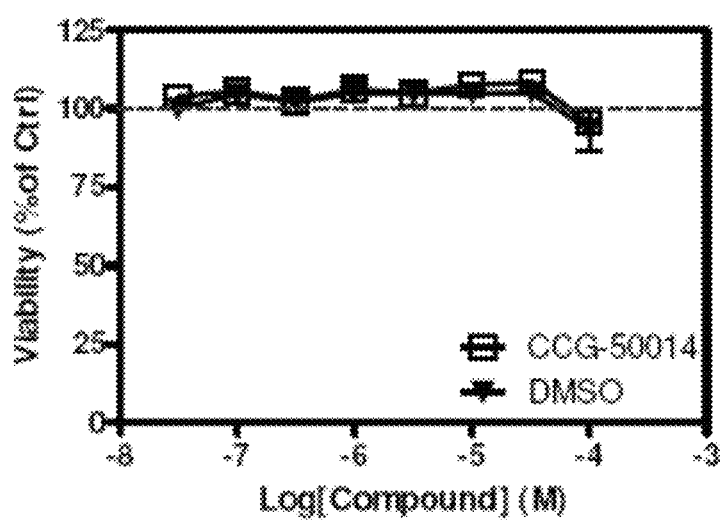
FIG. 16 shows that CCG-50014 does not affect HEK-293 viability. Cells were treated with CCG-50014 or vehicle control overnight and assayed for viability using WST-1. Data are presented as the mean±SEM from three independent experiments.

CCG-50014 does not Affect Cell Viability:

CCG-50014 is no more toxic than the vehicle (DMSO) control (FIG. 16). HEK293 cells were treated with CCG-50014 or vehicle controls in DMEM+0.1% bovine serum albumin. After an overnight incubation at 37° C. cells were analyzed for viability using the WST-1 reagent. At concentrations up to 100 μM, CCG-50014 did not reduce cell viability below control levels.

Figure 17:
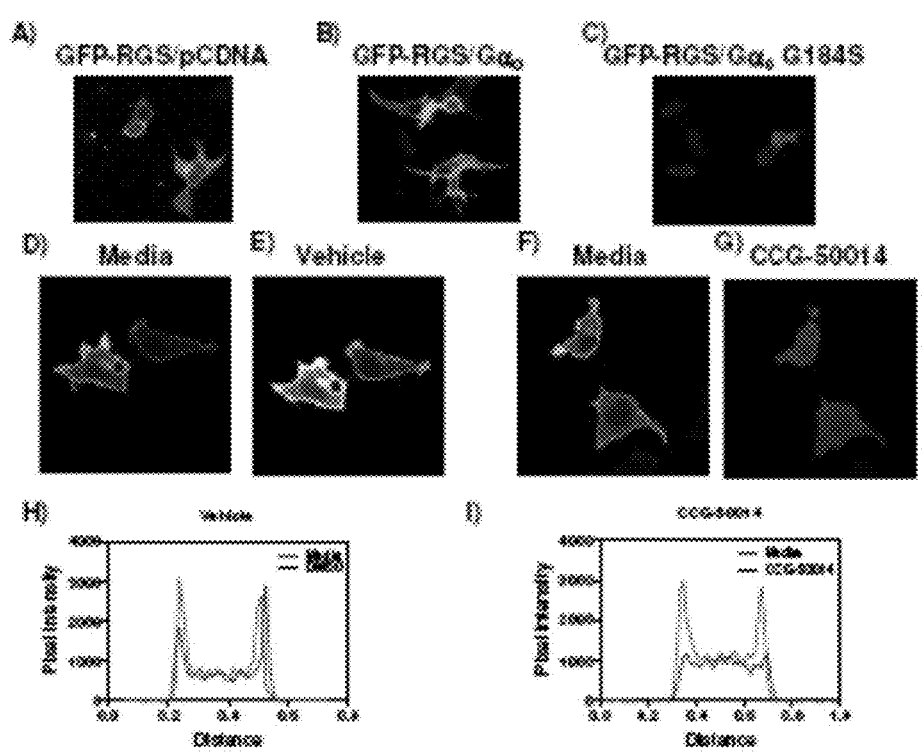
FIG. 17 shows RGS4 is recruited to the plasma membrane by coexpression of $G\alpha_o$, and this recruitment is inhibited by CCG-50014. A) RGS4-GFP was expressed in a diffuse cytosolic pattern. B) When coexpressed with $G\alpha_o$, the RGS translocates to the plasma membrane. C) Co-expression with the RGS-insensitive $G\alpha_o$ mutant (G184S) does not induce this translocation. D/E/H) Cells coexpressing RGS4-GFP and $G_{--o}$ show no change in the membrane localization of RGS4 after treatment with vehicle control (DMSO). F/G/I) CCG-50014 (100 µM) is able to reverse the $G\alpha_o$-induced RGS membrane translocation. Representative data shown from at least three independent experiments with 5-10 cells imaged per experiment. Line scans shown in H and I were quantified by drawing a line perpendicular to the long axis of the cell at identical sites in both pre/post treatment images and calculating pixel intensity using ImageJ.

CCG-50014 and Related Analogs Inhibit the RGS4/Gα$_o$ Interaction in Living Cells:

The members of the CCG-50014 class of compounds are potent inhibitors of the RGS4/Gα$_o$ PPI with IC$_{50}$ values in the 3-200 nM range in vitro. To determine if these compounds can also inhibit this PPI in living cells, a series of experiments were performed that were designed to monitor the subcellular localization of a green fluorescent protein (GFP)-tagged RGS4 that was transiently overexpressed in HEK-293T cells (FIG. 17). GFP-RGS4 was primarily expressed as a diffuse cytosolic protein (FIG. 17A). Upon co-transfection with either wildtype Gα$_o$ or the constitutively active Gα$_o$ (QL) mutant, GFP-RGS4 relocates to the plasma membrane. Co-expression with the RGS insensitive mutant Gα$_o$ (G184S) did not cause membrane localization of GFP-RGS4. At this level of overexpression, the RGS4/Gα$_o$ PPI is constitutive probably due to the rapid GDP exchange rate of Gα$_o$ (Remmers, A. E., et al., Biochemistry, 1999. 38(42): p. 13795-800). If cells expressing Gα$_o$ and GFP-RGS4 are exposed to CCG-50014, the membrane localization of GFP-RGS4 is reversed and the RGS protein translocates back into a cytosolic expression pattern (FIG. 17D/E). Several analogs of CCG-50014 were tested in this assay (including CCG-203769 and CCG-203757) with similar results. To ensure that the N-terminal GFP tag was not affecting the assay these experiments were repeated with a C-terminal GFP fusion of RGS4 and similar results were obtained. This effect was observed for concentrations down to 1 μM CCG-50014. At high concentrations (100 μM), the effect was observed essentially instantaneously (<1 minute) and occurred within 10 minutes for lower concentrations (e.g. 10 μM). These results show that CCG-50014, CCG-203769, and other analogs can inhibit the RGS4/Gα$_o$ interaction in living cells.

Figure 18:
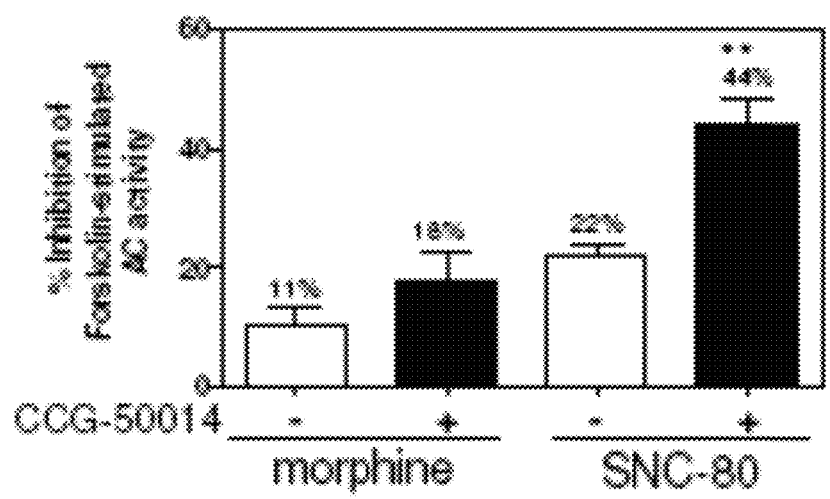
FIG. 18 shows CCG-50014 potentiates the activity of the δ-opioid receptor ligand SNC-80 in SHSY5Y cells Inhibition of forskolin-activated adenylate cyclase activity by either the µ-opioid receptor or the δ-opioid receptor was measured in the absence and presence of 100 µM CCG-50014. Data are presented as the mean±SEM from three independent experiments.  $P<0.001$

CCG-50014 Potentiates Signaling Through the δ-Opioid Receptor:

Wang et al. (Wang et al., J Biol Chem, 2009. 284(27): p. 18357-67) showed that in the SH-SY5Y neuroblastoma cell line, siRNA knockdown of RGS4 selectively potentiates signaling through the δ-opioid receptor over the μ-opioid receptor. Since both receptors couple to the same G-proteins, the RGS4 selectivity observed in this system is particularly useful in dissecting the compound's action. A low concentration (100 nM) of either the μ-opioid receptor agonist morphine or the δ-opioid receptor agonist SNC-80 produced a small (10-20%) inhibition of forskolin-stimulated adenylate cyclase activity. CCG-50014 (100 μM) significantly potentiated the effect of the δ-opioid agonist (44% inhibition vs 22% inhibition without the compound, p<0.001), as would be expected of an RGS4 inhibitor in this system (FIG. 18), with only a modest effect upon the μ-receptor signaling. The observed receptor selectivity of compound action is consistent with CCG-50014 acting by inhibiting RGS4. There is significant potentiation of the δ-opioid signaling as would be expected of an RGS inhibitor.

CCG-203769 Potentiates the M3 Muscarinic Receptor Activity Via Inhibition of RGS4:

To further probe the ability of the CCG-50014 class of compounds to inhibit RGS actions in a cellular setting, a series of experiments were performed using the engineered cell system expressing the M3 muscarinic receptor with RGS4 under doxycycline control. Upon addition of carbachol to these cells, a $G\alpha_o$-dependent intracellular calcium mobilization was initiated by the activation of phospholipase C. After induction of RGS4 expression, calcium signaling as suppressed by ~80%. A compound that inhibited RGS4 relieved this suppression.

As noted above, when these experiments were performed with CCG-50014 it was found that the compound itself induced a sizable calcium transient. This off-target effect clearly makes it difficult to interpret data from these experiments. To circumvent this issue, CCG-50014 analogs were identified that were unable to induce a calcium flux in HEK-293 cells. One of these compounds, CCG-203769, is more potent at inhibiting RGS4 than CCG-50014 and is more soluble and was therefore chosen for study in this system.

Incubation with CCG-203769 for 15 minutes prior to carbachol stimulation resulted in a partial reversal of the RGS4-mediated inhibition (FIG. 19) without affecting M3-mediated calcium signal in the absence of RGS4 expression. This result further confirms this class of compounds is acting as an RGS4 inhibitor in living cells. Furthermore, the response occurs at micromolar concentrations, which is more in concordance with what is observed in vitro. This assay also measures $G_q$ signaling (as opposed to $G_{i/o}$ in the opioid studies), proving that the effect of this compound is not G-protein dependent.

The enhanced $Ca^{2+}$ signaling induced by CCG-203769 occurs at concentrations as low as 1 μM. While this compound was chosen for study because of its inability to stimulate calcium mobilization by itself, a weak effect on calcium handling plays a significant role over the time course of the experiment. It is also possible that at high concentrations of compound other, as of yet unknown off-target effects are occurring that disrupt calcium handling. Regardless, it does appear that CCG-203769 can inhibit RGS4 in living cells at concentrations that do not cause any measurable off-target effects.

Example 3

Additional Compounds

Representative Procedure for the Synthesis of TDZD

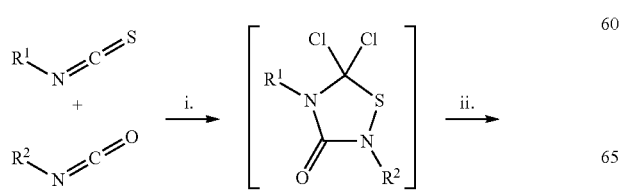

-continued

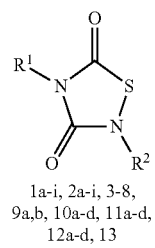

1a-i, 2a-i, 3-8,
9a,b, 10a-d, 11a-d,
12a-d, 13

A solution of the isocyanate (1 equiv.) and isothiocyanate (1 equiv.) in THF (5 mL per mmol) was cooled to 0° C. under an inert atmosphere and $SO_2Cl_2$ (1 equiv.) was added slowly. The reaction was brought to room temperature and stirred overnight before being opened to air and stirred for a further 10 min. The solvent was then removed under reduced pressure and the resulting TDZD was purified by column chromatography (0%-20% EtOAc in pet ether).

CCG206621—4-(3-ethoxypropyl)-2-ethyl-1,2,4-thiadiazolidine-3,5,-dione

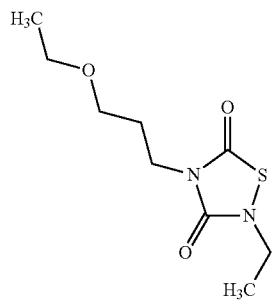

$^1$H NMR (400 MHz, $CDCl_3$) δ 1.16 (t, J=7.0 Hz, 3H), 1.26 (t, J=7.2 Hz, 3H), 1.90-1.97 (m, 2H), 3.42 (t, J=7.0 Hz, 2H), 3.46 (t, J=6.0 Hz, 2H), 3.67 (q, J=7.2 Hz, 2H), 3.78 (t, J=6.8 Hz, 2H).

CCG206622—2-ethyl-4-((tetrahydrofuran-2-yl)methyl)-1,2,4-thiadiazolidine-3,5-dione

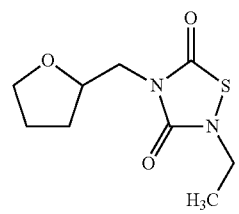

$^1$H NMR (400 MHz, $CDCl_3$) δ 1.25 (t, J=7.2 Hz, 3H), 1.58-1.66 (m, 1H), 1.82-2.05 (m, 3H), 3.59 (dd, J=4.5, 13.6 Hz, 1H), 3.64-3.70 (m, 2H), 3.72-3.80 (m, 2H), 3.86-3.91 (m, 1H), 4.22-4.28 (m, 1H).

CCG206623—2-ethyl-4-(3-methoxypropyl)-1,2,4-thiadiazolidine-3,5-dione

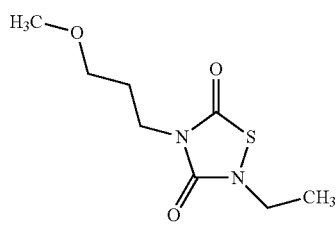

¹H NMR (400 MHz, CDCl₃) δ 1.26 (t, J=7.2 Hz, 3H), 1.89-1.96 (m, 2H), 3.30 (s, 3H), 3.42 (t, J=6.0 Hz, 2H), 3.66 (q, J=7.2 Hz, 2H), 3.77 (t, J=7.0 Hz, 2H).

CCG206628—2-ethyl-4-(prop-2-ynyl)-1,2,4-thiadiazolidine-3,5-dione

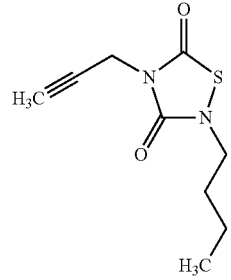

¹H NMR (400 MHz, CDCl₃) δ 0.95 (t, J=7.4 Hz, 3H), 1.33-1.42 (m, 2H), 1.59-1.66 (m, 2H), 2.27 (t, J=2.5 Hz, 1H), 3.64 (t, J=7.2 Hz, 2H), 4.42 (d, J=2.5 Hz, 2H).

CCG206629—4-((1-benzyl-1H-1,2,3-triazol-5-yl)methyl)-2-ethyl-1,2,4-thiadiazolidine-3,5-dione

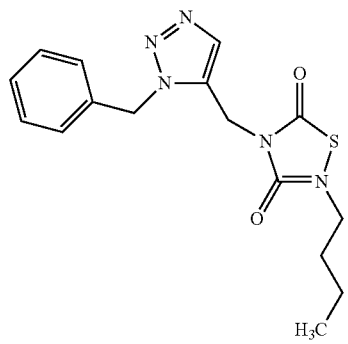

Benzyl azide (1 equiv.) and CCG206628 (1 equiv.) were suspended in a 1:1:1 water/ᵗBuOH/MeOH mixture (6 mL per mmol). Sodium ascorbate (0.1 equiv.) was added followed by CuSO₄ (1 mol %) and the reaction was stirred overnight at room temperature. The solvent was removed under reduced pressure and the residue purified by column chromatography (0%-40% EtOAc in hexane).

¹H NMR (400 MHz, CDCl₃) δ 0.90 (t, J=7.3 Hz, 3H), 1.27-1.36 (m, 2H), 1.53-1.60 (m, 2H), 3.58 (t, J=7.2 Hz, 2H), 4.90 (s, 2H), 5.46 (s, 2H), 7.22-7.24 (m, 2H), 7.31-7.33 (m, 3H), 7.53 (s, 1H).

Table 5 shows activity of compounds.

TABLE 5

|  | RGS4 LogIC50 | RGS8 LogIC50 |
|---|---|---|
| 206620 |  | −401.4 |
| 206621 | −8.247 | −4.241 |
| 206622 | −8.081 | −4.127 |
| 206623 | −8.346 | −4.201 |
| 206624 | −4.038 | 14.11 |
| 206625 | −305.7 | −396.6 |

TABLE 5-continued

|  | RGS4 LogIC50 | RGS8 LogIC50 |
|---|---|---|
| 206626 | −479.2 | −508.5 |
| 206627 | −0.2959 | −2.874 |
| 206628 | −8.280 | −4.712 |
| 206629 | −8.161 | −4.915 |
| 50014 | −8.704 | −5.349 |

Further structure of compounds from Table 5 include:

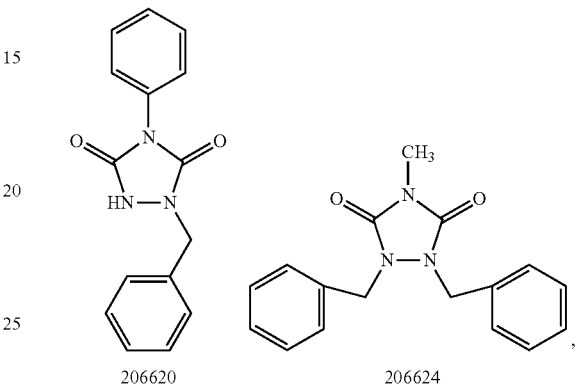

206620, 206624

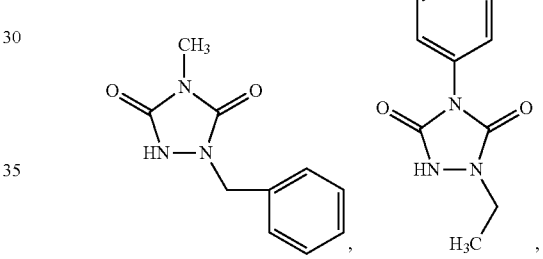

206625, 206626

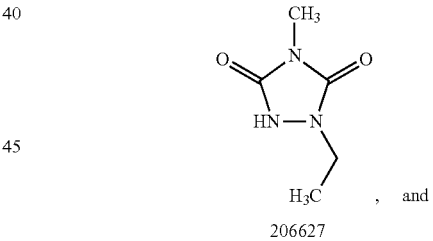

206627, and

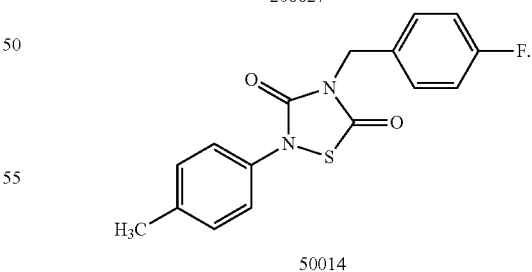

50014

Example 4

Additional Small Molecule Inhibitors of Regulators of G Protein Signaling (RGS) Proteins As described above, CCG-50014 was identified as a selective inhibitor of RGS4 that acted by forming a covalent adduct to cysteine residues in the RGS protein (Blazer et al., Biochemistry 2011, 50, 3181-3192; Roman et al., J. Biomol. Screening 2009, 14, 610-619). With an IC50 of 30 nM, it is the most potent RGS inhibitor reported to date. To further define the structural requirements for high-potency inhibition of this protein, analogues of 50014 were synthesized with variation in both the N2 and the N4 side chains. In addition, a set of these newly synthesized RGS4 inhibitors were evaluated for their effects on calcium mobilization, an off-target activity displayed by 50014. The synthesis of CCG-50014 (1a) and its thiadiazolidinone (TDZD) analogues is shown in Example 3 above. Commercially available isothiocyanates were reacted with isocyanates in the presence of sulfuryl chloride (Slomczyńska et al., J. Heterocycl. Chem. 1984, 21, 241-246). This allowed a range of R1 and R2 substituents, having varying lipophilic, electronic, and steric properties, to be evaluated. While chlorine gas (Martinez et al., J. Med. Chem. 2002, 45, 1292-1299) or N-chlorosuccinimide (Nasim et al., Tetrahedron Lett. 2009, 50, 257-259) are also used in literature procedures for making TDZDs, we found the use of sulfuryl chloride straightforward and consistent. The resulting S-chloroisothiocarbamoyl chloride, proposed by Slomczyńska and Barany (supra), was subsequently oxidized in atmospheric oxygen to the desired products. This reaction was easily carried out in parallel, with typically 11 different reactions running simultaneously. In total, 75 TDZD analogues were synthesized, with 39 (1a-i, 2a-i, 3-8, 9a,b, 10a-d, 11a-d, 12a-d, and 13) reported in Table 6.

TABLE 6

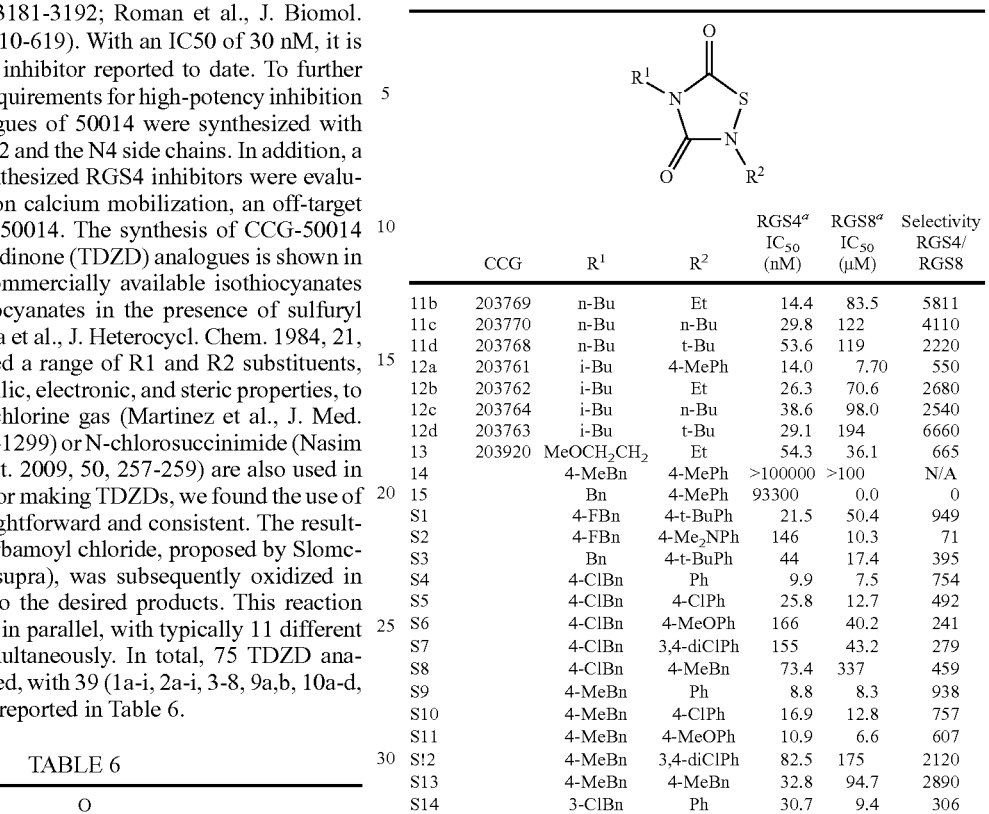

| CCG | R¹ | R² | RGS4ᵃ IC$_{50}$ (nM) | RGS8ᵃ IC$_{50}$ (µM) | Selectivity RGS4/RGS8 |
|---|---|---|---|---|---|
| 1a | 50014 | 4-FBn | 4-MePh | 30.1 | 11.0 | 366 |
| 1b | 203726 | 4-FBn | Ph | 16.3 | 6.20 | 380 |
| 1c | 203727 | 4-FBn | 4-ClPh | 13.5 | 7.60 | 564 |
| 1d | 203735 | 4-FBn | 4-MeOPh | 10.9 | 11.4 | 1050 |
| 1e | 203728 | 4-FBn | 3,4-diClPh | 35.7 | 17.2 | 481 |
| 1f | 203775 | 4-FBn | 3-CF₃Ph | 79.3 | 16.2 | 204 |
| 1g | 203788 | 4-FBn | 3-MePh | 121 | 7.10 | 59 |
| 1h | 203776 | 4-FBn | 3-ClPh | 52.3 | 12.8 | 245 |
| 1i | 203742 | 4-FBn | 4-MeBn | 12.9 | 39.8 | 3090 |
| 2a | 203724 | Bn | 4-MePh | 14.4 | 7.5 | 519 |
| 2b | 203722 | Bn | Ph | 23.5 | 5.60 | 239 |
| 2c | 203723 | Bn | 4-ClPh | 28.7 | 5.20 | 183 |
| 2d | 203746 | Bn | 4-MeOPh | 23.9 | 12.3 | 515 |
| 2e | 203725 | Bn | 3,4-diClPh | 88.9 | 13.2 | 149 |
| 2f | 203772 | Bn | 3-CF₃Ph | 57.4 | 16.4 | 286 |
| 2g | 203785 | Bn | 3-MePh | 38.2 | 21.3 | 558 |
| 2h | 203773 | Bn | 3-ClPh | 32.5 | 10.9 | 335 |
| 2i | 203734 | Bn | 4-MeBn | 7.20 | 20.4 | 2840 |
| 3 | 203731 | 4-ClBn | 4-MePh | 5.40 | 11.8 | 2170 |
| 4 | 203736 | 4-MeBn | 4-MePh | 8.60 | 11.6 | 1340 |
| 5 | 203777 | 3-ClBn | 4-MePh | 17.4 | 17.5 | 1005 |
| 6 | 203782 | 3-MeBn | 4-MePh | 14.5 | 9.90 | 679 |
| 7 | 203754 | 4-MeOBn | 4-MePh | 1765 | 312 | 1780 |
| 8 | 203743 | 3,4-diClBn | 4MePh | 34.2 | 15.7 | 460 |
| 9a | 203765 | 4-FBn | n-Bu | 15.6 | 31.6 | 2020 |
| 9b | 203766 | 4-FBn | Et | 22.3 | 18.7 | 842 |
| 10a | 203759 | Me | 4-MePh | 18.9 | 8.40 | 445 |
| 10b | 203758 | Me | Et | 22.3 | 37.0 | 1660 |
| 10c | 203757 | Me | n-Bu | 23.5 | 28.4 | 1210 |
| 10d | 203760 | Me | t-Bu | 27.8 | 56.0 | 2020 |
| 11a | 203767 | n-Bu | 4-MePh | 19.7 | 9.50 | 483 |
| 11b | 203769 | n-Bu | Et | 14.4 | 83.5 | 5811 |
| 11c | 203770 | n-Bu | n-Bu | 29.8 | 122 | 4110 |
| 11d | 203768 | n-Bu | t-Bu | 53.6 | 119 | 2220 |
| 12a | 203761 | i-Bu | 4-MePh | 14.0 | 7.70 | 550 |
| 12b | 203762 | i-Bu | Et | 26.3 | 70.6 | 2680 |
| 12c | 203764 | i-Bu | n-Bu | 38.6 | 98.0 | 2540 |
| 12d | 203763 | i-Bu | t-Bu | 29.1 | 194 | 6660 |
| 13 | 203920 | MeOCH₂CH₂ | Et | 54.3 | 36.1 | 665 |
| 14 |  | 4-MeBn | 4-MePh | >100000 | >100 | N/A |
| 15 |  | Bn | 4-MePh | 93300 | 0.0 | 0 |
| S1 |  | 4-FBn | 4-t-BuPh | 21.5 | 50.4 | 949 |
| S2 |  | 4-FBn | 4-Me₂NPh | 146 | 10.3 | 71 |
| S3 |  | Bn | 4-t-BuPh | 44 | 17.4 | 395 |
| S4 |  | 4-ClBn | Ph | 9.9 | 7.5 | 754 |
| S5 |  | 4-ClBn | 4-ClPh | 25.8 | 12.7 | 492 |
| S6 |  | 4-ClBn | 4-MeOPh | 166 | 40.2 | 241 |
| S7 |  | 4-ClBn | 3,4-diClPh | 155 | 43.2 | 279 |
| S8 |  | 4-ClBn | 4-MeBn | 73.4 | 337 | 459 |
| S9 |  | 4-MeBn | Ph | 8.8 | 8.3 | 938 |
| S10 |  | 4-MeBn | 4-ClPh | 16.9 | 12.8 | 757 |
| S11 |  | 4-MeBn | 4-MeOPh | 10.9 | 6.6 | 607 |
| S!2 |  | 4-MeBn | 3,4-diClPh | 82.5 | 175 | 2120 |
| S13 |  | 4-MeBn | 4-MeBn | 32.8 | 94.7 | 2890 |
| S14 |  | 3-ClBn | Ph | 30.7 | 9.4 | 306 |
| S15 |  | 3-ClBn | 4-t-BuPh | 224 | 32.2 | 144 |
| S16 |  | 3-ClBn | 3-MePh | 64.5 | 10.1 | 156 |
| S17 |  | 3-ClBn | 3-ClPh | 419 | 21.1 | 50 |
| S18 |  | 3-ClBn | 3-CF₃Ph | 1440 | 16.2 | 11 |
| S19 |  | 3-MeBn | Ph | 15.1 | 8.4 | 555 |
| S20 |  | 3-MeBn | 4-t-BuPh | 191 | 17.8 | 93 |
| S21 |  | 3-MeBn | 3-MePh | 45.6 | 10.4 | 228 |
| S22 |  | 3-MeBn | 3-ClPh | 381 | 31 | 82 |
| S23 |  | 3-MeBn | 3-CF₃Ph | N/A | 15.9 | N/A |
| S24 |  | 4-MeOBn | Ph | 33.7 | 7.2 | 214 |
| S25 |  | 4-MeOBn | 4-ClPh | 68.7 | 9.9 | 144 |
| S26 |  | 4-MeOBn | 4-MeOPh | 35.2 | 17.6 | 500 |
| S27 |  | 4-MeOBn | 3,4-diClPh | 87.4 | 36 | 412 |
| S28 |  | 4-MeOBn | 4-MeBn | 103 | 92.9 | 901 |
| S29 |  | 3,4-diClBn | Ph | 24.1 | 7.5 | 313 |
| S30 |  | 3,4-diClBn | 4-ClPh | 68.4 | 16.7 | 244 |
| S31 |  | 3,4-diClBn | 4-MeOPh | 12.8 | 5.9 | 464 |
| S32 |  | 3,4-diClBn | 4-diClPh | 155 | 125 | 805 |
| S33 |  | 3,4-diClBn | 4-MeBn | 113 | 109 | 962 |
| S34 |  | 4-t-BuBn | 4-MePh | 178 | >100 | N/A |
| S35 |  | 4-t-BuBn | Ph | 246 | >100 | N/A |
| S36 |  | 4-t-BuBn | 4-t-BuPh | 351 | >100 | N/A |
| S37 |  | Bn | Br | 32900 | 144 | 4 |

General Procedures:

All reactions were carried out under an inert atmosphere of nitrogen with dry solvents, using anhydrous conditions unless otherwise stated. Dry tetrahydrofuran (THF) was distilled from the sodium benzophenone ketyl radical. Reagents were purchased at the highest commercial quality and used without further purification. Column chromatography was performed with a Combiflash Rf Companion, using Redisep Rf disposable columns containing 40-60 µm silica, using reagent grade ethyl acetate and petroleum ether. A Bruker Avance III 400 MHz NMR spectrometer was used to record 1H and 13C NMR spectra. Microanalysis for key compounds was determined with a Perkin Elmer 240C analyser.

General Procedure for Synthesis of 1,2,4-thiadiazolidine-3,5-diones:

A stirred solution of isocyanate (1 mmol) and isothiocyanate (1 mmol) in THF (5 mL) was cooled to 0° C. Sulfuryl chloride (1 mmol) was added slowly (either as straight or as a 1 M solution in $CH_2Cl_2$) and the mixture was allowed to warm to room temperature and stirred overnight. The reaction was then opened to the air and stirred for 30 minutes before the solvent was removed under reduced pressure. Flash chromatography (0-20% ethyl acetate in pet ether) was used to purify the crude reaction mixture.

2-p-tolyl-4-(4-fluorobenzyl)-1,2,4-thiadiazolidine-3,5-dione (1a)

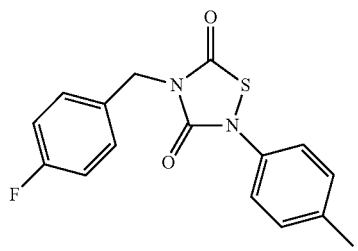 [SMILES: Cc1ccc(-n2sc(=O)n(Cc3ccc(F)cc3)c2=O)cc1]

Yield=41%. $^1$H NMR (400 MHz, CDCl$_3$) δ 2.35 (s, 3H), 4.87 (s, 2H), 7.01-7.05 (m, 2H), 7.20-7.22 (m, 2H), 7.35-7.38 (m, 2H), 7.48-7.51 (m, 2H). $^{13}$C NMR (100 MHz, CDCl$_3$) δ 20.9, 45.3, 115.6 (d, $J_{CF}$=21.6 Hz), 123.7, 130.0, 130.9 (d, $J_{CF}$=3.3 Hz), 131.1, (d, $J_{CF}$=8.3 Hz), 133.0, 137.3, 151.0, 162.7 (d, $J_{CF}$=247.4 Hz), 165.1; anal. (C16H13FN2O2S); CHN 2-phenyl-4-(4-fluorobenzyl)-1,2,4-thiadiazolidine-3,5-dione (1b)

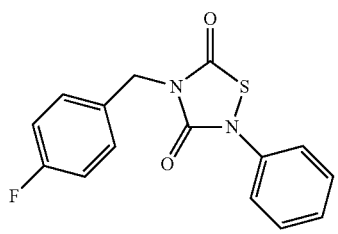 [SMILES: O=c1sn(-c2ccccc2)c(=O)n1Cc1ccc(F)cc1]

Yield=68%. $^1$H NMR (400 MHz, CDCl$_3$) δ 4.88 (s, 2H), 7.04 (t, J=8.6 Hz, 2H), 7.26-7.30 (m, 1H), 7.40-7.44 (m, 2H), 7.48-7.51 (m, 4H). $^{13}$C NMR (100 MHz, CDCl$_3$) δ 45.4, 115.7 (d, $J_{CF}$=21.5 Hz), 123.4, 127.1, 129.5, 130.9 (d, $J_{CF}$=3.1 Hz), 131.1 (d, $J_{CF}$=7.6 Hz), 135.7, 150.9, 162.7 (d, $J_{CF}$=246.9 Hz), 165.0.

2-(4-chlorophenyl)-4-(4-fluorobenzyl)-1,2,4-thiadiazolidine-3,5-dione (1c)

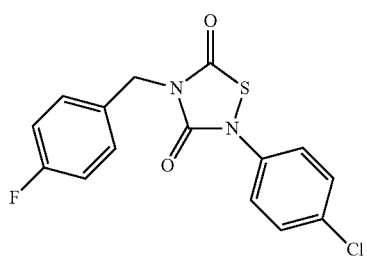 [SMILES: O=c1sn(-c2ccc(Cl)cc2)c(=O)n1Cc1ccc(F)cc1]

Yield=64%. 1H NMR (400 MHz, CDCl3) δ 4.87 (s, 2H), 7.04 (t, J=8.6 Hz, 2H), 7.37-7.40 (m, 2H), 7.44-7.50 (m, 4H). $^{13}$C NMR (100 MHz, CDCl$_3$) δ 45.5, 115.7 (d, J=21.4 Hz), 124.5, 129.6, 130.7 (d, $J_{CF}$=3.9 Hz), 131.2 (d, $J_{CF}$=8.4 Hz), 132.6, 134.2, 150.8, 162.8 (d, $J_{CF}$=247.6 Hz), 164.5.

2-(4-methoxyphenyl)-4-(4-fluorobenzyl)-1,2,4-thiadiazolidine-3,5-dione (1d)

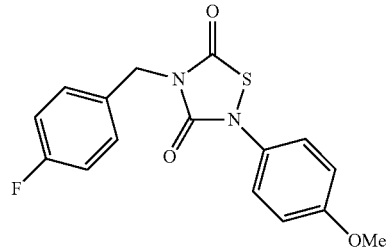 [SMILES: COc1ccc(-n2sc(=O)n(Cc3ccc(F)cc3)c2=O)cc1]

Yield=71%. 1H NMR (400 MHz, CDCl3) δ 3.81 (s, 3H), 4.86 (s, 2H), 6.91-6.93 (m, 2H), 7.01-7.05 (m, 2H), 7.36-7.38 (m, 2H), 7.48-7.51 (m, 2H). $^{13}$C NMR (100 MHz, CDCl$_3$) δ 45.4, 55.6, 114.8, 115.7 (d, $J_{CF}$=22.1 Hz), 126.2, 128.0, 131.0 (d, $J_{CF}$=3.0 Hz), 131.1 (d, $J_{CF}$=8.0 Hz), 151.4, 158.9, 162.8 (d, $J_{CF}$=246.4 Hz), 165.3.

2-(3,4-dichlorophenyl)-4-(4-fluorobenzyl)-1,2,4-thiadiazolidine-3,5-dione (1e)

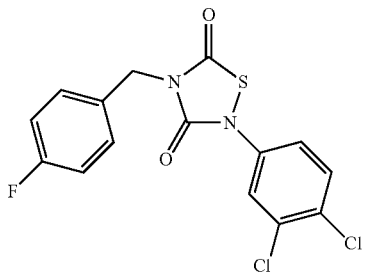 [SMILES: O=c1sn(-c2ccc(Cl)c(Cl)c2)c(=O)n1Cc1ccc(F)cc1]

Yield=52%. 1H NMR (400 MHz, CDCl3) δ 4.87 (s, 2H), 7.04 (t, J=8.6 Hz, 2H), 7.34-7.36 (m, 1H), 7.46-7.50 (m, 3H), 7.70-7.71 (m, 1H). $^{13}$C NMR (100 MHz, CDCl$_3$) δ 45.6, 115.8 (d, $J_{CF}$=21.5 Hz), 122.0, 124.8, 130.5 (d, $J_{CF}$=3.0 Hz), 130.8, 131.0, 131.2 (d, $J_{CF}$=8.4 Hz), 133.6, 135.1, 150.7, 162.8 (d, $J_{CF}$=247.6 Hz).

2-(3-trifluoromethylphenyl)-4-(4-fluorobenzyl)-1,2,4-thiadiazolidine-3,5-dione (1f)

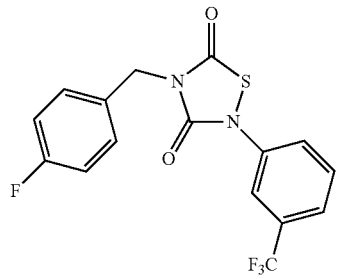 [SMILES: O=c1sn(-c2cccc(C(F)(F)F)c2)c(=O)n1Cc1ccc(F)cc1]

Yield=65%. 1H NMR (400 MHz, CDCl3) δ 4.89 (s, 2H), 7.02-7.07 (m, 2H), 7.48-7.51 (m, 2H), 7.54-7.55 (m, 2H), 7.67-7.70 (m, 1H), 7.84-7.85 (m, 1H). $^{13}$C NMR (100 MHz, CDCl3) δ 45.6, 115.8 (d, $J_{CF}$=22.1 Hz), 120.0 (q, $J_{CF}$=4.0 Hz), 123.4 (q, $J_{CF}$=272.6 Hz), 123.5 (q, $J_{CF}$=3.0 Hz), 126.1, 130.2, 130.6 (d, $J_{CF}$=3.0 Hz), 131.2 (d, $J_{CF}$=8.0 Hz), 132.2 (d, $J_{CF}$=33.2 Hz), 136.5, 150.9, 162.9 (d, $J_{CF}$=247.5 Hz), 164.2.

2-(3-methylphenyl)-4-(4-fluorobenzyl)-1,2,4-thiadiazolidine-3,5-dione (1g)

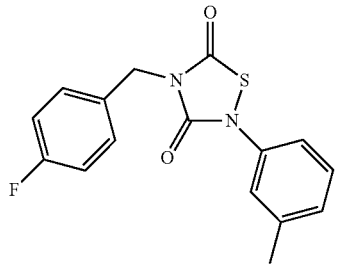 [SMILES: Cc1cccc(-n2sc(=O)n(Cc3ccc(F)cc3)c2=O)c1]

Yield=72%. 1H NMR (400 MHz, CDCl3) δ 2.38 (s, 3H), 4.87 (s, 2H), 7.02-7.06 (m, 2H), 7.08-7.11 (m, 1H), 7.28-7.30 (m, 2H), 7.31-7.33 (m, 1H), 7.48-7.51 (m, 2H). 13C NMR (100 MHz, CDCl3) δ 21.4, 45.4, 115.7 (d, $J_{CF}$=21.6 Hz), 120.6, 124.2, 128.0, 129.3, 131.0 (d, $J_{CF}$=3.2 Hz), 131.1 (d, $J_{CF}$=8.2 Hz), 135.6, 139.8, 151.0, 162.8 (d, $J_{CF}$=247.3 Hz), 165.1

2-(3-chlorophenyl)-4-(4-fluorobenzyl)-1,2,4-thiadiazolidine-3,5-dione (1h)

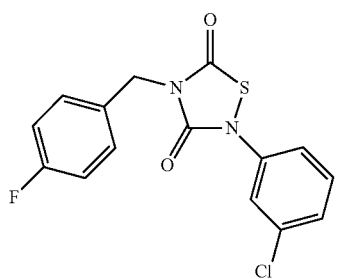 [SMILES: O=c1sn(-c2cccc(Cl)c2)c(=O)n1Cc1ccc(F)cc1]

Yield=60%. 1H NMR (400 MHz, CDCl3) δ 4.88 (s, 2H), 7.02-7.06 (m, 2H), 7.24-7.27 (m, 1H), 7.32-7.39 (m, 2H), 7.47-7.51 (m, 2H), 7.60-7.61 (m, 1H). 13C NMR (100 MHz, CDCl3) δ 45.5, 115.8 (d, $J_{CF}$=21.6 Hz), 121.0, 123.3, 127.0, 130.4, 130.7 (d, $J_{CF}$=24.5 Hz), 131.2 (d, $J_{CF}$=8.3 Hz), 135.3, 136.9, 150.8, 162.8 (d, $J_{CF}$=247.6 Hz), 164.4.

2-(4-methylbenzyl)-4-(4-fluorobenzyl)-1,2,4-thiadiazolidine-3,5-dione (1i)

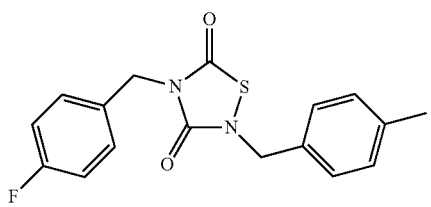 [SMILES: Cc1ccc(Cn2sc(=O)n(Cc3ccc(F)cc3)c2=O)cc1]

Yield=62%. 1H NMR (400 MHz, CDCl3) δ 2.35 (s, 3H), 4.72 (s, 2H), 4.80 (s, 2H), 7.02 (tJ=6.7 Hz, 2H), 7.18 (s, 4H), 7.43-7.47 (m, 2H). 13C NMR (100 MHz, CDCl3) δ 21.2, 45.2, 48.6, 115.6 (d, $J_{CF}$=21.1 Hz), 128.5, 129.7, 130.9 (d, $J_{CF}$=8.0 Hz), 131.1 (d, $J_{CF}$=3.0 Hz), 131.3, 138.9, 152.9, 162.7 (d, $J_{CF}$=247.5 Hz), 165.9.

2-(4-t-butylphenyl)-4-(4-fluorobenzyl)-1,2,4-thiadiazolidine-3,5-dione (S1)

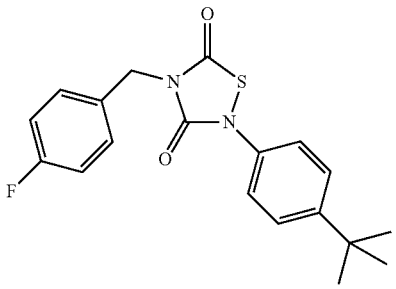 [SMILES: CC(C)(C)c1ccc(-n2sc(=O)n(Cc3ccc(F)cc3)c2=O)cc1]

Yield=81%. 1H NMR (400 MHz, CDCl3) δ 1.32 (s, 9H), 4.87 (s, 2H), 7.01-7.05 (m, 2H). 7.39-7.44 (m, 4H), 7.48-7.51 (m, 2H). 13C NMR (100 MHz, CDCl3) δ 31.2, 34.7, 45.4, 115.7 (d, $J_{CF}$=21.6 Hz), 123.5, 126.5, 131.0 (d, $J_{CF}$=3.2 Hz), 131.2 (d, $J_{CF}$=8.2 Hz), 132.9, 150.6, 151.1, 162.8 (d, $J_{CF}$=247.3 Hz), 165.2.

2-(4-dimethylaminophenyl)-4-(4-fluorobenzyl)-1,2,4-thiadiazolidine-3,5-dione (S2)

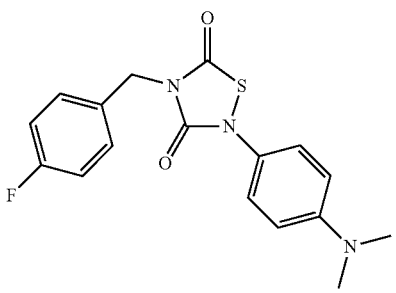 [SMILES: CN(C)c1ccc(-n2sc(=O)n(Cc3ccc(F)cc3)c2=O)cc1]

Yield=35%. 1H NMR (400 MHz, CDCl3) δ 2.83 (s, 6H), 4.90 (s, 2H), 7.03-7.09 (m, 4H), 7.27-7.32 (m, 1H), 7.46-7.51 (m, 3H).

2-p-tolyl-4-benzyl-1,2,4-thiadiazolidine-3,5-dione (2a)

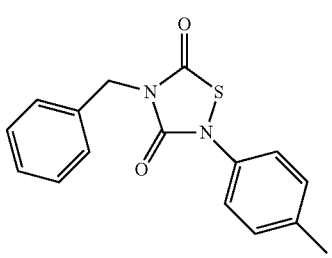 [SMILES: Cc1ccc(-n2sc(=O)n(Cc3ccccc3)c2=O)cc1]

Yield=88%. 1H NMR (400 MHz, CDCl3) δ 2.35 (s, 3H), 4.91 (s, 2H), 7.20 (d, J=8.6 Hz, 2H), 7.26-7.38 (m, 5H) 7.51

(d, J=6.2 Hz, 2H); 13C NMR (100 MHz, CDCl3) δ 21.0, 46.1, 123.6, 128.3, 128.7, 129.1, 130.0, 133.0, 135.0, 137.2, 151.1, 165.2.

2-phenyl-4-benzyl-1,2,4-thiadiazoline-3,5-dione (2b)

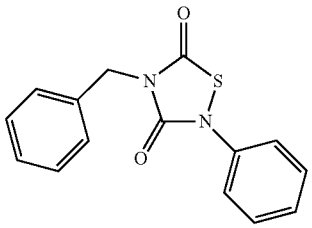 [SMILES: O=c1sn(-c2ccccc2)c(=O)n1Cc1ccccc1]

Yield=81%. 1H NMR (400 MHz, CDCl3) δ 4.92 (s, 2H), 7.26-7.30 (m, 1H), 7.33-7.39 (m, 4H), 7.41-7.43 (m, 1H), 7.50-7.52 (m, 4H). 13C NMR (100 MHz, CDCl3) δ 46.1, 123.4, 126.9, 128.4, 128.8, 129.1, 129.5, 135.0, 135.8, 150.9, 165.0.

2-(4-chlorophenyl)-4-benzyl-1,2,4-thiazolidine-3,5-dione (2c)

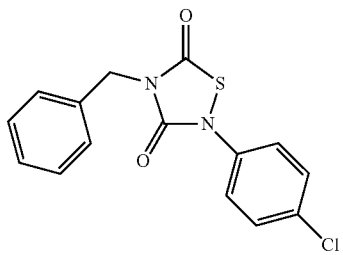 [SMILES: O=c1sn(-c2ccc(Cl)cc2)c(=O)n1Cc1ccccc1]

Yield=60%. 1H NMR (400 MHz, CDCl3) δ 4.91 (s, 2H), 7.33-7.39 (m, 5H), 7.44-7.51 (m, 4H); 13C NMR (100 MHz, CDCl3) δ 46.3, 124.5, 128.8, 129.1, 129.6, 132.5, 134.5, 134.9, 150.9, 164.5

2-(4-methoxyphenyl)-4-benzyl-1,2,4-thiadiazolidine-3,5-dione (2d)

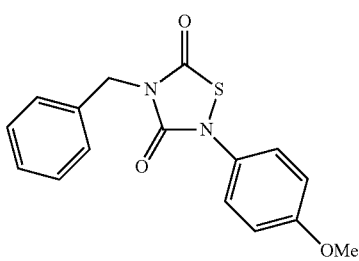 [SMILES: COc1ccc(-n2sc(=O)n(Cc3ccccc3)c2=O)cc1]

Yield=58%. 1H NMR (400 MHz, CDCl3) δ 3.81 (s, 3H), 4.90 (s, 2H), 6.92 (d, J=9.0 Hz, 2H), 7.32-7.39 (m, 5H), 7.49-7.52 (m, 2H). 13C NMR (100 MHz, CDCl3) δ 46.2, 55.6, 114.7, 126.2, 128.1, 128.3, 128.7, 129.1, 135.1, 151.4, 158.8, 165.3.

2-(3,4-dichlorophenyl-4-benzyl-1,2,4-thiadiazolidine-3,5-dione (2e)

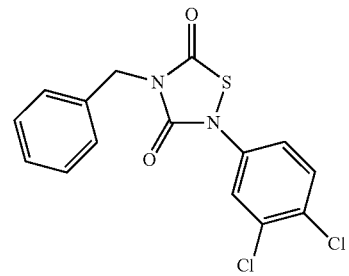 [SMILES: O=c1sn(-c2ccc(Cl)c(Cl)c2)c(=O)n1Cc1ccccc1]

Yield=55%. 1H NMR (400 MHz, CDCl3) δ 4.91 (s, 2H), 7.33-7.38 (m, 4H), 7.46-7.50 (m, 3H), 7.72 (d, J=2.6 Hz, 1H); 13C NMR (100 MHz, CDCl3) δ 46.2, 121.9, 124.7, 128.5, 128.8, 129.1, 130.6, 130.9, 133.5, 134.6, 135.2, 150.7, 164.0.

2-(3-trifluoromethylphenyl-4-benzyl-1,2,4-thiadiazolidine-3,5-dione (2f)

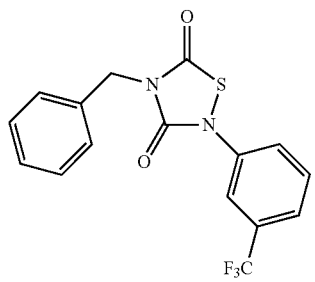 [SMILES: O=c1sn(-c2cccc(C(F)(F)F)c2)c(=O)n1Cc1ccccc1]

Yield=57%. 1H NMR (400 MHz, CDCl3) δ 4.93 (s, 2H), 7.34-7.39 (m, 3H), 7.49-7.57 (m, 4H), 7.68-7.71 (m, 1H), 7.85-7.86 (m, 1H). 13C NMR (100 MHz, CDCl3) δ 46.3, 119.8 (q, $J_{CF}$=3.7 Hz), 123.2 (q, $J_{CF}$=3.7 Hz), 123.3 (q, $J_{CF}$=272.6 Hz), 125.9 (app. d, $J_{CF}$=0.9 Hz), 128.5, 128.8, 129.1, 130.1, 132.0 (q, $J_{CF}$=33.1 Hz), 134.7, 136.5, 150.9, 164.2.

2-(3-methylphenyl)-4-benzyl-1,2,4-thiadiazolidine-3,5-dione (2g)

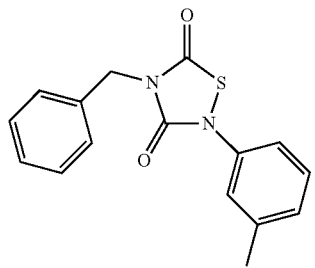 [SMILES: Cc1cccc(-n2sc(=O)n(Cc3ccccc3)c2=O)c1]

Yield=59%. 1H NMR (400 MHz, CDCl3) δ 2.37 (s, 3H), 4.91 (s, 2H), 7.07-7.10 (m, 1H), 7.28-7.29 (m, 2H), 7.32-7.38 (m, 4H), 7.49-7.52 (m, 2H). 13C NMR (100 MHz, CDCl3) δ 21.4, 46.2, 120.6, 124.1, 127.9, 128.4, 128.8, 129.1, 129.3, 135.1, 135.7, 139.7, 151.0, 165.2.

2-(3-chlorophenyl)-4-benzyl-1,2,4-thiadiazolidine-3,5-dione (2h)

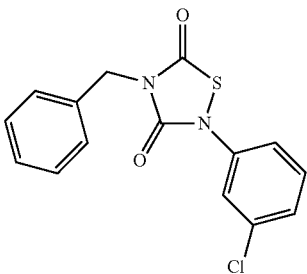 [SMILES: O=c1sn(-c2cccc(Cl)c2)c(=O)n1Cc1ccccc1]

Yield=71%. 1H NMR (400 MHz, CDCl3) δ 4.91 (s, 2H), 7.23-7.26 (m, 1H), 7.31-7.40 (m, 5H), 7.49-7.51 (m, 2H), 7.61-7.62 (m, 1H). 13C NMR (100 MHz, CDCl3) δ 46.3, 120.9, 123.3, 126.9, 128.5, 128.9, 129.1, 130.4, 134.8, 135.3, 137.0, 150.8, 164.4.

2-(4-methylbenzyl)-4-benzyl-1,2,4-thiadiazolidine-3,5-dione (2i)

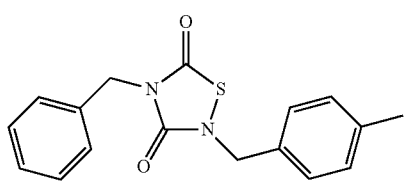 [SMILES: Cc1ccc(Cn2sc(=O)n(Cc3ccccc3)c2=O)cc1]

Yield=59%. 1H NMR (400 MHz, CDCl3) δ 2.35 (s, 3H), 4.73 (s, 2H), 4.84 (s, 2H), 7.18 (app. s, 4H), 7.31-7.37 (m, 3H), 7.44-7.46 (m, 2H). 13C NMR (100 MHz, CDCl3) δ 21.2, 45.9, 48.6, 128.3, 128.6, 128.7, 128.9, 129.7, 131.4, 135.2, 138.8, 153.1, 165.9.

2-(4-t-butylphenyl)-4-benzyl-1,2,4-thiadiazolidine-3,5-dione (S3)

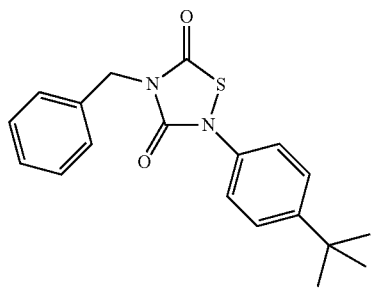 [SMILES: CC(C)(C)c1ccc(-n2sc(=O)n(Cc3ccccc3)c2=O)cc1]

Yield=79%. 1H NMR (400 MHz, CDCl3) δ 1.32 (s, 9H), 4.91 (s, 2H), 7.32-7.38 (m, 3H), 7.42 (app. s, 4H), 7.49-7.52 (m, 2H). 13C NMR (100 MHz, CDCl3) δ 31.2, 34.7, 46.2, 123.4, 126.5, 128.4, 128.8, 129.1, 133.0, 135.1, 150.5, 151.2, 165.2.

2-p-tolyl-4-(4-chlorobenzyl)-1,2,4-thiadiazolidine-3,5-dione (3)

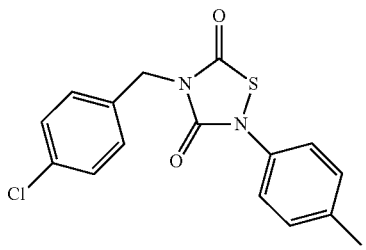 [SMILES: Cc1ccc(-n2sc(=O)n(Cc3ccc(Cl)cc3)c2=O)cc1]

Yield=84%. 1H NMR (400 MHz, CDCl3) δ 2.35 (s, 3H), 4.86 (s, 2H), 7.20-7.22 (m, 2H), 7.31-7.37 (m, 4H), 7.43-7.45 (m, 2H). 13C NMR (100 MHz, CDCl3) δ 21.0, 45.4, 123.7, 128.9, 130.1, 130.6, 132.9, 133.5, 134.4, 137.4, 150.9, 165.2.

2-phenyl-4-(4-chlorobenzyl)-1,2,4-thiadiazolidine-3,5-dione (S4)

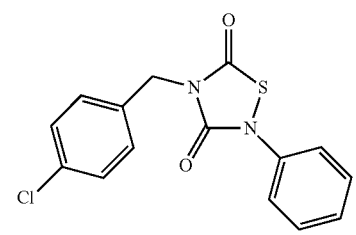 [SMILES: O=c1sn(-c2ccccc2)c(=O)n1Cc1ccc(Cl)cc1]

Yield=61%. 1H NMR (400 MHz, CDCl3) δ 4.87 (s, 2H), 7.26-7.33 (m, 3H), 7.40-7.49 (m, 4H), 7.49-7.51 (m, 2H). 13C NMR (100 MHz, CDCl3) δ 45.4, 123.4, 127.1, 129.0, 129.5, 130.6, 133.4, 134.5, 135.6, 150.8, 165.0.

2-(4-chlorophenyl)-4-(4-chlorobenzyl)-1,2,4-thiadiazolidine-3,5-dione (S5)

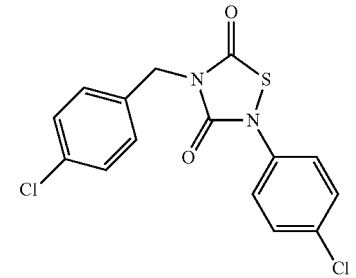 [SMILES: O=c1sn(-c2ccc(Cl)cc2)c(=O)n1Cc1ccc(Cl)cc1]

Yield=69%. 1H NMR (400 MHz, CDCl3) δ 4.86 (s, 2H), 7.31-7.33 (m, 2H), 7.37-7.39 (m, 2H), 7.43-7.46 (m, 4H).

13C NMR (100 Hz, CDCl3) δ 45.5, 124.5, 128.8, 129.0, 129.03, 129.96, 130.6, 132.6, 133.3, 134.2, 134.6, 150.8, 164.5.

2-(4-methoxyphenyl)-4-(4-chlorobenzyl)-1,2,4-thiadiazolidine-3,5-dione (S6)

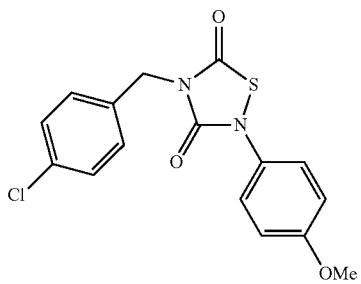 [SMILES: COc1ccc(-n2sc(=O)n(Cc3ccc(Cl)cc3)c2=O)cc1]

Yield=25%. 1H NMR (400 MHz, CDCl3) δ 3.81 (s, 3H), 4.86 (s, 2H), 6.91-6.93 (m, 2H), 7.31-7.33 (m, 2H), 7.35-7.38 (m, 2H), 7.43-7.45 (m, 2H). 13C NMR (100 MHz, CDCl3) δ 45.4, 55.5, 114.2, 114.7, 126.2, 127.9, 128.9, 130.6, 133.5, 134.4, 151.3, 158.9, 165.3.

2-(3,4-dichlorophenyl)-4-(4-chlorobenzyl)-1,2,4-thiadiazolidine-3,5-dione (S7)

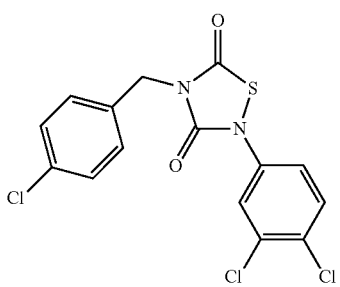 [SMILES: O=c1sn(-c2ccc(Cl)c(Cl)c2)c(=O)n1Cc1ccc(Cl)cc1]

Yield=37%. 1H NMR (400 MHz, CDCl3) δ 4.87 (s, 2H), 7.32-7.36 (m, 3H), 7.42-7.49 (m, 3H), 7.70 (d, J=2.6 Hz, 1H). 13C NMR (100 MHz, CDCl3) δ 45.6, 122.0, 124.8, 129.1, 130.6, 130.9, 131.0, 133.1, 133.6, 134.7, 135.1, 150.7.

2-(4-methylbenzyl)-4-(4-chlorobenzyl)-1,2,4-thiadiazolidine-3,5-dione (S8)

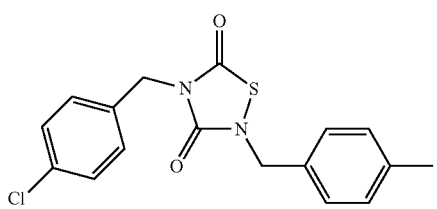 [SMILES: Cc1ccc(Cn2sc(=O)n(Cc3ccc(Cl)cc3)c2=O)cc1]

Yield=69%. 1H NMR (400 MHz, CDCl3) δ 2.35 (s, 3H), 4.72 (s, 2H), 4.79 (s, 2H), 7.17 (app. s, 4H), 7.30-7.32 (m, 2H), 7.38-7.40 (m, 2H). 13C NMR (100 MHz, CDCl3) δ 21.1, 45.2, 48.5, 128.5, 128.9, 129.7, 130.3, 131.2, 133.6, 134.3, 138.9, 152.8, 165.8.

2-p-tolyl-4-(4-methylbenzyl)-1,2,4-thiadiazolidine-3,5-dione (4)

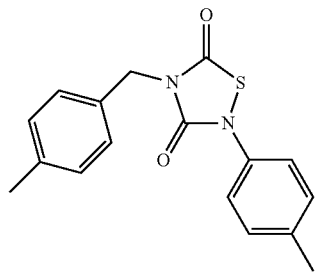

Yield=74%. 1H NMR (400 MHz, CDCl3) δ 2.34 (s, 3H), 2.35 (s, 3H), 4.87 (s, 2H), 7.15-7.21 (m, 4H), 7.35-7.41 (m, 4H). 13C NMR (100 MHz, CDCl3) δ 21.0, 21.2, 45.9, 123.7, 129.1, 129.4, 130.0, 132.2, 133.2, 137.2, 138.2, 151.1, 165.2.

2-phenyl-4-(4-methylbenzyl)-1,2,4-thiadiazolidine-3,5-dione (S9)

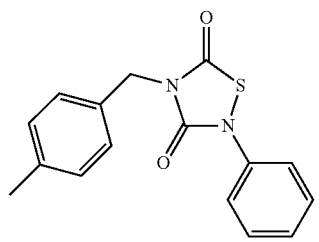 [SMILES: Cc1ccc(Cn2c(=O)sn(-c3ccccc3)c2=O)cc1]

Yield=74%. 1H NMR (400 MHz, CDCl3) δ 2.34 (s, 3H), 4.88 (s, 2H), 7.16 (d, J=7.8 Hz, 2H), 7.25-7.29 (m, 1H), 7.39-7.43 (m, 4H), 7.50 (d, J=7.8 Hz, 2H). 13C NMR (100 MHz, CDCl3) δ 21.2, 45.9, 123.4, 126.9, 129.1, 129.4, 129.5, 132.1, 135.8, 138.2, 151.0, 165.0.

2-(4-chlorophenyl)-4-(4-methylbenzyl)-1,2,4-thiadiazolidine-3,5-dione (S10)

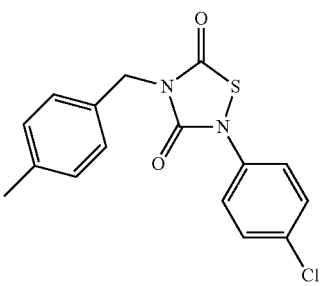 [SMILES: Cc1ccc(Cn2c(=O)sn(-c3ccc(Cl)cc3)c2=O)cc1]

Yield=80%. 1H NMR (400 MHz, CDCl3) δ 2.34 (s, 3H), 4.87 (s, 2H), 7.16 (d, J=7.8 Hz, 2H), 7.35-7.40 (m, 4H), 7.44-7.46 (m, 2H). 13C NMR (100 MHz, CDCl3) δ 21.2, 46.0, 124.5, 129.1, 129.4, 129.5, 131.9, 132.4, 134.4, 138.4, 150.9, 164.5.

2-(4-methoxyphenyl)-4-(4-methylbenzyl)-1,2,4-thiadiazolidine-3,5-dione (S11)

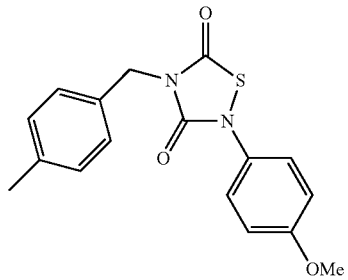 [SMILES: COc1ccc(-n2sc(=O)n(Cc3ccc(C)cc3)c2=O)cc1]

Yield=69%. 1H NMR (400 MHz, CDCl3) δ 2.34 (s, 3H), 3.81 (s, 3H), 4.87 (s, 2H), 6.91-6.93 (m, 2H), 7.16 (d, J=7.9 Hz, 2H), 7.36-7.41 (m, 4H). 13C NMR (100 MHz, CDCl3) δ 21.1, 45.9, 55.5, 114.7, 126.1, 128.1, 129.1, 129.4, 132.2, 138.2, 151.4, 158.8, 165.3.

2-(3,4-dichlorophenyl)-4-(4-methylbenzyl)-1,2,4-thiadiazolidine-3,5-dione (S12)

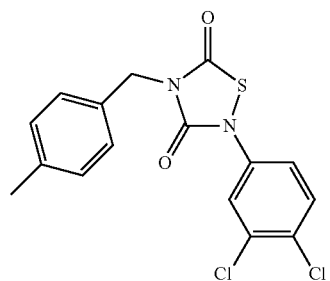 [SMILES: Cc1ccc(Cn2c(=O)sn(-c3ccc(Cl)c(Cl)c3)c2=O)cc1]

Yield=67%. 1H NMR (400 MHz, CDCl3) δ 2.34 (s, 3H), 4.87 (s, 2H), 7.17 (d, J=7.8 Hz, 2H), 7.35 (dd, J=2.6, 8.8 Hz, 1H), 7.36 (m, 2H), 7.46 (d, J=8.8 Hz, 1H), 7.71 (d, J=2.6 Hz, 1H). 13C NMR (100 MHz, CDCl3) δ 21.2, 46.1, 121.9, 124.7, 129.1, 129.5, 130.6, 130.9, 131.7, 133.5, 135.2, 138.5, 150.8, 164.1.

2,4-bis(4-methylbenzyl)-1,2,4-thiadiazolidine-3,5-dione (S13)

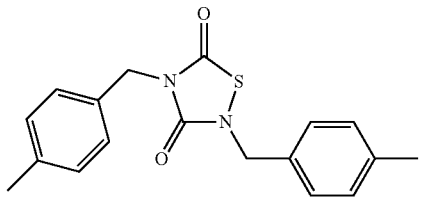

Yield=78%. 1H NMR (400 MHz, CDCl3) δ 2.33 (s, 3H), 2.35 (s, 3H), 4.71 (s, 2H), 4.80 (s, 2H), 7.13-7.15 (m, 2H), 7.17 (app. s, 4H), 7.34-7.36 (m, 2H). 13C NMR (100 MHz, CDCl3) δ 21.10, 21.12, 45.7, 48.5, 128.5, 128.9, 129.3, 129.6, 131.4, 132.3, 138.0, 138.7, 153.0, 165.9.

2-p-tolyl-4-(3-chlorobenzyl)-1,2,4-thiadiazolidine-3,5-dione (5)

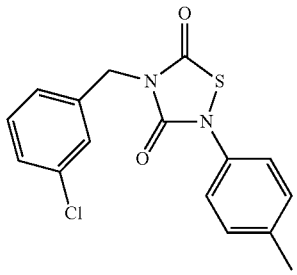 [SMILES: Cc1ccc(-n2sc(=O)n(Cc3cccc(Cl)c3)c2=O)cc1]

Yield=68%. 1H NMR (400 MHz, CDCl3) δ 2.36 (s, 3H), 4.87 (s, 2H), 7.20-7.32 (m, 4H), 7.36-7.39 (m, 3H), 7.48-7.49 (m, 1H). 13C NMR (100 MHz, CDCl3) δ 21.0, 45.5, 123.7, 127.3, 128.7, 129.2, 129.6, 130.06, 130.10, 133.0, 134.6, 136.9, 137.4, 150.9, 165.2.

2-phenyl-4-(3-chlorobenzyl)-1,2,4-thiadiazolidine-3,5-dione (S14)

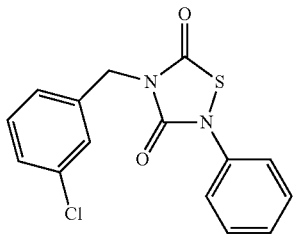 [SMILES: O=c1sn(-c2ccccc2)c(=O)n1Cc1cccc(Cl)c1]

Yield=88%. 1H NMR (400 MHz, CDCl3) δ 4.88 (s, 2H), 7.29-7.31 (m, 3H), 7.38-7.44 (m, 3H), 7.49-7.53 (m, 3H). 13C NMR (100 MHz, CDCl3) δ 45.5, 123.5, 127.1, 127.3, 128.7, 129.1, 129.2, 129.6, 130.1, 134.7, 135.7, 136.8, 150.8, 164.9.

2-(4-t-butylphenyl)-4-(3-chlorobenzyl)-1,2,4-thiadiazolidine-3,5-dione (S15)

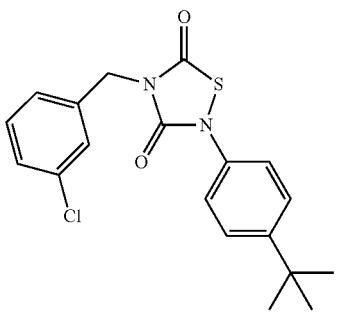 [SMILES: CC(C)(C)c1ccc(-n2sc(=O)n(Cc3cccc(Cl)c3)c2=O)cc1]

Yield=72%. 1H NMR (400 MHz, CDCl3) δ 1.32 (s, 9H), 4.87 (s, 2H), 7.28-7.30 (m, 2H), 7.37-7.40 (m, 1H), 7.42-7.43

(m, 4H), 7.49-7.50 (m, 1H). 13C NMR (100 MHz, CDCl3) δ 31.2, 34.7, 45.5, 123.5, 126.5, 127.3, 128.7, 129.2, 130.1, 132.9, 134.6, 136.9, 150.6, 150.9, 165.2.

2-m-tolyl-4-(3-chlorobenzyl)-1,2,4-thiadiazolidine-3,5-dione (S16)

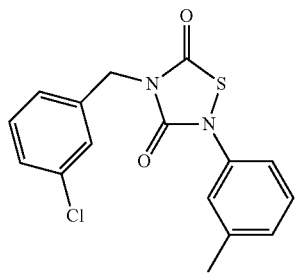 [SMILES: Cc1cccc(-n2sc(=O)n(Cc3cccc(Cl)c3)c2=O)c1]

Yield=59%. 1H NMR (400 MHz, CDCl3) δ 2.38 (s, 3H), 4.87 (s, 2H), 7.08-7.11 (m, 1H), 7.26-7.30 (m, 4H), 7.31-7.33 (m, 1H), 7.37-7.39 (m, 1H), 7.48-7.49 (m, 1H). 13C NMR (100 MHz, CDCl3) δ 21.4, 45.5, 120.6, 124.2, 127.3, 128.0, 128.7, 129.2, 129.3, 130.1, 134.7, 135.6, 136.9, 139.8, 150.8, 165.1.

2-(3-chlorophenyl)-4-(3-chlorobenzyl)-1,2,4-thiadiazolidine-3,5-dione (S17)

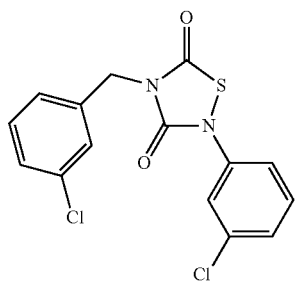 [SMILES: O=c1sn(-c2cccc(Cl)c2)c(=O)n1Cc1cccc(Cl)c1]

Yield=81%. 1H NMR (400 MHz, CDCl3) δ 4.87 (s, 2H), 7.24-7.32 (m, 4H), 7.34-7.39 (m, 2H), 7.47-7.48 (m, 1H), 7.61-7.62 (m, 1H). 13C NMR (100 MHz, CDCl3) δ 45.6, 121.0, 123.3, 127.1, 127.3, 128.8, 129.2, 130.1, 130.5, 134.7, 135.3, 136.6, 136.9, 150.7, 164.4.

2-(3-trifluoromethylphenyl)-4-(3-chlorobenzyl)-1,2,4-thiadiazolidine-3,5-dione (S18)

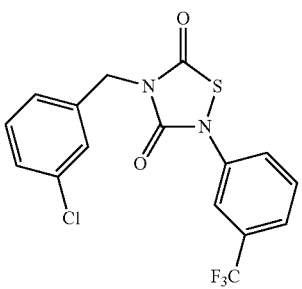 [SMILES: O=c1sn(-c2cccc(C(F)(F)F)c2)c(=O)n1Cc1cccc(Cl)c1]

Yield=67%. 1H NMR (400 MHz, CDCl3) δ 4.88 (s, 2H), 7.27-7.33 (m, 2H), 7.37-7.42 (m, 1H), 7.48-7.49 (m, 1H), 7.54-7.58 (m, 2H), 7.69-7.71 (m, 1H), 7.84 (br s, 1H). 13C NMR (100 MHz, CDCl3) δ 45.7, 119.9 (q, $J_{CF}$=4.0 Hz), 123.4 (q, $J_{CF}$=271.6), 123.5 (q, $J_{CF}$=4.0 Hz), 126.1, 127.3, 128.9, 129.2, 129.6, 130.2 (d, $J_{CF}$=3.0 Hz), 132.2 (q, $J_{CF}$=33.2 Hz), 134.7, 136.4, 136.5, 150.8, 164.2.

2-(4-methylphenyl)-4-(3-methylbenzyl)-1,2,4-thiadiazolidine-3,5-dione (6)

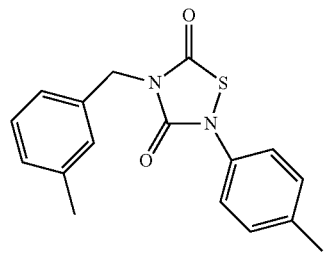 [SMILES: Cc1ccc(-n2sc(=O)n(Cc3cccc(C)c3)c2=O)cc1]

Yield=78%. 1H NMR (400 MHz, CDCl3) δ 2.35 (s, 6H), 4.87 (s, 2H), 7.13-7.14 (m, 1H), 7.19-7.24 (m, 3H), 7.29-7.31 (m, 2H), 7.36-7.38 (m, 2H). 13C NMR (100 MHz, CDCl3) δ 21.0, 21.4, 46.2, 123.7, 126.2, 128.7, 129.1, 129.8, 130.1, 133.2, 135.0, 137.2, 138.5, 151.2, 165.2.

2-phenyl-4-(3-methylbenzyl)-1,2,4-thiadiazolidine-3,5-dione (S19)

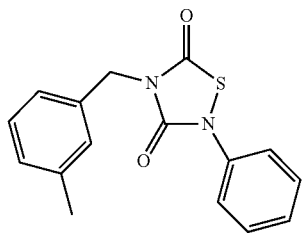 [SMILES: Cc1cccc(Cn2c(=O)sn(-c3ccccc3)c2=O)c1]

Yield=76%. 1H NMR (400 MHz, CDCl3) δ 2.36 (s, 3H), 4.88 (s, 2H), 7.13-7.15 (m, 1H), 7.22-7.27 (m, 2H), 7.28-7.31 (m, 2H), 7.39-7.43 (m, 2H), 7.50-7.53 (m, 2H). 13C NMR (100 MHz, CDCl3) δ 21.4, 46.2, 123.4, 126.2, 127.0, 128.7, 129.2, 129.5, 129.8, 135.0, 135.9, 138.5, 151.0, 165.0.

2-(4-t-butylphenyl)-4-(3-methylbenzyl)-1,2,4-thiadiazolidine-3,5-dione (S20)

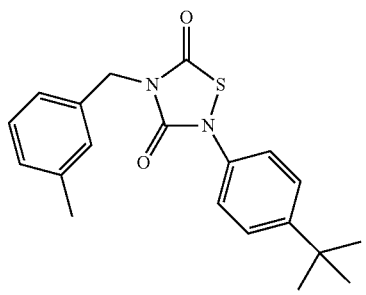 [SMILES: Cc1cccc(Cn2c(=O)sn(-c3ccc(C(C)(C)C)cc3)c2=O)c1]

Yield=70%. 1H NMR (400 MHz, CDCl3) δ 1.32 (s, 9H), 2.35 (s, 3H), 4.88 (s, 2H), 7.13 (br. d, J=7.5 Hz, 1H), 7.23 (d, J=8.0 Hz, 1H), 7.30-7.31 (m, 2H), 7.42 (app. d, J=3.6 Hz, 4H). 13C NMR (100 MHz, CDCl3) δ 21.4, 31.2, 34.6, 46.2, 123.4, 126.2, 126.4, 128.7, 129.1, 129.8, 133.1, 135.0, 138.5, 150.4, 151.2, 165.2.

2-m-tolyl-4-(3-methylbenzyl)-1,2,4-thiadiazolidine-3,5-dione (S21)

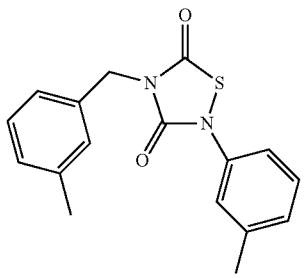 [SMILES: Cc1cccc(Cn2c(=O)sn(-c3cccc(C)c3)c2=O)c1]

Yield=89%. 1H NMR (400 MHz, CDCl3) δ 2.35 (s, 3H), 2.37 (s, 3H), 4.87 (s, 2H), 7.07-7.09 (m, 1H), 7.12-7.14 (m, 1H), 7.22-7.24 (m, 1H), 7.28-7.30 (m, 4H), 7.33-7.34 (m 1H). 13C NMR (100 MHz, CDCl3) δ 21.4, 46.2, 120.5, 124.1, 126.2, 127.9, 128.7, 129.1, 129.3, 129.7, 135.0, 135.7, 138.5, 139.7, 151.1, 165.2.

2-(3-chlorophenyl)-4-(3-methylbenzyl)-1,2,4-thiadiazolidine-3,5-dione (S22)

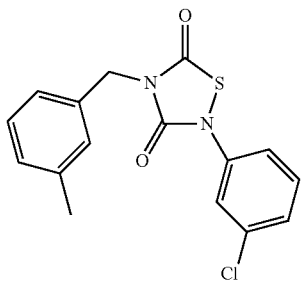 [SMILES: Cc1cccc(Cn2c(=O)sn(-c3cccc(Cl)c3)c2=O)c1]

Yield=66%. 1H NMR (400 MHz, CDCl3) δ 2.35 (s, 3H), 4.87 (s, 2H), 7.13-7.15 (m, 1H), 7.22-7.25 (m, 2H), 7.28-7.31 (m, 2H), 7.31-7.35 (m, 1H), 7.37-7.39 (m, 1H), 7.61-7.62 (m, 1H). 13C NMR (100 MHz, CDCl3) δ 21.3, 46.2, 120.8, 123.2, 126.1, 126.8, 128.7, 129.2, 129.7, 130.3, 134.7, 135.2, 137.0, 138.5, 150.8, 164.4.

2-(3-trifluoromethylphenyl)-4-(3-methylbenzyl)-1,2,4-thiadiazolidine-3,5-dione (S23)

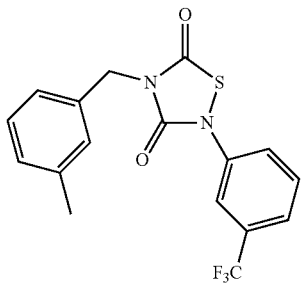 [SMILES: Cc1cccc(Cn2c(=O)sn(-c3cccc(C(F)(F)F)c3)c2=O)c1]

Yield=87%. 1H NMR (400 MHz, CDCl3) δ 2.36 (s, 3H), 4.89 (s, 2H), 7.14-7.16 (m, 1H), 7.23-7.27 (m, 1H), 7.29-7.30 (m, 2H), 7.52-7.56 (m, 2H), 7.68-7.71 (m, 1H), 7.85 (br app. s, 1H). 13C NMR (100 MHz, CDCl3) δ 21.4, 46.4, 119.9 (q, $J_{CF}$=4.0 Hz), 123.3 (q, $J_{CF}$=4.0 Hz), 123.4 (q, $J_{CF}$=272.6 Hz), 126.0, 126.2, 128.8, 129.3, 129.7, 130.1, 132.1 (q, $J_{CF}$=33.2 Hz), 134.7, 136.6, 138.6, 151.0, 164.3.

2-p-tolyl-4-(4-methoxybenzyl)-1,2,4-thiadiazolidine-3,5-dione (7)

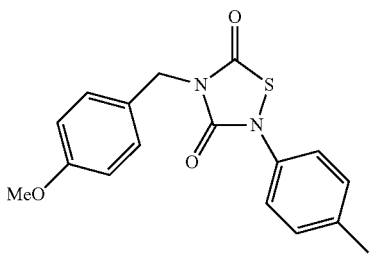 [SMILES: COc1ccc(Cn2c(=O)sn(-c3ccc(C)cc3)c2=O)cc1]

Yield=65%. 1H NMR (400 MHz, CDCl3) δ 2.35 (s, 3H), 3.80 (s, 3H), 4.85 (s, 2H), 6.86-6.88 (m, 2H), 7.19-7.21 (m, 2H), 7.35-7.37 (m, 2H), 7.44-7.46 (m, 2H). 13C NMR (100 MHz, CDCl3) δ 21.0, 45.6, 55.3, 114.1, 123.7, 127.4, 129.5, 130.0, 130.7, 133.1, 137.2, 151.1, 159.7, 165.2.

2-phenyl-4-(4-methoxybenzyl)-1,2,4-thiadiazolidine-3,5-dione (S24)

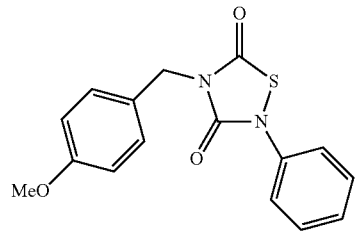 [SMILES: COc1ccc(Cn2c(=O)sn(-c3ccccc3)c2=O)cc1]

Yield=83%. 1H NMR (400 MHz, CDCl3) δ 3.83 (s, 3H), 4.89 (s, 2H), 6.89-6.93 (m, 2H), 7.28-7.36 (m, 2H), 7.40-7.55 (m, 6H). 13C NMR (100 MHz, CDCl3) δ 45.7, 55.3, 114.1, 123.4, 126.9, 127.3, 129.0, 129.5, 130.7, 135.8, 151.0, 159.7, 165.0.

2-(4-chlorophenyl)-4-(4-methoxybenzyl)-1,2,4-thiadiazolidine-3,5-dione (S25)

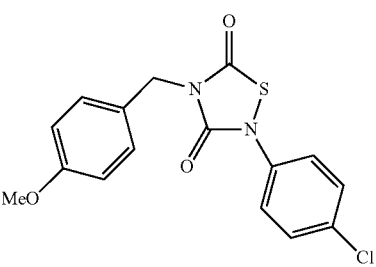 [SMILES: COc1ccc(Cn2c(=O)sn(-c3ccc(Cl)cc3)c2=O)cc1]

Yield=77%. 1H NMR (400 MHz, CDCl3) δ 3.79 (s, 3H), 4.84 (s, 2H), 6.86-6.88 (m, 2H), 7.36-7.38 (m, 2H), 7.43-7.46

(m, 4H). 13C NMR (100 MHz, CDCl3) δ 45.8, 55.3, 114.1, 124.5, 127.1, 129.5, 130.7, 132.4, 134.4, 150.9, 159.7, 164.5.

2-(4-methoxyphenyl)-4-(4-methoxybenzyl)-1,2,4-thiadiazolidine-3,5-dione (S26)

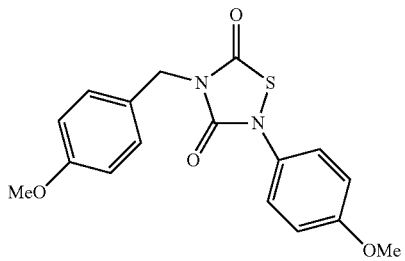 [SMILES: COc1ccc(Cn2c(=O)sn(-c3ccc(OC)cc3)c2=O)cc1]

Yield=63%. 1H NMR (400 MHz, CDCl3) δ 3.80 (s, 3H), 3.81 (s, 3H), 4.84 (s, 2H), 6.86-6.92 (m, 4H), 7.36-7.38 (m, 2H), 7.44-7.46 (m, 2H). 13C NMR (100 MHz, CDCl3) δ 45.7, 55.2, 55.5, 114.0, 114.7, 126.1, 127.4, 128.1, 130.7, 151.5, 158.8, 159.7, 165.3.

2-(3,4-dichlorophenyl)-4-(4-methoxybenzyl)-1,2,4-thiadiazolidine-3,5-dione (S27)

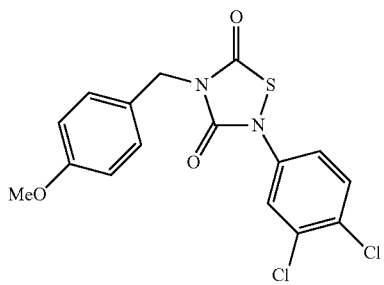 [SMILES: COc1ccc(Cn2c(=O)sn(-c3ccc(Cl)c(Cl)c3)c2=O)cc1]

Yield=67%. 1H NMR (400 MHz, CDCl3) δ 3.80 (s, 3H), 4.85 (s, 2H), 6.87-6.89 (m, 2H), 7.35 (dd, J=2.6, 8.7 Hz, 1H), 7.42-7.47 (m, 3H), 7.71 (d, J=2.6 Hz, 1H). 13C NMR (100 MHz, CDCl3) δ 45.9, 55.3, 114.2, 122.0, 124.8, 126.9, 130.7, 130.9, 133.5, 135.2, 150.8, 159.8, 164.1.

2-(4-methylbenzyl)-4-(4-methoxybenzyl)-1,2,4-thiadiazolidine-3,5-dione (S28)

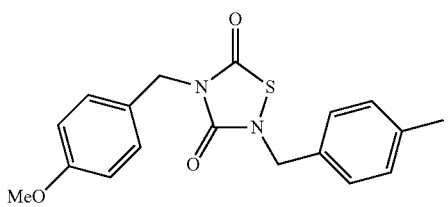 [SMILES: COc1ccc(Cn2c(=O)sn(Cc3ccc(C)cc3)c2=O)cc1]

Yield=36%. 1H NMR (400 MHz, CDCl3) δ 2.35 (s, 3H), 3.80 (s, 3H), 4.72 (s, 2H), 4.78 (s, 2H), 6.85-6.88 (m, 2H), 7.17 (s, 4H), 7.40-7.42 (m, 2H). 13C NMR (100 MHz, CDCl3) δ21.2, 45.5, 48.5, 55.3, 114.0, 127.5, 128.5, 129.7, 130.5, 131.4, 138.8, 153.1, 159.6, 166.0.

2-p-tolyl-4-(3,4-dichlorobenzyl)-1,2,4-thiadiazolidine-3,5-dione (8)

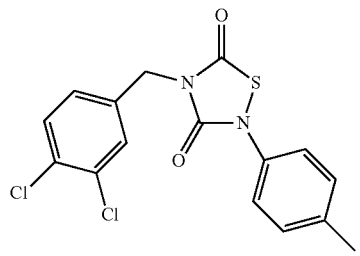 [SMILES: Cc1ccc(-n2sc(=O)n(Cc3ccc(Cl)c(Cl)c3)c2=O)cc1]

Yield=72%. 1H NMR (400 MHz, CDCl3) δ 2.39 (s, 3H), 4.87 (s, 2H), 7.24-7.29 (m, 2H), 7.36-7.41 (m, 3H), 7.45-7.47 (m, 1H), 7.63-7.64 (m, 1H). 13C NMR (100 MHz, CDCl3) δ 21.0, 44.9, 123.8, 128.6, 130.1, 130.8, 131.2, 132.8, 132.9, 135.1, 137.6, 150.9, 165.1.

2-phenyl-4-(3,4-dichlorobenzyl)-1,2,4-thiadiazolidine-3,5-dione (S29)

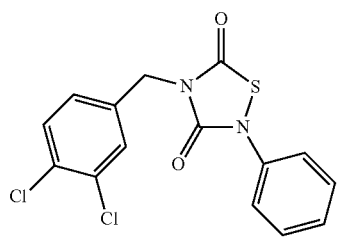 [SMILES: O=c1sn(-c2ccccc2)c(=O)n1Cc1ccc(Cl)c(Cl)c1]

Yield=78%. 1H NMR (400 MHz, CDCl3) δ 4.85 (s, 2H), 7.28-7.32 (m, 1H), 7.34-7.36 (m, 1H), 7.41-7.44 (m, 3H), 7.49-7.52 (m, 2H), 7.60-7.61 (m, 1H). 13C NMR (100 MHz, CDCl3) δ 44.9, 123.5, 127.2, 128.6, 129.6, 130.8, 131.1, 132.8, 132.9, 134.9, 135.6, 150.7, 164.9.

2-(4-chlorophenyl)-4-(3,4-dichlorobenzyl)-1,2,4-thiadiazolidine-3,5-dione (S30)

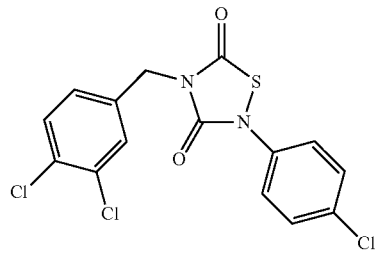 [SMILES: O=c1sn(-c2ccc(Cl)cc2)c(=O)n1Cc1ccc(Cl)c(Cl)c1]

Yield=76%. 1H NMR (400 MHz, CDCl3) δ 4.84 (s, 2H), 7.33 (dd, J=2.0, 8.2 Hz, 1H), 7.38-7.42 (m, 3H), 7.44-7.47 (m, 2H), 7.59 (d, J=2.0 Hz, 1H). 13C NMR (100 MHz, CDCl3) δ 45.0, 124.6, 128.6, 129.7, 130.8, 131.1, 132.8, 133.0, 134.1, 134.8, 150.7, 164.5.

2-(4-methoxyphenyl)-4-(3,4-dichlorobenzyl)-1,2,4-thiadiazolidine-3,5-dione (S31)

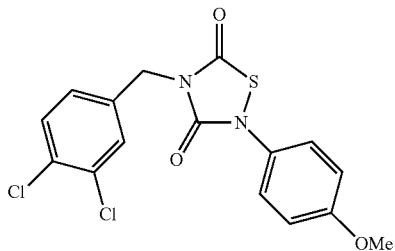 [SMILES: COc1ccc(-n2sc(=O)n(Cc3ccc(Cl)c(Cl)c3)c2=O)cc1]

Yield=80%. 1H NMR (400 MHz, CDCl3) δ 3.82 (s, 3H), 4.83 (s, 2H), 6.92-6.94 (m, 2H), 7.33-7.38 (m, 3H), 7.42 (d, J=8.2 Hz, 1H), 7.60 (d, J=2.0 Hz, 1H). 13C NMR (100 MHz, CDCl3) δ 44.9, 55.6, 114.8, 126.2, 127.8, 128.6, 130.7, 131.1, 132.8, 132.9, 135.1, 151.1, 159.0, 165.2.

2-(3,4-dichlorophenyl)-4-(3,4-dichlorobenzyl)-1,2,4-thiadiazolidine-3,5-dione (S32)

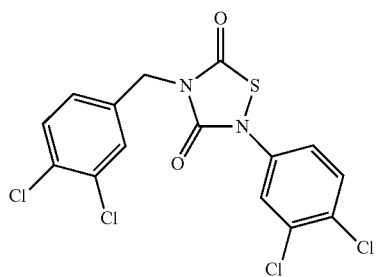 [SMILES: O=c1sn(-c2ccc(Cl)c(Cl)c2)c(=O)n1Cc1ccc(Cl)c(Cl)c1]

Yield=26%. 1H NMR (400 MHz, CDCl3) δ 4.84 (s, 2H), 7.32-7.36 (m, 2H), 7.42-7.49 (m, 2H), 7.58 (d, J=2.0 Hz, 1H), 7.70 (d, J=2.6 Hz, 1H). 13C NMR (100 MHz, CDCl3) δ 45.1, 122.1, 124.9, 128.6, 130.9, 131.0, 131.1, 132.99, 133.05, 133.6, 134.6, 134.9, 150.5, 164.0.

2-(4-methylbenzyl)-4-(3,4-dichlorobenzyl)-1,2,4-thiadiazolidine-3,5-dione (S33)

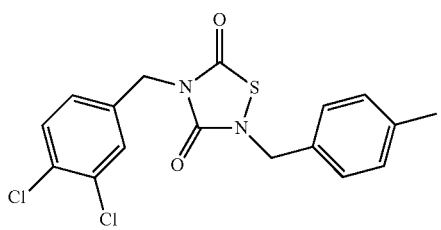 [SMILES: Cc1ccc(Cn2sc(=O)n(Cc3ccc(Cl)c(Cl)c3)c2=O)cc1]

Yield=35%. 1H NMR (400 MHz, CDCl3) δ 2.36 (s, 3H), 4.73 (s, 2H), 4.77 (s, 3H), 7.16-7.18 (m, 4H), 7.29 (dd, J=2.1, 8.2 Hz, 1H), 7.41 (d, J=8.2 Hz, 1H), 7.55 (d, J=2.0 Hz, 1H).

13C NMR (100 MHz, CDCl3) δ 21.2, 44.7, 48.7, 128.4, 129.0, 129.3, 129.8, 130.7, 130.9, 131.2, 132.7, 132.9, 135.2, 139.0, 152.7, 165.8.

2-p-tolyl-4-(4-t-butylbenzyl)-1,2,4-thiadiazolidine-3,5-dione (S34)

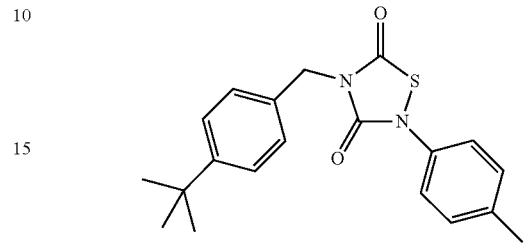

Yield=72%. 1H NMR (400 MHz, CDCl3) δ 1.31 (s, 9H), 2.35 (s, 3H), 4.87 s, 2H), 7.19-7.21 (m, 2H), 7.36-7.38 (m, 4H), 7.43-7.45 (m, 2H). 13C NMR (100 MHz, CDCl3) δ 21.0, 31.3, 34.6, 45.8, 123.7, 125.7, 128.9, 130.0, 132.2, 133.2, 137.2, 151.2, 151.4, 165.2.

2-phenyl-4-(4-t-butylbenzyl)-1,2,4-thiadiazolidine-3,5-dione (S35)

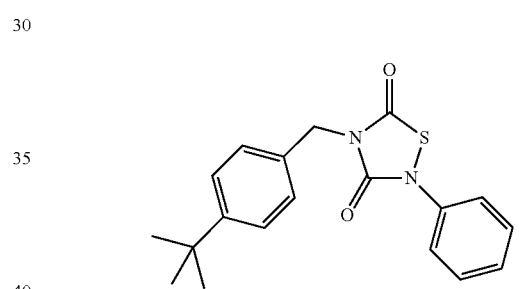

Yield=81%. 1H NMR (400 MHz, CDCl3) δ 1.31 (s, 9H), 4.88 (s, 2H), 7.25-7.29 (m, 1H), 7.36-7.45 (m, 6H), 7.50-7.52 (m, 2H). 13C NMR (100 MHz, CDCl3) δ 31.3, 34.6, 45.9, 123.4, 125.7, 126.9, 128.9, 129.5, 132.1, 135.9, 151.1, 151.4, 165.0.

2-(4-t-butylphenyl)-4-(4-t-butylbenzyl)-1,2,4-thiadiazolidine-3,5-dione (S36)

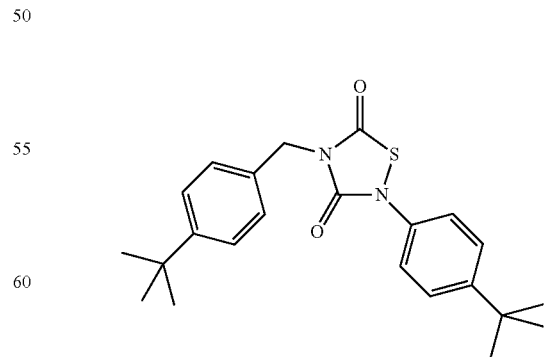

Yield=62%. 1H NMR (400 MHz, CDCl3) δ 1.30 (s, 9H), 1.31 (s, 9H), 4.88 (s, 2H), 7.36-7.38 (m, 2H), 7.41-7.42 (m, 4H), 7.43-7.45 (m, 2H). 13C NMR (100 MHz, CDCl3) δ

31.2, 31.3, 34.6, 34.7, 45.8, 123.4, 125.7, 126.5, 129.0, 132.1, 133.0, 150.4, 151.2, 151.4, 165.3.

2-butyl-4-(4-fluorobenzyl)-1,2,4-thiadiazolidine-3,5-dione (9a)

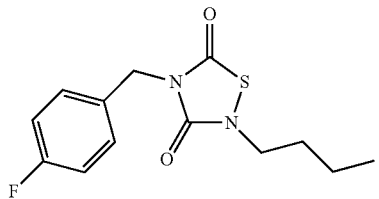 [SMILES: CCCCn1sc(=O)n(Cc2ccc(F)cc2)c1=O]

Yield=65%. 1H NMR (400 MHz, CDCl3) δ 0.94 (t, J=7.4 Hz, 3H), 1.31-1.40 (m, 2H), 1.57-1.64 (m, 2H), 3.61 (t, J=7.2 Hz, 2H), 4.78 (s, 2H), 6.98-7.02 (m, 2H), 7.41-7.44 (m, 2H). 13C NMR (100 MHz, CDCl3) δ 13.4, 19.5, 30.6, 44.7, 45.1, 115.5 (d, J=21.5 Hz), 130.8 (d, J=8.3 Hz), 131.1 (d, J=3.3 Hz), 152.8, 162.6 (d, J=247.0 Hz), 165.9.

2-ethyl-4-(4-fluorobenzyl)-1,2,4-thiadiazolidine-3,5-dione (9b)

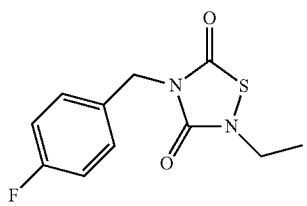 [SMILES: CCn1sc(=O)n(Cc2ccc(F)cc2)c1=O]

Yield=72%. 1H NMR (400 MHz, CDCl3) δ 1.26 (t, J=7.2 Hz, 3H), 3.70 (q, J=7.2 Hz, 2H), 4.80 (s, 2H), 7.01-7.05 (m, 2H), 7.44-7.47 (m, 2H). 13C NMR (100 MHz, CDCl3) δ 13.8, 40.1, 45.2, 115.6 (d, $J_{CF}$=21.1 Hz), 130.9 (d, $J_{CF}$=8.0 Hz), 131.2 (d, $J_{CF}$=3.0 Hz), 152.7, 162.7 (d, $J_{CF}$=247.5 Hz), 165.9.

2-p-tolyl-4-methyl-1,2,4-thiadiazolidine-3,5-dione (10a)

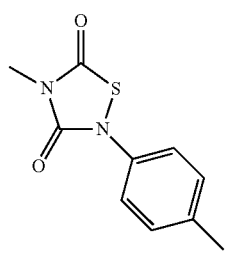

Yield=69%. 1H NMR (400 MHz, CDCl3) δ 2.36 (s, 3H), 3.29 (s, 3H), 7.10-7.12 (m, 1H), 7.21-7.24 (m, 2H), 7.36-7.38 (m, 2H). 13C NMR (100 MHz, CDCl3) δ 21.0, 28.7, 123.9, 129.6, 130.1, 133.1, 137.4, 151.4, 165.5.

2-ethyl-4-methyl-1,2,4-thiadiazolidine-3,5-dione (10b)

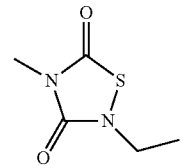

Yield=76%. 1H NMR (400 MHz, CDCl3) δ 1.24 (t, J=7.2 Hz, 3H), 3.17 (s, 3H), 3.67 (q, J=7.2 Hz, 2H). 13C NMR (100 MHz, CDCl3) δ 13.9, 28.5, 40.1, 153.0, 166.2.

2-butyl-4-methyl-1,2,4-thiadiazolidine-3,5-dione (10c)

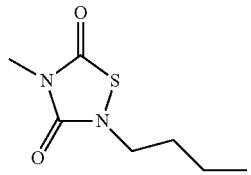

Yield=75%. 1H NMR (400 MHz, CDCl3) δ 0.87 (t, J=7.3 Hz, 3H), 1.25-1.34 (m, 2H), 1.51-1.58 (m, 2H), 3.11 (s, 3H), 3.55-3.58 (m, 2H). 13C NMR (100 MHz, CDCl3) δ 13.3, 19.3, 28.2, 30.5, 44.4, 153.0, 165.9.

2-t-butyl-4-methyl-1,2,4-thiadiazolidine-3,5-dione (10d)

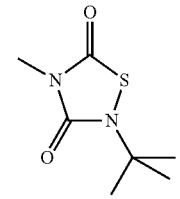

Yield=90%. 1H NMR (400 MHz, CDCl3) δ 1.55 (s, 9H), 3.14 (s, 3H). 13C NMR (100 Hz, CDCl3) δ 28.0, 28.6, 59.1, 152.5, 166.1.

2-p-tolyl-4-butyl-1,2,4-thiadiazolidine-3,5-dione (11a)

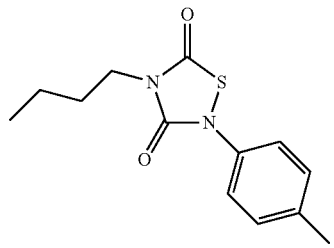 [SMILES: CCCCn1c(=O)sn(-c2ccc(C)cc2)c1=O]

Yield=75%. 1H NMR (400 MHz, CDCl3) δ 0.97 (t, J=7.4 Hz, 3H), 1.35-1.45 (m, 2H), 1.68-1.75 (m, 2H), 2.35 (s, 3H), 3.74-3.78 (m, 2H), 7.20-7.22 (m, 2H), 7.37-7.39 (m, 2H). 13C NMR (100 MHz, CDCl3) δ 13.6, 19.9, 21.0, 29.8, 42.7, 123.7, 130.1, 133.3, 137.1, 151.3, 165.3.

2-ethyl-4-butyl-1,2,4-thiadiazolidine-3,5-dione (11b)

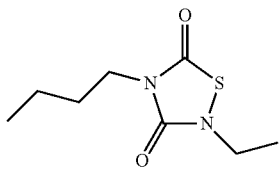

Yield=75%. 1H NMR (400 MHz, CDCl3) δ 0.92 (t, J=7.4 Hz, 3H), 1.25 (t, J=7.2 Hz, 3H), 1.29-1.38 (m, 2H), 1.60-1.67 (m, 2H), 3.64-3.69 (m, 4H). 13C NMR (100 MHz, CDCl3) δ 13.5, 13.7, 19.8, 29.7, 39.9, 42.4, 153.0, 166.0; anal. (C8H14N2O2S); CHN 2,4-dibutyl-1,2,4-thiadiazolidine-3,5-dione (11c)

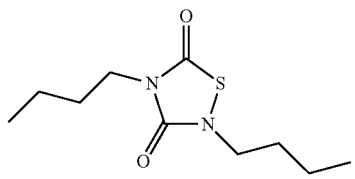

Yield=72%. 1H NMR (400 MHz, CDCl3) δ 0.93 (t, J=7.4 Hz, 3H), 0.94 (t, J=7.4 Hz, 3H), 1.29-1.40 (m, 4H), 1.57-1.69 (m, 4H), 3.61 (t, J=7.2 Hz, 2H), 3.66 (t, J=7.4 Hz, 2H). 13C NMR (100 MHz, CDCl3) δ 13.5, 13.6, 19.6, 19.9, 29.8, 30.7, 42.5, 44.6, 153.2, 166.1.

2-t-butyl-4-butyl-1,2,4-thiadiazolidine-3,5-dione (11d)

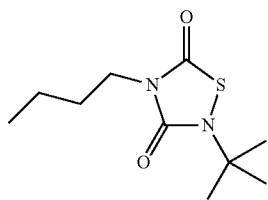

Yield=70%. 1H NMR (400 MHz, CDCl3) δ 0.94 (t, J=7.4 Hz, 3H), 1.32-1.39 (m, 2H), 1.54 (s, 9H), 1.59-1.67 (m, 2H), 3.63 (t, J=7.4 Hz, 2H). 13C NMR (100 MHz, CDCl3) δ 13.6, 19.9, 28.5, 29.8, 42.0, 59.1, 152.5, 166.0.

2-p-tolyl-4-isobutyl-1,2,4-thiadiazolidine-3,5-dione (12a)

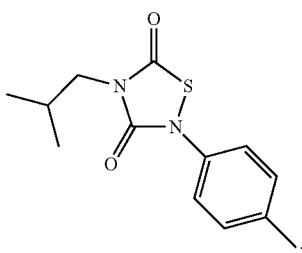 [SMILES: Cc1ccc(-n2sc(=O)n(CC(C)C)c2=O)cc1]

Yield=65%. 1H NMR (400 MHz, CDCl3) δ 0.97 (s, 3H), 0.99 (s, 3H), 2.16-2.23 (m, 1H), 2.36 (s, 3H), 3.59 (d, J=7.4 Hz, 2H), 7.21-7.23 (m, 2H), 7.37-7.39 (m, 2H). 13C NMR (100 MHz, CDCl3) δ 20.0, 21.0, 27.2, 49.9, 123.7, 130.1, 133.3, 137.2, 151.5, 165.6.

2-ethyl-4-isobutyl-1,2,4-thiadiazolidine-3,5-dione (12b)

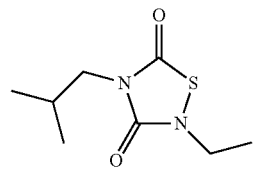

Yield=70%. 1H NMR (400 MHz, CDCl3) δ 0.90 (s, 3H), 0.92 (s, 3H), 1.25 (t, J=7.2 Hz, 3H), 2.08-2.15 (m, 1H), 3.47 (d, J=7.5 Hz, 2H), 3.67 (q, J=7.2 Hz, 2H). 13C NMR (100 MHz, CDCl3) δ 13.7, 19.8, 27.1, 39.9, 49.6, 153.2, 166.2.

2-butyl-4-isobutyl-1,2,4-thiadiazolidine-3,5-dione (12c)

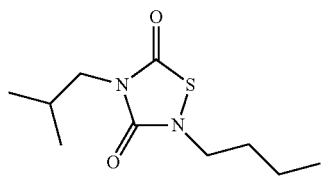

Yield=73%. 1H NMR (400 MHz, CDCl3) δ 0.92 (s, 3H), 0.94 (s, 3H), 0.95 (t, J=7.3 Hz, 3H), 1.35-1.40 (m, 2H), 1.59-1.66 (m, 2H), 2.11-2.18 (m, 1H), 3.50 (d, J=7.5 Hz, 2H), 3.63 (t, J=7.20 Hz, 2H). 13C NMR (100 MHz, CDCl3) δ 13.5, 19.6, 19.8, 27.2, 30.7, 44.6, 49.7, 153.4, 166.3.

2-t-butyl-4-isobutyl-1,2,4-thiadiazolidine-3,5-dione (12d)

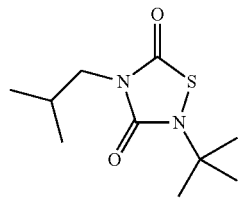

Yield=68%. 1H NMR (400 MHz, CDCl3) δ 0.91 (s, 3H), 0.93 (s, 3H), 1.55 (s, 9H), 2.07-2.18 (m, 1H), 3.46 (d, J=7.5 Hz, 2H). 13C NMR (100 MHz, CDCl3) δ 19.9, 27.2, 28.5, 49.2, 59.1, 152.8, 166.2.

2-ethyl-4-(2-methoxyethyl)-1,2,4-thiadiazolidine-3,5-dione (13)

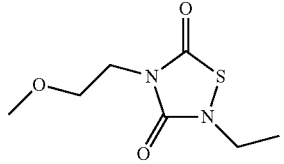

Yield=70%. 1H NMR (400 MHz, CDCl3) δ 1.25 (t, J=7.2 Hz, 3H), 3.34 (s, 3H), 3.60 (t, J=5.6 Hz, 2H), 3.67 (q, J=7.2

Hz, 2H), 3.86 (t, J=5.6 Hz, 2H). 13C NMR (100 MHz, CDCl3) δ 13.7, 40.0, 41.6, 58.6, 68.6, 152.8, 166.1; anal. (C7H12N2O3S.1/2H2O); CHN 3-(4-methylbenzyl)-1-p-tolylimidazolidine-2,4-dione (14)

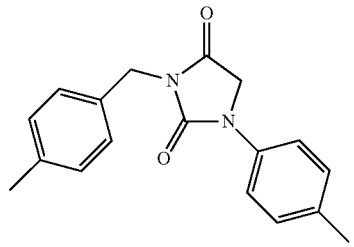

Ethyl bromoacetate (4.0 g, 30.0 mmol) was added to a solution of p-toluidine (2.1 g, 20 mmol) and sodium acetate (2.1 g, 26 mmol) in ethanol (26 mL). The resulting solution was warmed to 80° C. and stirred for 1 h before being cooled to room temperature. The reaction was quenched with water (20 mL) and the aqueous fraction extracted with ethyl acetate (3×20 mL). The organic fractions were combined, dried (MgSO4) and filtered, and the solvent was removed under reduced pressure. Silica chromatography (0-20% ethyl acetate/hexane) provided ethyl 2-(p-tolylamino)acetate as a pale oil (1.9 g, 50%). Ethyl 2-(p-tolylamino)acetate (260 mg, 1.4 mmol) was dissolved in toluene (5 mL). Methyl benzylisocyanate (200 mg, 1.4 mmol) was added to this solution. The mixture was heated to reflux and stirred for 5 h, until TLC analysis demonstrated that the reaction was complete. The reaction mixture was then cooled to room temperature, and the solvent was removed under reduced pressure. Silica chromatography (0-20% ethyl acetate/hexane) provided ethyl 2-[3-(4-methylbenzyl)-1-p-tolylureido]acetate as a pale oil (455 mg, 98%). Ethyl 2-[3-(4-methylbenzyl)-1-p-tolylureido]acetate (455 mg, 1.3 mmol) was dissolved in THF (10 mL) and added dropwise to a solution of NaH (68 mg, 2.8 mmol) in THF (10 mL) at 0° C. The reaction mixture was allowed to warm to room temperature slowly and stirred for 18 h before the reaction was quenched with water (5 mL). The aqueous fraction was then extracted with dichloromethane (3×20 mL). The organic fractions were combined, dried (MgSO4), and filtered, and the solvent was removed under reduced pressure. Column chromatography (0-20% ethyl acetate/hexane) provided 14 as a white solid.

Yield=93%. 1H NMR (400 MHz, CDCl3) δ 2.33 (s, 6H), 4.25 (s, 2H), 4.71 (s, 2H), 7.13-7.15 (m, 2H), 7.16-7.18 (m, 2H), 7.36-7.38 (m, 2H), 7.40-7.43 (m, 2H). 13C NMR (100 MHz, CDCl3) δ 20.7, 21.1, 42.4, 50.0, 118.5, 129.0, 129.4, 129.8, 132.9, 134.2, 135.0, 137.9, 154.1, 168.2.

1-benzyl-3-p-tolyl-1H-pyrrole-2,5-dione (15)

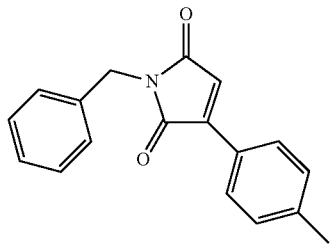 [SMILES: Cc1ccc(C2=CC(=O)N(Cc3ccccc3)C2=O)cc1]

A solution of bromomaleic anhydride (1 g, 5.7 mmol) and benzyl amine (0.7 mL, 6.8 mmol) in acetic acid (15 mL) was warmed to 50° C. and stirred overnight. The reaction was then cooled to room temperature, diluted with CH2Cl2 (50 mL) and washed with NaHCO3 (3×25 mL) and brine (25 mL). The organic layer was then dried (MgSO4), filtered and the solvent removed under reduced pressure. The residue was purified using gradient flash chromatography (0-100% ethyl acetate in pet ether) to provide 1-benzyl-3-bromo-1H-pyrrole-2,5-dione (18). 1H NMR (400 MHz, CDCl3) δ 4.71 (s, 2H), 6.87 (s, 2H), 7.26-7.37 (m, 5H). A stirred solution of 1-benzyl-3-bromo-1H-pyrrole-2,5-dione (0.26 g, 1.0 mmol) and p-tolylboronic acid (0.16 g, 1.2 mmol) in dioxane (10 mL) was degassed with a stream of nitrogen for 10 minutes before being treated with CsF (0.39 g, 2.6 mmol) and Cl2Pd (dppf).CH2Cl2 (0.05 g, 0.06 mmol). The reaction was stirred at room temperature for 1 h then warmed to 40° C. for 1 h. The mixture was then cooled, diluted with CH2Cl2 (30 mL) and filtered through a pad of celite. The filtrate was concentrated under reduced pressure and purified using gradient flash chromatography (0-10% ethyl acetate in pet ether) to provide the title compound 15.

1H NMR (400 MHz, CDCl3) δ 2.40 (s, 3H), 4.73 (s, 2H), 6.68 (s, 1H), 7.24-7.34 (m, 5H), 7.38-7.40 (m, 2H), 7.82-7.84 (m, 2H). 13C NMR (100 MHz, CDCl3) δ 21.6, 41.6, 122.7, 126.0, 127.8, 128.5, 128.6, 128.7, 129.7, 136.5, 141.8, 143.9, 170.2, 170.6.

Reaction of 1a with Propanethiol

An NMR sample was prepared containing 1a (15 mg, 0.05 mmol) and propanethiol (8 µL, 0.1 mmol) in CDCl3 (0.8 mL). Proton NMR spectrum were run at intervals, and complete consumption of 1a was observed after 5 days. The solvent was then removed under reduced pressure to remove excess propanethiol and the sample redissolved in CDCl3 for further analysis.

1H NMR (400 MHz, CDCl3) δ 1.00 (t, J=7.3 Hz, 3H), 1.64-1.69 (m, 2H), 2.31 (s, 3H), 2.76 (t, J=7.1 Hz, 2H), 5.16 (s, 2H), 6.99-7.04 (m, 2H), 7.12-7.14 (m, 2H), 7.30-7.34 (m, 2H), 7.39-7.41 (m, 2H), 10.69 (s, 1H). 13C NMR (100 MHz, CDCl3) δ 12.9, 20.7, 22.0, 40.9, 46.9, 115.5 (d, J=22 Hz), 120.5, 122.5, 128.9 (d, J=8.0 Hz), 129.5, 129.9, 132.0 (d, J=3.0 Hz), 134.2, 134.6, 150.4, 162.2 (d, J=246.3 Hz), 172.9.

All compounds were evaluated using the FCPIA assay as a primary screen to determine IC$_{50}$ values for inhibition of Gαo binding to both RGS4 and RGS8 (the closest relative to RGS4 based upon sequence homology). 1a was also found to suppress Ca2+ responses to GPCRs in a manner unrelated to its activity at RGS proteins. A subset of the new ligands was also assessed for this off target effect.

CCG-50014 (1a) was confirmed as a potent inhibitor of RGS4 with excellent selectivity over RGS8. Retaining the 4-fluorobenzyl R1 group and varying R2 led to both more (e.g., 1d) and less (e.g., 1g) potent and selective compounds. A 3-substituent on the R2 aryl ring was associated with reduced RGS4 potency as compared to unsubstituted and 4-substituted analogues (e.g., 1f, 1g, 1h cf. 1b, 1c, 1d). This trend is repeated across a number of the series where R1 is held constant and R2 is varied. A 3,4-dichlorophenyl group as R2 generally resulted in low potency at RGS4 and relatively low selectivity (e.g., 1e, 2e). In contrast, a 4-methyl substituent was more often associated with high affinity and high selectivity at RGS4, with a number displaying >1000-fold selectivity versus RGS8 (e.g., 3, 4, 5, and 7). Replacement of the phenyl group by benzyl at R2 (1i, 2i) did not improve activity at RGS4 but did reduce RGS8 activity, resulting in each compound having near 3 orders of magnitude selectivity.

In fact, of the compounds discussed so far, that is, retaining a benzyl or substituted benzyl at R1, 1i and 2i were the most selective.

Variation in the aryl groups of R1 and R2 has therefore led to the discovery of a number of ligands with high potency and excellent selectivity. However, the uniformly high lipophilicity (Clog P typically >4) of these ligands resulted in only moderate solubility in aqueous solution. To address this, analogues in which one or both R groups were replaced with short alkyl chains were prepared. In the former series, where one aryl group was replaced by alkyl (9a,b, 10a, 11a, and 12a), potency and selectivity at RGS4 were retained. Making both R groups short alkyl chains (10b-d, 11b-d, and 12b-d) substantially improved solubility (complete solubility at 500 μM) while also providing the most consistently selective group of compounds yet developed (all >1000-fold selective). 11b exhibited good potency at RGS4 (IC50 14.4 nM), near 6000-fold selectivity, and high solubility. As a means to even further enhance solubility of this compound, analogues containing ether side chains were considered, and the ether analogue of 11b was prepared. This compound (13) retained good potency (56 nM) and excellent selectivity (>600-fold).

Figure 20:
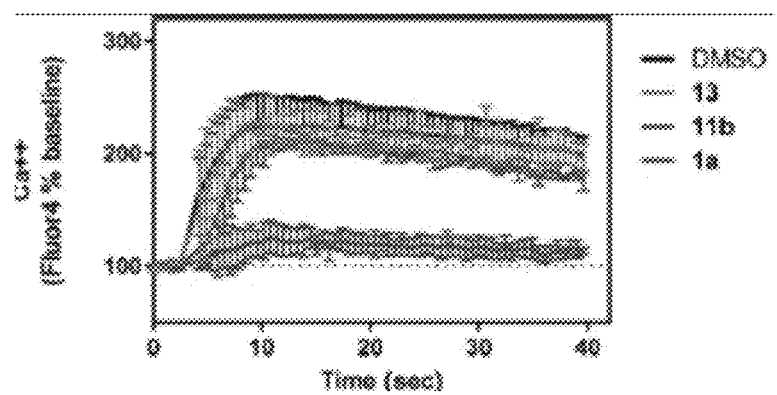
FIG. 20 shows the effect of compounds shown in Tables 5 and 6 on carbachol-simulated Ca++ responses.

The effects of 1a, 11b, and 13 were tested on the Ca2+ transient induced by M3 muscarinic receptors in HEK293T cells. Compound Ia at 10 μM nearly completely abolished the carbachol-induced Ca2+ transient (FIG. 20), while 11b and 13 had no effect. The action of 1a on this response cannot be through effects on RGS proteins since HEK cells express minimal levels of functional RGS proteins (Clark et al., FEBS Lett. 2007, 581, 764-770).

1a reacts to form an adduct with a cysteine residue on the RGS protein through disulfide bond formation (Blazer et al., Biochemistry 2011, 50, 3181-3192). The present invention is not limited to a particular mechanism. Indeed, an understanding of the mechanism is not necessary to practice the invention. Nonetheless, the proposed mechanism (below) is analogous to that proposed by Nasim and Crooks for the ring-opening of TDZDs with PPh3.20.

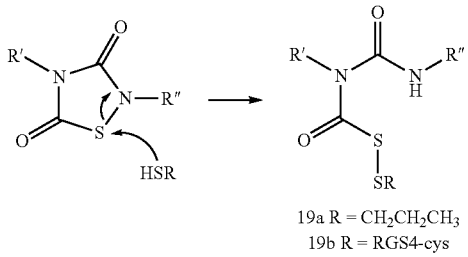

19a R = CH$_2$CH$_2$CH$_3$
19b R = RGS4-cys

To confirm the importance of analogues 14 and 15 were prepared. Compound 14 is the imidazolidine-2,4-dione analogue of 4, while 15 is the maleimide analogue of 2i; 4 and 21 being two of the most potent inhibitors discovered. Neither 14 or 15 displayed activity at RGS4. Also supporting the disulfide bondforming mechanism, the reaction of propane thiol with 1a gives efficiently and cleanly the adduct 19a. 1a is not a general cysteine alkylator, failing to inhibit the cysteine protease papain, indicating selectivity for RGS4 (Blazer et al., Biochemistry 2011, 50, 3181-3192).

Previously, thiadiazolidine-3,5-diones have been reported as having a number of biological effects (Guzman et al., Blood 2007, 110, 4436-4444; Aguilar-Morante et al., PLoS ONE 2010, 5, e13879; Selenica et al., Br. J. Pharmacol. 2007, 152, 959-979, 22-24) including being glycogen synthase kinase 313 (GSK-313) inhibitors with activities in the micromolar range (Martinez et al., J. Med. Chem. 2002, 45, 1292-1299). This latter activity has been contemplated to account, at least in part, for the antidepressant-like effects in mice of the TDZD NP031115 (Rosa et al., Prog. Neuro-Psychopharmacol. Biol. Psychiatry. 2008, 32, 1549-1556). 11b was evaluated as part of that study and was found to be one of the weaker inhibitors (GSK-3β IC50 70 μM) meaning that it has significant selectivity (almost 5000-fold) for RGS4 over GSK-3β.

Example 5

In Vivo Activity

This example describes in vivo activity of compounds of embodiments of the present invention.
Methods:

RGS/Gα binding studies: The binding of biotinylated RGS proteins to fluorescently labeled Gα$_o$ was measured by Flow Cytometry Protein Interaction Assay (FCPIA) method previously described (Roman et al., (2009) J Biomol Screen.; Blazer et al., (2010) Curr Protoc Cytom Chapter 13, Unit 13 11 11-15; Roman et al., (2007) Mol Pharmacol 71, 169-175) as were the measures of compound reversibility.

Single-turnover GAP assay: Experiments were performed as previously described using purified his$_6$-tagged Gα$_o$ (Blazer et al., Biochemistry 50, 3181-3192; Roof et al., (2008) Chem Biol Drug Des 72, 111-119).

Papain inhibition assay: Experiments were performed as previously described (Blazer et al., Biochemistry 50, 3181-3192).

PLCβ inhibition assay: Lipid vesicles containing 200 μM phosphatidylethanolamine, 50 μM PIP$_2$ (Avanti Polar Lipids), and ~4000-8000 cpm [$^3$H]-labeled PIP$_2$ (Perkin-Elmer) per assay were generated by combining the lipids in a borosilicate glass tube and drying the mixture under a stream of nitrogen. Dried lipids were resuspended in 50 mM HEPES pH 7, 80 mM KCl, 2 mM EGTA and 1 mM DTT using a bath sonicator. Activity assays were performed in a final volume of 60 μL containing 3 ng mL$^{-1}$ PLCβ3, 50 mM HEPES pH 7, 80 mM KCl, 15 mM NaCl, 0.83 mM MgCl$_2$, 3 mM DTT, 1 mg mL$^{-1}$ BSA, 2.5 mM EGTA, 0.2 mM EDTA, 2% DMSO, and enough CaCl$_2$ to give a free concentration of ~200 nM. Increasing amounts of CCG-50014 and CCG-203769 were added to the PLCβ3, and incubated for 10-15 minutes. The reactions were initiated by the addition of liposomes and transferred to 30° C. for 5 min. Reactions were terminated by the addition of 100 μL 10 mg mL$^{-1}$ BSA and 200 μL 10% (w/v) ice-cold trichloroacetic acid. The reactions were centrifuged at 8000 g for 5 min to pellet proteins and liposomes, and 200 μL of the resulting supernatant containing free [$^3$H]-IP$_3$ was measured by scintillation counting (Ghosh et al., (2004) Methods Mol Biol 237, 67-75) GSK-3β inhibition assay:

Steady-state GAP Assay: Steady-state hydrolysis of unlabled GTP was measured using malachite green in a receptor-independent assay utilizing a mutant Gα$i_1$ (R178M, A326S) (Zielinski et al., (2009) J Biomol Screen 14, 1195-1206). These mutations facilitate the release of GDP from the enzyme making the GTP hydrolysis step rate-limiting (Lielinski et al., supra). GTP hydrolysis is measured by mixing 6 μM mutant Gαi with 300 μM GTP in the presence or absence of 200 nM RGS4 and CCG-203769 or DMSO (vehicle control). The reaction is allowed to proceed for 2 hours at room temperature and then quenched with an H$_2$SO$_4$/malachite green dye solution. Immediately after addition of malachite green, sodium citrate was added as a colorimetric stablizer. Released inorganic phosphate was measured as an increase in absorbance ($Abs_{630}$) from the complex of phosphate with malachite green (Chang, et al., 2008). Background control samples lacking Gα or RGS were used to determine the rate of non-enzymatic GTP hydrolysis.

Opioid inhibition of cellular cAMP: SH-SY5Y cells were grown in DMEM containing 10% fetal bovine serum and Penicillin (100 units/ml)-Streptomycin (100 μg/ml) under 5% CO2 at 37° C. Cells were plated into 24-well plates to reach ~90% confluency on the day of assay and washed once with fresh serum-free medium. Medium was replaced with 1 mM IBMX (3-isobutyl-1-methylxanthine) in serum-free medium for 15 min at 37° C., and changed to the medium containing 1 mM IBMX, 30 μM forskolin, and 100 nM of either morphine or SNC80 with or without compound CCG-50014 for 5 min at 37° C. Reactions were stopped by replacing the medium with ice-cold 3% perchloric acid and samples were kept at 4° C. for at least 30 min. An aliquot (0.4 ml) from each sample was removed, neutralized with 0.08 ml of 2.5 M $KHCO_3$, vortexed, and centrifuged at 15,000×g for 1 min to pellet the precipitates. Accumulated cAMP was measured by radioimmunoassay in a 10-15 μl aliquot of the supernatant from each sample following the manufacturer's instructions (cAMP radioimmunoassay kit from GE Healthcare, Piscataway, N.J.). Data are from four separate experiments, each carried out in duplicates and calculated as percent inhibition. The basal cAMP accumulation with forskolin alone with or without CCG-50014 did not differ.

Calcium signaling transients: A stable cell line was developed based upon the HEK-293 Flp-In TREx cell line (Invitrogen, Carlsbad, Calif.) that stably express the muscarinic M3 receptor and have human RGS4 expression under doxycycline control. Cells were maintained in DMEM supplemented with 10% fetal bovine serum and Penicillin (100 units/ml)-Streptomycin (100 μg/ml) under 5% CO2 at 37° C. For experiments, cells were split into 96-well black, clear bottom, poly-D-lysine coated microtiter plates (Nunc, Cat. #152037) at a density of 20,000 cells/well in DMEM containing 10% fetal bovine serum and Penicillin (100 units/ml)-Streptomycin (100 μg/ml). RGS4 expression was induced by supplementing the medium with 1 μg/mL doxycycline for 24-48 hours before experimentation. Cells were loaded with Fluo-4 No Wash dye in buffer for 30 minutes at 37° C. Compounds and/or carbachol were added to the wells and the fluorescence intensity was measured using a FlexStation (Molecular Devices, Sunnyvale, Calif.) plate reader. Data analysis was performed by calculating the area under the curve or maximal fluorescence intensity from a 120 second kinetic measurement.

Confocal Microscopy: HEK-293T cells grown to 80-90% confluency in 6-well dishes in DMEM supplemented with 10% fetal bovine serum and Penicillin (100 units/ml)-Streptomycin (100 μg/ml) under 5% CO2 at 37° C. RGS and Go expression was induced by transient co-transfection with either 250 ng of full-length human RGS4 with an N-terminal GFP tag (RGS4pEGFP-C1) or a C-terminal RGS4-GFP (RGS4pDEST47) and 250 ng of pcDNA3.1 or pcDNA with wildtype human Gαo. Cells were split onto poly-D-lysine coated glass coverslips and cultured for 24-48 hours after transfection before live cell imaging. Images were acquired on an Olympus Fluoview 500 confocal microscope with a 60×1.40 numerical aperture (N.A) oil objective. Images were obtained by taking a series of stacks every 0.5 μm through the cell and combining the images into a composite stack. The light source for the fluorescent studies was a 488 nm laser with a 505-525 nm bandpass filter. Images were quantified using NIH ImageJ software version 1.43r.

Figure 21:
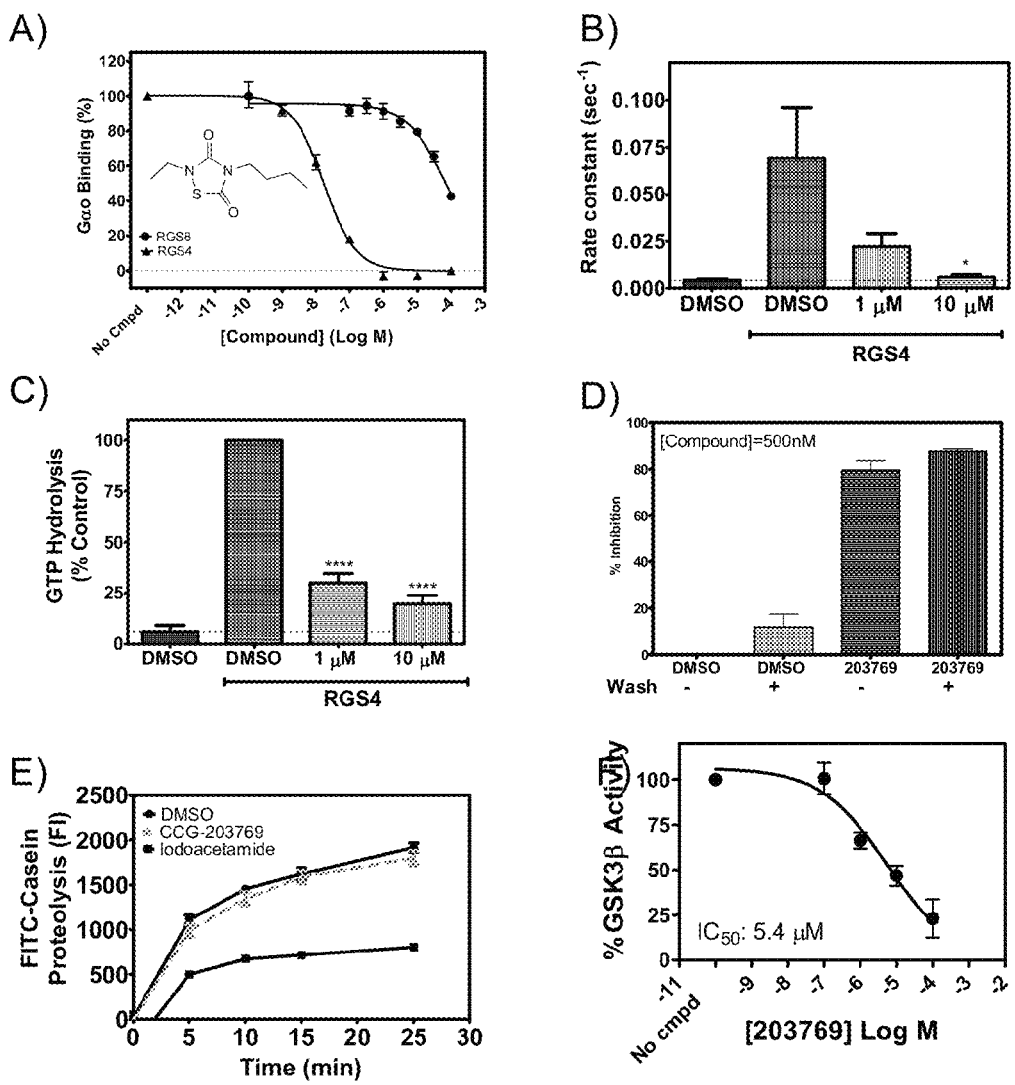
FIG. 21 shows biochemical characterization of RGS inhibitors. A) CCG-203769 inhibits RGS4 and RGS8 binding to $G\alpha_o$ in FCPIA in a concentration-dependent manner. Inset: chemical structure of CCG-203769. See Table 1 for $IC_{50}$ values. CCG-203769 inhibits the RGS-mediated acceleration of GTPase activity by Gαo in both B) single-turnover and C) steady-state GTPase assays. D) CCG-203769 irreversibly inhibits RGS4. E) CCG-203769 and CCG-50014 at a concentration of 30 µM do not inhibit the cysteine protease papain. F) CG-203769 inhibits GSK-3β with an $IC_{50}$ value of 5 µM.

Results:

CCG-203769 is a selective RGS4 inhibitor: CCG-203769 inhibits the RGS4-Gαo protein-protein interaction with an $IC_{50}$ value of 17 nM in the Flow Cytometry Protein Interaction Assay (FCPIA, FIG. 21A). To perform this assay, purified and chemically biotinylated RGS proteins were immobilized on polystyrene beads and incubated with test compound. Gα binding was then probed by mixing the beads with a fluorescently labeled Gα subunit and bead-associated fluorescence is detected in a flow cytometer. CCG-203769 displayed dramatic selectivity for RGS4 over other RGS proteins (Table 1), including a >3000-fold selectivity for RGS4 over the closely related RGS8 (FIG. 21A, Table 7). The compound also potently inhibits the functional effect of RGS4 upon Gαo in single-turnover and steady-state GTPase experiments (FIG. 21B,C). In these experiments, Gαo slowly hydrolyzes GTP and this rate is increased by ~16 fold upon addition of RGS. CCG-203769 was able to inhibit the RGS-mediated stimulation of GTPase activity without inhibiting the basal GTPase activity of the G protein.

CCG-203769 is an irreversible inhibitor of RGS4: RGS4-coated beads were treated with 500 nM CCG-203769, extensively washed and then probed for Gαo binding. Even after removal of the unbound compound, the RGS4 was unable to bind Gαo (FIG. 21D), indicating that this compound acts in an irreversible manner. This data are consistent with the irreversible inhibition of the HTS hit CCG-50014 from which this compound was originally derived (Blazer et al., *Biochemistry* 50, 3181-3192; Roman et al., (2009) *J Biomol Screen*).

CCG-203769 is selective for RGS proteins: Despite this compound's cysteine-modifying mechanism of action, CCG-203769 shows dramatic selectivity for RGS4 over other targets, including molecules with reactive cysteine residues. To demonstrate that this compound does not react with other catalytic cysteine residues, CCG-203769 was tested for the ability to inhibit the cysteine protease papain. Unlike the general thiol-reactive compound iodoacetamide, CCG-203769 at a concentration of 30 μM was unable to inhibit the protease activity of papain (FIG. 21E). Furthermore, the compound was tested against a panel of receptors via collaboration with the NIMH Psycoactive Drug Screening Program. From this it was found that CCG-203769 was able to inhibit the αAR, however it had little to no observable effect upon the muscarinic class of GPCRs.

CCG-203769 and analogs thereof have been previously identified as inhibitors of glycogen synthase kinase 3β (Rosa et al., (2008) Prog Neuropsychopharmacol Biol Psychiatry 32, 1549-1556; Castro et al., (2008) Bioorg Med Chem 16, 495-510; Martinez et al., (2002) J Med Chem 45, 1292-1299). Using a radiometric assay, it was shown that CCG-203769 inhibits GSK-3β with an $IC_{50}$ value of 5 μM (FIG. 21F). The nanomolar potency of this compound upon RGS4 translates to a 300-fold selectivity for RGS4 over GSK-3β.

Figure 22:
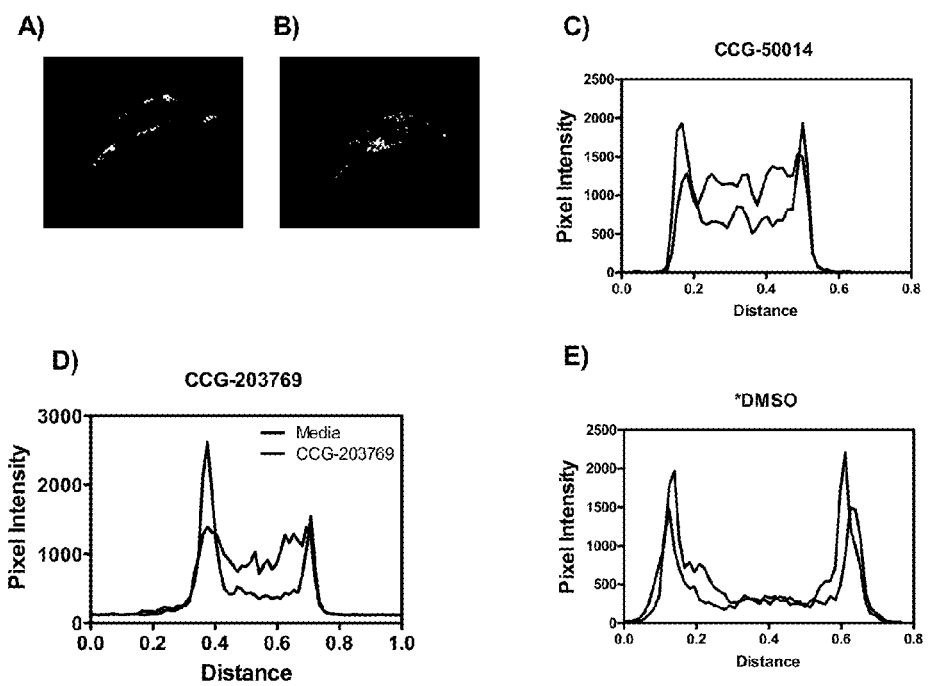
FIG. 22 shows that CCG-50014 and CCG-203769 inhibit the Gαo-dependent membrane translocation of RGS4 in living HEK293T cells. A) RGS4-GFP is expressed as a diffuse cytosolic protein. B) Co-expression of Gαo with RGS4-GFP induces a translocation of the RGS to the cell membrane. C) CCG-50014 (100 µM) or D) CCG-203769 (100 µM) reverses the membrane translocation of the RGS4, while treatment with E) compound vehicle (DMSO) does not have this effect.

Cellular activity of CCG-203769: RGS4 is expressed as a cytosolic protein that translocates to the membrane when co-expressed with high levels of Gαo. CCG-203769 is able to reverse the Gαo-induced membrane translocation of a GFP-tagged RGS4 in living HEK293T cells as visualized by confocal microscopy (FIG. 22). These data indicate that CCG-203769 is actively inhibiting the RGS4-Gαo PPI in living cells.

Figure 23:
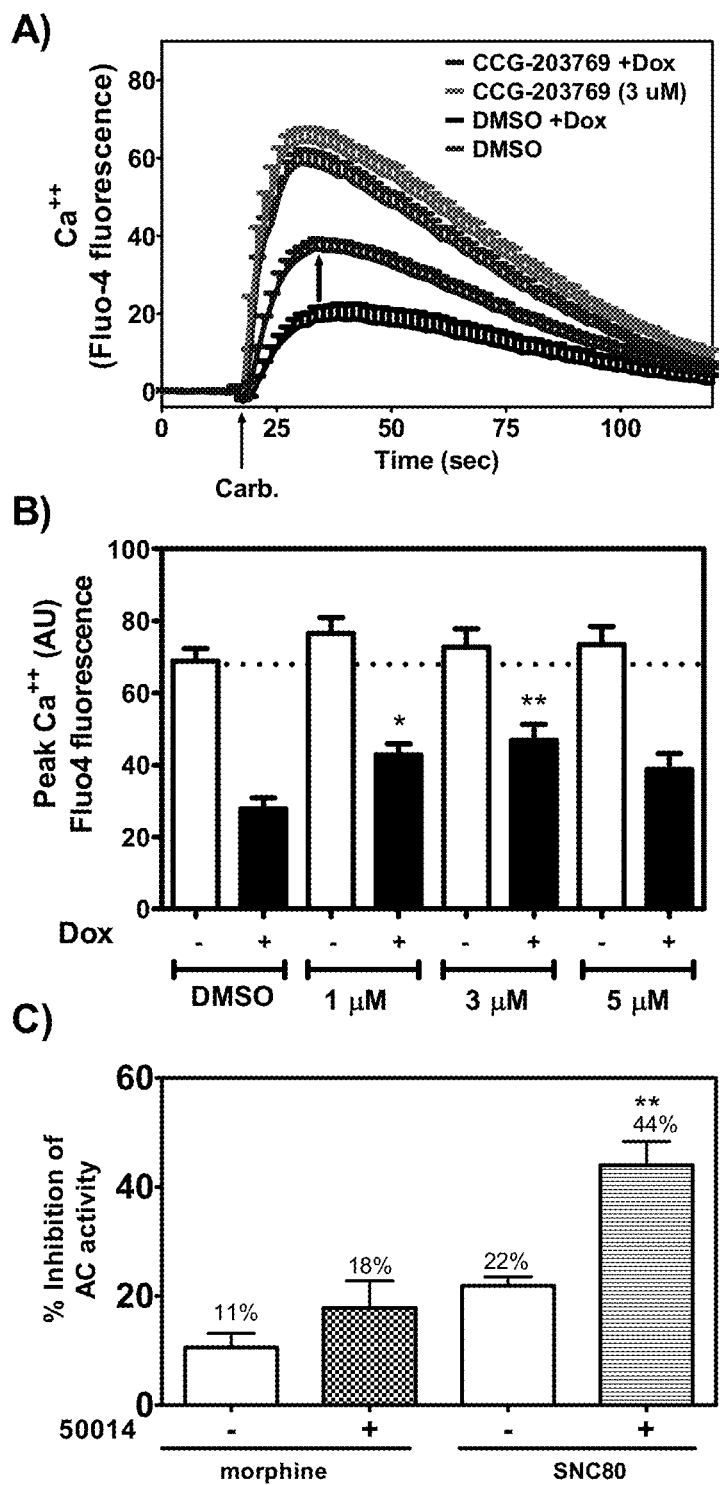
FIG. 23 shows that CCG-203769 and CCG-50014 inhibit RGS proteins in living cells. A) RGS4 inhibits the Gαq-mediated calcium transient invoked by activation of the M3 muscarinic receptor. B) Quantification of the data shown in A, showing that CCG-203769 can partially reverse the RGS-mediated inhibition of M3 signaling. C) In the absence of RGS4 expression, CCG-203769 does not amplify the M3-induced calcium transient. D) CCG-50014 can potentiate the signaling through the δ-opioid receptor in SH-SY5Y neuroblastoma cells.

The functional consequences of inhibiting the RGS4-Galpha PPI with CCG-203769 were further investigated by studying the effects of the compound on M3 muscarinic receptor signaling. A cell line based upon the Flp-in T-REx system (Invitrogen, Carlsbad Calif.) that stably expresses the M3 muscarinic receptor and expresses RGS4 under doxycycline control was generated. Expression of RGS4 in this system suppresses the effect of carbachol by 63% (FIG. 23A). At concentrations of 1 and 3 µM, CCG-203769 does not directly affect the carbachol stimulation of the M3 muscarinic receptor, but does partially reverse the RGS4-mediated muscarinic suppression. This effect has a biphasic concentration-response curve, because at concentrations >3 µM the compound inhibits the magnitude of the $Ca^{2+}$ transient induced by carbachol.

To demonstrate that cellular RGS-inhibitory activity is a class effect, CCG-50014 was tested in the membrane translocation assay (Blazer et al., Biochemistry 50, 3181-3192.) and as presented here, in an orthogonal cell-based assay. Using endogenously expressed RGS and opioid receptors in SH-SY5Y neuroblastoma cells, Wang and colleagues have shown that RGS4 specifically regulates delta-opioid receptor signaling while having little to no effect on mu-opioid receptor signaling (Wang et al., (2009) J Biol Chem 284, 18357-18367). In this system, CCG-50014 at a concentration of 100 µM had no effect on forskolin-stimulation of cAMP production, on MOP or DOP receptor activity. However, CCG-50014 did significantly potentiate the SNC-80 stimulation of DOP. A small potentiation of morphine activity that did not reach statistical significance was also observed, potentially due to inactivation of other RGS proteins in the SH-SY5Y cells that regulate the MOP signal transduction cascade.

Figure 24:
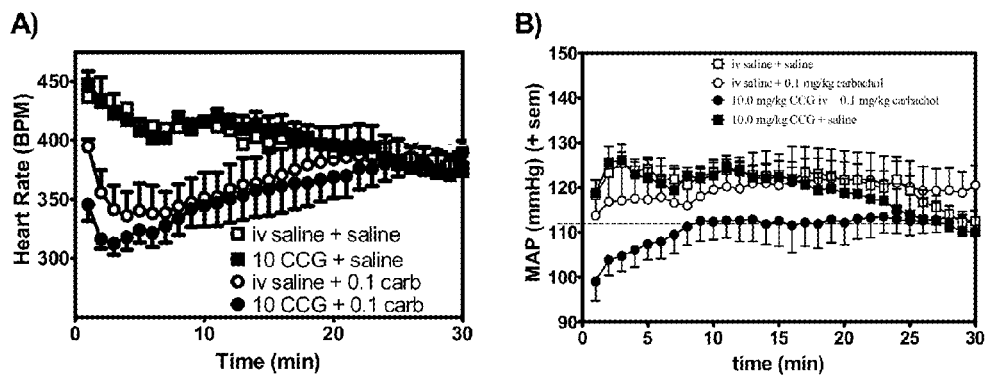
FIG. 24 shows that CCG-203769 potentiates the bradycardic effect of carbachol in freely-moving rats. A) CCG-203769 has no effect upon heart rate when administered alone, however it significantly potentiates (p<0.0001, 2-way ANOVA) the effect of carbachol (0.1 mg/kg). B) CCG-203769 does not affect blood pressure when administered alone.

Physiological Effects of CCG-203769 in freely-moving rats: RGS4 is the major RGS protein expressed in the sinoatrial node (SAN) and knockdown of RGS4 in these cells potentiates muscarinic signaling (Cifelli et al., (2008) Circ Res 103, 527-535). The muscarinic agonist carbachol can induce a transient bradycardic effect by activating M2 receptors in the SAN. In freely moving rats, a significant decrease in heart rate was observed after intraperitoneal administration of 0.1 mg/kg carbachol with no corresponding change in blood pressure as compared to saline injection (FIG. 24). CCG-203769 (10 mg/kg, IV) has no significant effect upon heart rate or blood pressure (FIG. 24B). However, when CCG-203769 (10 mg/kg, IV) is administered immediately prior to an injection of carbachol (0.1 mg/kg, IP), the bradycardic effects of the muscarinic agonist are significantly potentiated in these animals as compared to those that received saline instead of CCG-203769 (FIG. 24A). While the data show a trend towards decreased blood pressure in the animals that received carbachol and CCG-203769, this effect does not reach statistical significance (FIG. 24B).

TABLE 7

| RGS Protein | $IC_{50}$ (µM) | Fold Selectivity (RGS4) |
|---|---|---|
| RGS4 | 0.017 | 1 |
| RGS7 | >100 | >6000 |
| RGS8 | 79 | 4650 |
| RGS16 | 6 | 350 |
| RGS19 | 0.14 | 8.2 |
| GSK3β | 5.4 | 320 |
| PLCβ | >100 | >6000 |
| Papain | >100 | >6000 |

Example 6

Antidepressant Activity

Figure 25:
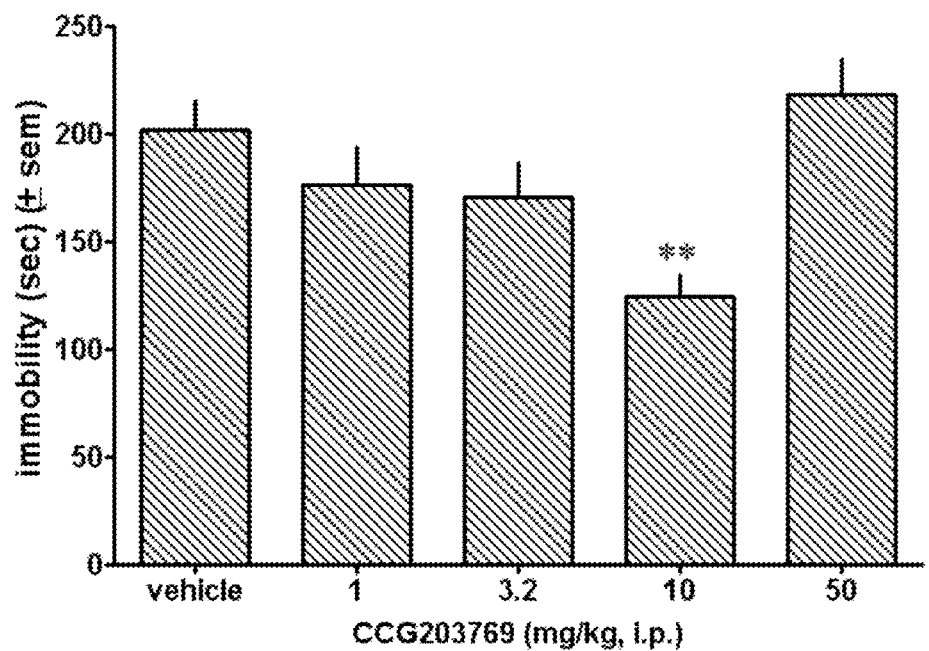
FIG. 25 shows the effect of CCG203769 on the tail suspension test for depression in mice.
Figure 26:
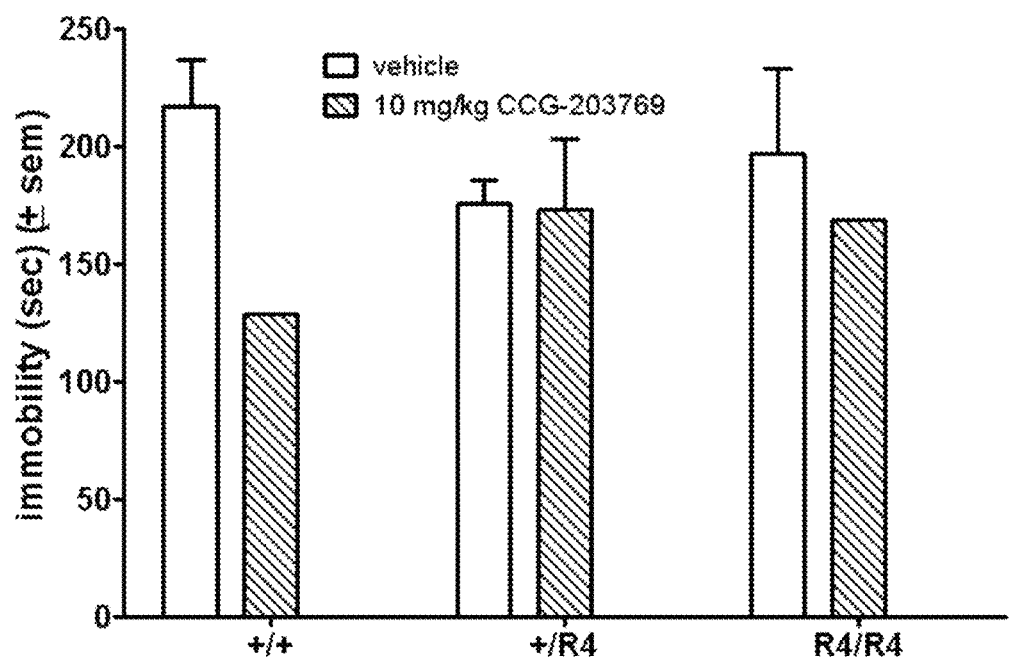
FIG. 26 shows the effect of CCG-203769 in wild-type (+/+), RGS4 knockout mice (R4/R4) and mice heterozygous for RGS4 (+/R4) on the tail suspension test for depression in mice.

This Example describes antidepressant activity of compounds of embodiments of the present invention. Antidepressant-like effects of CCG 203769: The tail suspension test in mice is a model of learned helplessness and is used as an assay for antidepressant medications. In this test antidepressant drugs (such as SSRIs) decrease the time the animals spend immobile by increasing escape-like behaviors. Mice rendered insensitive to RGS protein regulation through a mutation in Gαi2 (G184S) exhibited spontaneous antidepressant-like behavior in this test and an increased potency of SSRI's (Talbot et al., (2010) PNAS). CCG-203769 given IP to mice decreases their immobility time in a dose-dependent manner, reaching a significant effect at 10 mg/kg (FIG. 25). In RGS4 knockout mice the effect of 10 mg/kg CCG203769 is lost, indicating that the compound is acting at the RGS4 protein (FIG. 26).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A composition comprising a compound having the structure:

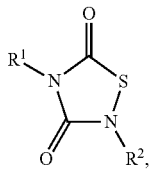

wherein $R^1$ is selected from the group consisting of

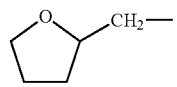

C2-C4 alkyl-$OR^3$, C1-C3 alkyl-heteroaryl-$R^3$, C4-C10 cycloalkyl wherein one or more $CH_2$ is replaced by O, and C2-C6 alkynyl, optionally substituted; R2 is a C2-C4 alkyl; $R^3$ is selected from the group consisting of C1-C6 alkyl, C0-C4 alkyl-aryl, C0-C4 alkyl-heteroaryl, and C2-C4 alkyl-$OR^4$; and $R^4$ is C1-C4 alkyl.

2. The composition of claim 1, wherein $R^1$ is selected from the group consisting of C2-C4 alkyl-$OR^3$; C1-C3 alkyl-heteroaryl-$R^3$; C4-C10 cycloalkyl, wherein at least one $CH_2$ is replaced by O; and C2-C6 alkynyl; R2 is a C2-C4 alkyl $R^3$ is selected from the group consisting of C1-C6 alkyl, C0-C4 alkyl-aryl, C0-C4 alkyl-heteroaryl, and C2-C4 alkyl-$OR^4$; and $R^4$ is C1-C4 alkyl.

3. The composition of claim 1, wherein $R^1$ is C2-C3 alkyl-O—C1-C4 alkyl and R2 is a C2-C4 alkyl.

4. The composition of claim 1, wherein said heteroaryl is 1,2,3-triazole.

5. The composition of claim 1, wherein R3 is selected from the group consisting of $CH_3$, $CH_2CH_3$, and $CH_2Ph$.

6. The composition of claim 1, wherein said compound is selected from the group consisting of,

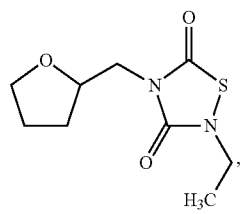

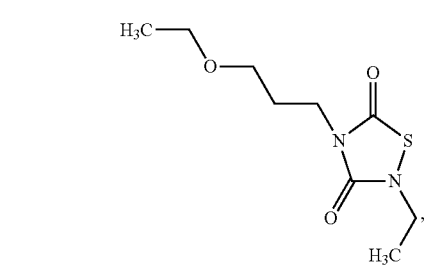

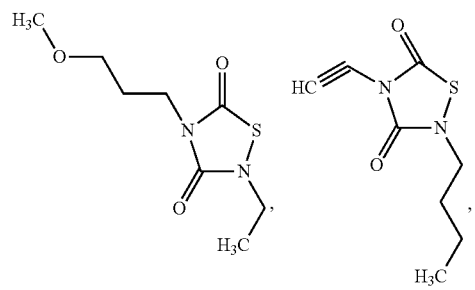

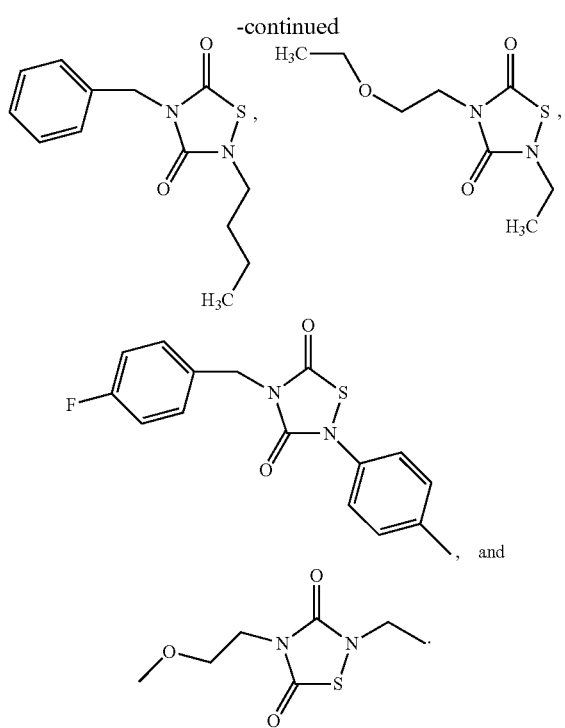

7. The composition of claim 1, wherein said composition is a pharmaceutical composition.

8. The composition of claim 7, wherein said composition further comprises a pharmaceutically acceptable carrier.

9. A method of inhibiting a regulator of G-protein Signaling (RGS) domain protein, comprising contacting said protein with a compound having the structure:

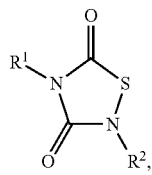

wherein $R^1$ is selected from the group consisting of

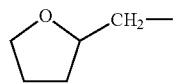

C2-C4 alkyl-$OR^3$, C1-C3 alkyl-heteroaryl-$R^3$, C4-C10 cycloalkyl wherein one or more $CH_2$ is replaced by O, and C2-C6 alkynyl, optionally substituted, R2 is a C2-C4 alkyl; $R^3$ is selected from the group consisting of C1-C6 alkyl, C0-C4 alkyl-aryl, C0-C4 alkyl-heteroaryl, and C2-C4 alkyl-$OR^4$; and $R^4$ is C1-C4 alkyl.

10. The method of claim 9, wherein $R^1$ is selected from the group consisting of C2-C4 alkyl-$OR^3$; C1-C3 alkyl-heteroaryl-$R^3$; C4-C10 cycloalkyl, wherein at least one $CH_2$ is replaced by O; and C2-C6 alkynyl; R2 is a C2-C4 alkyl; $R^3$ is selected from the group consisting of C1-C6 alkyl, C0-C4 alkyl-aryl, C0-C4 alkyl-heteroaryl, and C2-C4 alkyl-$OR^4$; and $R^4$ is C1-C4 alkyl.

11. The method of claim 9, wherein R1 is C2-C3 alkyl-O—C1-C4 alkyl and R2 is a C2-C4 alkyl.

12. The method of claim 9, wherein said heteroaryl is 1,2,3-triazole.

13. The method of claim 9, wherein $R^3$ is selected from the group consisting of $CH_3$, $CH_2CH_3$, and $CH_2Ph$.

14. The method of claim 9, wherein said compound is selected from the group consisting of

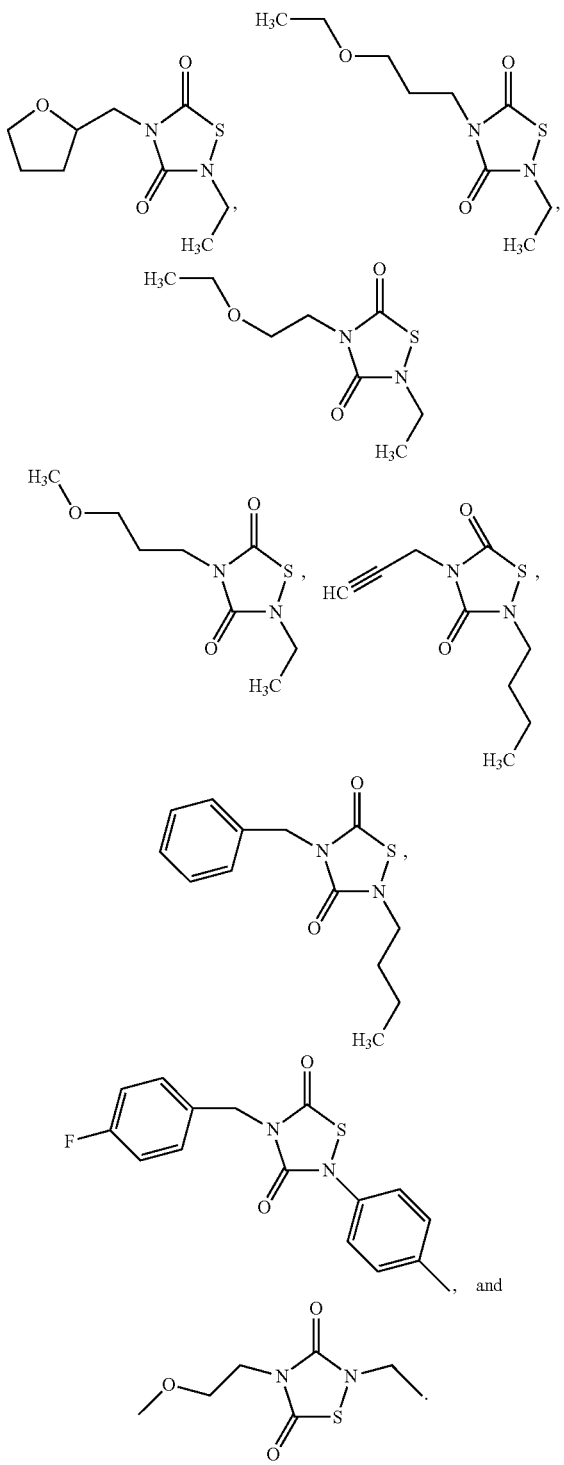

15. The method of claim 9, wherein said protein is in a cell.

16. The method of claim 15, wherein said cell is in an animal.

* * * * *